US011225658B2

(12) United States Patent
Yan et al.

(10) Patent No.: US 11,225,658 B2
(45) Date of Patent: Jan. 18, 2022

(54) ENRICHMENT AND SEQUENCING OF RNA SPECIES

(71) Applicant: New England Biolabs, Inc., Ipswich, MA (US)

(72) Inventors: Bo Yan, Ipswich, MA (US); Laurence Ettwiller, Ipswich, MA (US); Ira Schildkraut, Ipswich, MA (US); George Tzertzinis, Ipswich, MA (US); Ivan R. Correa, Jr., Ipswich, MA (US); Nan Dai, Ipswich, MA (US); Madalee G. Wulf, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 497 days.

(21) Appl. No.: 15/786,020

(22) Filed: Oct. 17, 2017

(65) Prior Publication Data
US 2018/0030436 A1    Feb. 1, 2018

Related U.S. Application Data

(63) Continuation-in-part of application No. 15/137,394, filed on Apr. 25, 2016, now Pat. No. 10,428,368, which is a continuation-in-part of application No. PCT/US2014/068737, filed on Dec. 5, 2014.

(60) Provisional application No. 62/409,151, filed on Oct. 17, 2016, provisional application No. 62/166,190, filed on May 26, 2015, provisional application No. 62/011,918, filed on Jun. 13, 2014, provisional application No. 62/002,564, filed on May 23, 2014, provisional application No. 61/920,380, filed on Dec. 23, 2013, provisional application No. 61/912,367, filed on Dec. 5, 2013.

(51) Int. Cl.
*C12N 15/10* (2006.01)
*C12Q 1/6806* (2018.01)
*C12Q 1/6869* (2018.01)
*C07H 21/00* (2006.01)

(52) U.S. Cl.
CPC ..... *C12N 15/1096* (2013.01); *C12N 15/1093* (2013.01); *C12Q 1/6806* (2013.01); *C07H 21/00* (2013.01); *C12Q 1/6869* (2013.01)

(58) Field of Classification Search
CPC .......................... C12Q 1/6806; C12N 15/1096
See application file for complete search history.

(56) References Cited

U.S. PATENT DOCUMENTS

| | | | | |
|---|---|---|---|---|
| 6,174,669 B1* | 1/2001 | Hayashizaki | .......... | C07H 21/00 435/6.16 |
| 8,486,666 B2 | 7/2013 | Schildkraut | | |
| 2004/0077024 A1* | 4/2004 | Holmberg | ........ | G01N 33/54306 435/7.5 |
| 2007/0281336 A1* | 12/2007 | Jendrisak | ............... | C12N 15/111 435/69.1 |
| 2012/0196279 A1* | 8/2012 | Underwood | ............ | C12P 19/34 435/6.1 |
| 2014/0147454 A1* | 5/2014 | Chakraborty | .......... | C12N 15/67 424/185.1 |
| 2017/0253911 A1 | 9/2017 | Schildkraut | | |

FOREIGN PATENT DOCUMENTS

WO    WO2015/085142    6/2015

OTHER PUBLICATIONS

Jernoimo et al. Systematic analysis of the protein interaction network for hte human transcription machinery reveals the identity of the 7SK capping enzyme. Molecular Cell, vol. 27, pp. 262-274, Jul. 2007. (Year: 2007).*
Kowalska et al. Synthesis and characterization of mRNA cap analogs containing phosphorothioate sustitutions that bind tightly to elF4E and are resistant to the decapping pyrophosphatase DcpS. RNA, vol. 14, pp. 1119-1131, 2008. (Year: 2008).*
Song et al. Multiple Nudix family proteins possess mRNA decapping activity. RNA, vol. 19, pp. 390-399, Jan. 25, 2013. (Year: 2013).*
Holmberg et al. The biotin-streptavidin interaction can be reversibly broken using water at elevated temperatures. Electrophoresis, vol. 26, pp. 501-510, 2005. (Year: 2005).*
Belyavsky et al. PCR-based cDNA library construction: general cDNA libraries at the level of a few cells. Nucleic Acids Research, vol. 17, No. 8, pp. 2919-2932, 1989. (Year: 1989).*
Bitinaite et al. USERTM friendly DNA engineering and clonign method by uracil excision. Nucleic Acids Research, vol. 35, No. 6, pp. 1992-2002, Mar. 2007. (Year: 2007).*
Lichty et al. Comparison of affinity tags for protein purification. Protein Expression and Purification, vol. 41, pp. 98-105, 2005. (Year: 2005).*

(Continued)

*Primary Examiner* — Jennifer Dunston
(74) *Attorney, Agent, or Firm* — New England Biolabs, Inc

(57) ABSTRACT

Provided herein is a method for making an cDNA library, comprising adding an affinity tag-labeled GMP to the 5' end of targeted RNA species in a sample by optionally decapping followed by incubating the sample with an affinity tag-labeled GTP and a capping enzyme, enriching for RNA comprising the affinity tag-labeled GMP using an affinity matrix that binds to the affinity tag, reverse transcribing the enriched RNA to produce a population of cDNAs, and adding a tail to the 3' end of the population of cDNAs using a terminal transferase, to produce an cDNA library.

20 Claims, 19 Drawing Sheets
(11 of 19 Drawing Sheet(s) Filed in Color)
Specification includes a Sequence Listing.

(56) References Cited

OTHER PUBLICATIONS

Soni, et al., Clin Chem. (2007) 53: 1996-2001.
Matz, et al., Nucl. Acids Res. (1999) 27: 1558-1560.
Wu, et al., Nat Methods. (2014) 11:41-46.
Grudzien-Nogalska, et al., Wiley Interdisciplinary Reviews: RNA. 2017; 8:E1379.
Carnici, et al., Genomics. 1996 37: 327-36.
Liu, et al., EMBO J. 2002 21: 4699-708.
Xue, et al., Nucleic Acids Research. 2010 38: 360-9.
Jiao, et al., Cell. 2017;168:1015-1027.e10.
Walters, et al., Proc. of the Natl. Acad, of Sci. 2017 114: 480-485.
Chen, et al., Nature Chemical Biology. 2009;5:879-81.
Abdelhamid, et al., PLoS ONE. 2014;9:e102895.
Hofer, et al. Nature Chemical Biology. 2016;12:730-4.

\* cited by examiner

FIG. 4B  FIG. 4C

A. Workflow

B. Sequencing Data display

```
APTX_SCHPO    -AKEPIVEDIPKKYRKQS------------------------FRDNLKVYIESPES
APTX_YEAST    -------------------------------------------IFRHFQEKFRIKKSDD--
APTX_CIOIN    FDSPSPMSSRCEKKAESN--------------------KRAPTHKHWSQGLKASMEDP---
APTX_DANRE    -SPPPPKKTTPPAGEKSE--------------------------SAGHWSQGLKASMQDP--
APTX_TAKRU    VSVSVSQKEAPKMSVRSNVHFSLLSILLSGLLSEGVGKMLQGSVGHWNLGLKASMQDP---
APTX_XENLA    -SSSSGRISSCPTQGKSNV---------------------QEVKSQGHWSQDLKVSMQDP--
APTX_XENTR    -SSSSGKNSSCSTEEKYNA---------------------QEVKSQGHWSQGLKASMQDP--
APTX_CHICK    ADLRPSKSSVSPHEGTTS---------------------RKEHLGHWSQGLKSSMQDP---
APTX_MOUSE    -GSSPSQCSVSPKKDKNGA---------------------TKKESLGHWSQGLKMSMKDP--
APTX_RAT      -GASPSQCSVSPKTGKHGA---------------------AKEESLGHWSQGLKISMKDP--
APTX_CANLF    -GSDSSQCSVPLNKGKDAP---------------------TKKESLGHWSQGLKISMQDP--
APTX_HUMAN    -GSNSGQCSVPLKKGKDAP---------------------IKKESLGHWSQGLKISMQDP--
APTX_MACFA    -GSNHNQCSVPPKKGKDAP---------------------IKKESLGHWSQGLKISMQDP--
APTX_BOVIN    -GSNPHQCSVPPKKEKDAS---------------------IKKESLGHWSQGLKISMEDP--
APTX_PIG      -GSNPSQCSVPPKKEKDAA---------------------TKKESLSHWSQGLKISMEDP--

APTX_SCHPO    YKNVIYYDDDVVLVRDMFPKSKMHLLLMTRDPHLTHVHPLEIMMKHRSLVEKLVSYVQGD
APTX_YEAST    ----------------DKDP------------------CWDDI------LKDKNKFVRN-
APTX_CIOIN    -ELVVKEDEQIVVIKDKYPKAKYHWLIL----------PKDSISSTKNLSTDNIELLKH-
APTX_DANRE    -KMQVYKDDSVVVIKDKYPKARYHWLVL----------PWQSISSLKALRSEHVELLKH-
APTX_TAKRU    -EMQVYKDDKVVVIKDKYPKARYHWLVL----------PWQSISSLKALRKEHCDLVKH-
APTX_XENLA    -TMQVFKDDKIVVIKDKYPKARYHWLVL----------PWQSIASLKVLRAEHLELVQH-
APTX_XENTR    -TMQVFKDDKVVVIKDKYPKARYHWLVL----------PWQSIANLKVLRAEHLELVQH-
APTX_CHICK    -KVQVYKDEKTVVIKDKYPKARYHWLVL----------PWDSISSLKSVTREHLGLLEH-
APTX_MOUSE    -KMQVYKDDQVVVIKDKYPKARHHWLVL----------PWASISSLKVVTSEHLELLKH-
APTX_RAT      -KMQVYKDDQVVVIKDKYPKARHHWLVL----------PWASISSLKVVTSEHLELLKH-
APTX_CANLF    -KMQVYKDEQVVVIKDKYPKARYHWLVL----------PWASVSSLKAVTGEHLELLKH-
APTX_HUMAN    -KMQVYKDEQVVVIKDKYPKARYHWLVL----------PWTSISSLKAVAREHLELLKH-
APTX_MACFA    -KMQVYKDEQVVVIKDKYPKARYHWLVL----------PWTAISSLKAVTREHLELLKH-
APTX_BOVIN    -KMQVYKDEQVVVIKDKYPKARFHWLVL----------PWASISSLKAVTREHLELLRH-
APTX_PIG      -KMQVYKDDQVVVIKDKYPKARYHWLVL----------PWASISSLKAVTREHLELLRH-

APTX_SCHPO    LSGLIFDEARNCLSQQLTNEALCNYIKVGFHAGPSMNNLHLHIMTLDHVSPSLKNSAHYI
APTX_YEAST    ------FVQV-------------------GIHSVPSMANLHIHVISKDFHSVRLKNKKHYN
APTX_CIOIN    -----ILKVGQELAAEVKDKQPDVEFRFGYHAVASMSQMHMHVISQDFQSSSFKTKKHWN
APTX_DANRE    -----MQRVADQMVEQCPDAH-KLSFRLGYHAIPSMSHVHLHVISQDFDSPCLKNKKHWN
APTX_TAKRU    -----MQQVAEQMIRQCPDAS-TPRFRSGYHAIPSMSHVHLHVISQDFDSPCLKNKKHWN
APTX_XENLA    -----MDAVGHNIAREHTNSK-CAPFRFGYHAIPSMSHVHLHVISQDFDSPCLKNKKHWN
APTX_XENTR    -----MHAVGQKIAKEHSDSK-CAPFQLGYHAIPSMSHVHLHVISQDFDSPCLKNKKHWN
APTX_CHICK    -----MHAVGQKMIQQCPAKE-SLEFRLGYHAIPSMSQLHLHVISQDFDSPALKTKKHWN
APTX_MOUSE    -----MHAVGEKVIADFAGSS-KLRFRLGYHAIPSMSHVHLHVISQDFDSPCLKNKKHWN
APTX_RAT      -----MHAVGEKVIADFTGSS-KLRFRLGYHAIPSMSHVHLHVISQDFDSPCLKNKKHWN
APTX_CANLF    -----MHTVGEKMIADFAGSS-KLRFRLGYHAIPSMSHVHLHVISQDFDSPCLKNKKHWN
APTX_HUMAN    -----MHTVGEKVIVDFAGSS-KLRFRLGYHAIPSMSHVHLHVISQDFDSPCLKNKKHWN
APTX_MACFA    -----MHTVGEKVIVDFAGSS-KLRFRLGYHAIPSMSHVHLHVISQDFDSPCLKNKKHWN
APTX_BOVIN    -----MHAVGEKVIADFAGSS-KFRFRLGYHAIPSMSHVHLHVISQDFDSPCLKNKKHWN
APTX_PIG      -----MHTVGEKVIADFAGSS-KLRFRLGYHAIPSMSHVHLHVISQDFDSPCLKNKKHWN
```

FIG. 14 (Cont. 1)

```
APTX_SCHPO    SFTSPFFVKIDTPTSNLPTRG------TLTSLFQE-DLKCWRCGETFGRHFTKLKAHLQE
APTX_YEAST    SFNTGFFISWDDLPLNGKNLG--TDKEIETTYLKEHDLLCCYCQRNFSNKFSLLKKHLEL
APTX_CIOIN    SFTTDYFVDATDIINELETGGKVKDRRTMTSLLNE-PLKCHRCKKPQKN-IPTLKKHIDS
APTX_DANRE    SFTTDYFVESQDVISMLEHDGKVQVKEGAGELLKL-PLRCHVCGKEQTT-IPKLKDHLKT
APTX_TAKRU    SFTTDYFIESQAVIQMLETDGSISIKEGATELLKL-PLRCHVCRKEFSN-IPALKQHLNS
APTX_XENLA    SFTTDYFLESQAVIEMLKTHGKVNVKERISDVLKT-PLLCHMCKKEQAT-MPQLKEHLKK
APTX_XENTR    SFTTDYFLESQAMIEMIKTHGKVNVKDGVSELLKT-PLMCHICRKEQAN-MPQLKEHLKK
APTX_CHICK    SFTTEYFLNSEEVIEMVRSKGKVTVNDQASELLKL-PLRCHLCKQQLST-IPQLKEHLKK
APTX_MOUSE    SFNTEYFLESQAVIKMVQEAGRVTVKDGTCELLKL-PLRCHECQQLLPS-IPQLKEHLRK
APTX_RAT      SFNTEYFLESQAVIKMVQEAGRVTVKDGTCELLKL-PLRCHECQQLLPS-IPQLKEHLRK
APTX_CANLF    SFNTEYFLESQAVIEMVQHAGRVSVRDGMPELLKL-PLRCHECQQLLPS-IPQLKEHLRR
APTX_HUMAN    SFNTEYFLESQAVIEMVQEAGRVTVRDGMPELLKL-PLRCHECQQLLPS-IPQLKEHLRK
APTX_MACFA    SFNTEYFLESQAVIEMVQEAGRVTVRDGMPELLKL-PLRCHECQQLLPS-IPQLKEHLRK
APTX_BOVIN    SFNTEYFLESQAVIEMVQEAGRVTVRDGMPELLKL-PLRCHECQQLLPS-IPQLKEHLRK
APTX_PIG      SFNTEYFLESQAVIEMVQEAGRVTVRDGMPELLKL-PLRCHECQQLLPS-IPQLKEHLRK

APTX_SCHPO    EYDDWLDKSVSM
APTX_YEAST    ---EFNSHFELK
APTX_CIOIN    ---CQK------
APTX_DANRE    ---HLPS-----
APTX_TAKRU    ---HFPS-----
APTX_XENLA    ---HWPT-----
APTX_XENTR    ---HWPT-----
APTX_CHICK    ---HWTK-----
APTX_MOUSE    ---HWGG-----
APTX_RAT      ---HWGG-----
APTX_CANLF    ---HWPK-----
APTX_HUMAN    ---HWTQ-----
APTX_MACFA    ---HWTQ-----
APTX_BOVIN    ---HWSK-----
APTX_PIG      ---HWPK-----
```

FIG. 14 (Cont. 2)

```
              1         10        20        30        40        50        60
              |         |         |         |         |         |         |
DCPS_ASCSU    --------------------------MVDEVDANSTGDNSLVNMKGFSFKEVLGSDSARK
DCPS_BOVIN    MAELAHQQSKRKRELDAEEAEASSTEGEEAGVGNGTSAPVRLPFSGFRVKKVLRESARDK
DCPS_CAEEL    ------------------------MKRIADEELVREERAEESTQKWLQDAKFQEILGADSSHK
DCPS_HUMAN    MADAAPQLGKRKRELDVEEAHAASTEEKEAGVGNGTCAPVRLPFSGFRLQKVLRESARDK
DCPS_MOUSE    MADTAPQL-KRKREQEAEEAETPSTEEKEAGVGNGTSAPVRLPFSGFRVQKVLRESARDK
DCPS_PIG      MADTAPQPSKRKRERDPEEAEAPSTEEKEARVGNGTSAPVRLPFSGFRVKKVLRESARDK
DCPS_RAT      MADTAPQL-KRKREQEAEEAETPSTEEKEAGVGNGTSAPVRLPFSGFRVQKVLRESARDK
DCPS_SCHPO    ---------------------------------MEESSAAKIQLLKEFKFEKILKDDTKSK
DCPS_YEAST    ---------------------------------MSQLPTDFASLIKRFQFVSVLDSNPQTK
DCS2_YEAST    ---------------------------------MGSQDLASLIGRFKYVRVLDSNPHTK

DCPS_ASCSU    SAFIL------LDSSNGENAILLADKNAFPVDKTSWS-------------AILTGST-LKP
DCPS_BOVIN    IIFLHGKVNEASGDGDGEDAVVILEKTPFQVDQVA-Q-------------LLKGSPELQL
DCPS_CAEEL    SLFVL------LSHPDGSQGILLANKSPFSEEKSDIE-------------KLLATAQLQE
DCPS_HUMAN    IIFLHGKVNEASGDGDGEDAVVILEKTPFQVEQVA-Q-------------LLTGSPELQL
DCPS_MOUSE    IIFLHGKVNEDSGDTHGEDAVVILEKTPFQVEHVA-Q-------------LLTGSPELKL
DCPS_PIG      IIFLHGKVNEASGDGDGEDAIVILEKTPFQVDQVA-Q-------------LLMGSPELQL
DCPS_RAT      IIFLHGKVNEDSGDTHGEDAVVILEKTPFQVEHVA-Q-------------LLTGNPELKL
DCPS_SCHPO    IITLYGKI--------RNEVALLLLEKTAFDLNTIKLD-----------QLATFLQDTKL
DCPS_YEAST    VMSLLGTIDNKDAIITAEKTHFLFDETVRRPSQDGRSTPVLYNCE-NEYSCINGIQELKE
DCS2_YEAST    VISLLGSIDGKDAVLTAEKTHFIFDETVRRPSQSGRSTPIFFHREIDEYSFLNGITDLKE

DCPS_ASCSU    IMKNDIYSSY---TLCMPNEFSDVKSTLIYPCNEKHIAKYRDQKRFIINETPEDYRTITL
DCPS_BOVIN    QFSNDVYSTY---HLFPPRQLSDVKTTVVYPATEKHLQKYLRQDLHLVRETGSDYRNVTL
DCPS_CAEEL    ISRNDIFGSY---NIEIDPKLNLLKSQLIYPINDRLIAKYRQEEKFVIRETPELYETVTR
DCPS_HUMAN    QFSNDIYSTY---HLFPPRQLNDVKTTVVYPATEKHLQKYLRQDLRLIRETGDDYRNITL
DCPS_MOUSE    QFSNDIYSTY---NLFPPRHLSDIKTTVVYPATEKHLQKYMRQDLRLIRETGDDYRTITL
DCPS_PIG      QFSNDIYSTY---HLFPPRQLSDVKTTVVYPATEKHLQKYLHQDLHLVRETGGDYKNITL
DCPS_RAT      QFSNDIYSTY---NLFPPRHLSDIKTTVVYPASEKHLQKYMRQDLRLIRETGDDYRSLTL
DCPS_SCHPO    VENNDVFHWFLSTNFQDCSTLPSVKSTLIWPASETHVRKYSSQKKRMVCETPEMYLKVTK
DCPS_YEAST    ITSNDIYYWGLSVIKQDMESNPTAKLNLIWPATPIHIKKYEQQNFHLVRETPEMYKRIVQ
DCS2_YEAST    LTSNDIYYWGLSVLKQHILHNPTAKVNLIWPASQFHIKGYDQQDLHVVRETPDMYRNIVV

DCPS_ASCSU    PYIQRNQ--MSLEWVYNILDHKAEVDRIIYEE----TDPHDGFILAPDLKWSGEQLECLYV
DCPS_BOVIN    PHLESQS--LSIQWVYNILDKKAEADRIVFEN---PDPSDGFVLIPDLKWNQQQLDDLYL
DCPS_CAEEL    PYIEKYQ--LNLNWVYNCLEKRSEVDKIVFED---PDNENGFVLLQDIKWDGKTLENLYV
DCPS_HUMAN    PHLESQS--LSIQWVYNILDKKAEADRIVFEN---PDPSDGFVLIPDLKWNQQQLDDLYL
DCPS_MOUSE    PYLESQS--LSIQWVYNILDKKAEADRIVFEN---PDPSDGFVLIPDLKWNQQQLDDLYL
DCPS_PIG      PHLESQS--LSIQWVYNILDKKAEADRIVFEN---PDPSDGFVLIPDLKWNQKQLDDLYL
DCPS_RAT      PYLESQS--LSIQWVYNILDKKAEADRIVFEN---PDPSDGFVLIPDLKWNQQQLDDLYL
DCPS_SCHPO    PFIETQR-GPQIQWVENILTHKAEAERIVVED---PDPLNGFIVIPDLKWDRQTMSALNL
DCPS_YEAST    PYIEEMCNNGRLKWVNNILYEGAESERVVYKDFSEENKDDGFLILPDMKWDGMNLDSLYL
DCS2_YEAST    PFIQEMCTSERMKWVNNILYEGAEDDRVVYKEYSSRNKEDGFVILPDMKWDGINIDSLYL
```

FIG. 15

```
DCPS_ASCSU    QALVRRKGIKSIRDLTANDLPLLEGIRDKGLNAIKE--KYGLDKHQIRAYFHYQPSFYHL
DCPS_BOVIN    IAICHRRGIKSLRDLTAEHLPLLRNILREGQEAILR--RYQVAADRLRVYLHYLPSYYHL
DCPS_CAEEL    LAICHRHGLKSVRDLTGDDLEMLYNMRDKSLEAINQ--KYGLKTDQIKCYFHYQPSFYHL
DCPS_HUMAN    IAICHRRGIRSLRDLTPEHLPLLRNILHQGQEAILQ--RYRMKGDHLRVYLHYLPSYYHL
DCPS_MOUSE    IAICHRRGIRSLRDLTPEHLPLLRNILREGQEAILK--RYQVTGDRLRVYLHYLPSYYHL
DCPS_PIG      IAICHRRGIKSLRDLTPEHLPLLRNILREGQEAILQ--RYQVTGDRLRVYLHYLPSYYHL
DCPS_RAT      IAICHRRGIRSLRDLTPEHLPLLRNILREGQEAILK--RYQVTGDRLRVYLHYLPSYYHL
DCPS_SCHPO    MAIVHATDIASIRDLKYKHIPLLENIRNKVLTEVPK--QFSVDKNQLKMFVHYLPSYYHL
DCPS_YEAST    VAIVYRTDIKTIRDLRYSDRQWLINLNNKIRSIVPGCYNYAVHPDELRILVHYQPSYYHF
DCS2_YEAST    VAIVYRDDIKSLRDLNPNHRDWLIRLNKKIKTIIPQHYDYNVNPDELRVFIHYQPSYYHF

DCPS_ASCSU    HVHFIHVSYEA-PAS-GVAKAVLLDDVINNLK-LIPDFYQRSTLTFTAKEQDPIYRREN-
DCPS_BOVIN    HVHFTALGFEA-PGA-GVERAHLLAEVIDNLE-QDPEHYQRRTLTFALRADDPLLALLQE
DCPS_CAEEL    HVHFINLKYDA-PAS-TTMSAILLDDVINNLE-LNPEHYKKSTLTFTRKNGDKLMEMFRE
DCPS_HUMAN    HVHFTALGFEA-PGS-GVERAHLLAEVIENLE-CDPRHYQQRTLTFALRADDPLLKLLQE
DCPS_MOUSE    HVHFTALGFEA-PGS-GVERAHLLAQVIENLE-CDPKHYQQRTLTFALRTDDPLLQLLQK
DCPS_PIG      HVHFTALGFEA-PGA-GVERAHLLAEVIENLE-QDPEHYQRRTLTFALRADDPLLTLLQE
DCPS_RAT      HVHFTALGFEA-PGS-GVERAHLLAEVIENLE-CDPKHYQRRTLTFALRTDDPLLQLLQK
DCPS_SCHPO    HVHILHVDHETGDGS-AVGRAILLDDVIDRLR-NSPDGLENVNITFNIGEQHFLFQPLTN
DCPS_YEAST    HIHIVNIKHPGLGNSIAAGKAILLEDIIEMLNYLGPEGYMNKTITYAIGENHDLWKRGLE
DCS2_YEAST    HVHIVNIRHPGVGEERGSGMTILLEDVIEALGFLGPEGYMKKTLTYVIGENHDLWKKGFK

DCPS_ASCSU    --------------------------
DCPS_BOVIN    AQRS----------------------
DCPS_CAEEL    ALKN----------------------
DCPS_MOUSE    AQQERN--------------------
DCPS_PIG      AQRS----------------------
DCPS_RAT      AQQP----------------------
DCPS_SCHPO    MNA-----------------------
DCPS_YEAST    EELTKQLERDGIPKIPKIVNGFK----
DCS2_YEAST    EEVEKQLKHDGIATSPEKGSGFNTNLG
```

FIG. 15 (Cont.)

SEQUENCE LISTING

<160> NUMBER OF SEQ ID NOS: 32

<210> SEQ ID NO 1
<211> LENGTH: 301
<212> TYPE: PRT
<213> ORGANISM: Ascaris suum

<400> SEQUENCE: 1

```
Met Val Asp Glu Val Asp Ala Asn Ser Thr Gly Asp Asn Ser Leu Val
1               5                   10                  15

Asn Met Lys Gly Phe Ser Phe Lys Glu Val Leu Gly Ser Asp Ser Ala
            20                  25                  30

Arg Lys Ser Ala Phe Ile Leu Leu Asp Ser Ser Asn Gly Glu Asn Ala
        35                  40                  45

Ile Leu Leu Ala Asp Lys Asn Ala Phe Pro Val Asp Lys Thr Ser Trp
    50                  55                  60

Ser Ala Ile Leu Thr Gly Ser Thr Leu Lys Pro Ile Met Lys Asn Asp
65                  70                  75                  80

Ile Tyr Ser Ser Tyr Thr Leu Cys Met Pro Asn Glu Phe Ser Asp Val
                85                  90                  95

Lys Ser Thr Leu Ile Tyr Pro Cys Asn Glu Lys His Ile Ala Lys Tyr
            100                 105                 110

Arg Asp Gln Lys Arg Phe Ile Ile Asn Glu Thr Pro Glu Asp Tyr Arg
        115                 120                 125

Thr Ile Thr Leu Pro Tyr Ile Gln Arg Asn Gln Met Ser Leu Glu Trp
    130                 135                 140
```

```
Val Tyr Asn Ile Leu Asp His Lys Ala Glu Val Asp Arg Ile Ile Tyr
145                 150                 155                 160

Glu Glu Thr Asp Pro His Asp Gly Phe Ile Leu Ala Pro Asp Leu Lys
            165                 170                 175

Trp Ser Gly Glu Gln Leu Glu Cys Leu Tyr Val Gln Ala Leu Val Arg
            180                 185                 190

Arg Lys Gly Ile Lys Ser Ile Arg Asp Leu Thr Ala Asn Asp Leu Pro
            195                 200                 205

Leu Leu Glu Gly Ile Arg Asp Lys Gly Leu Asn Ala Ile Lys Glu Lys
    210                 215                 220

Tyr Gly Leu Asp Lys His Gln Ile Arg Ala Tyr Phe His Tyr Gln Pro
225                 230                 235                 240

Ser Phe Tyr His Leu His Val His Phe Ile His Val Ser Tyr Glu Ala
            245                 250                 255

Pro Ala Ser Gly Val Ala Lys Ala Val Leu Leu Asp Asp Val Ile Asn
            260                 265                 270

Asn Leu Lys Leu Ile Pro Asp Phe Tyr Gln Arg Ser Thr Leu Thr Phe
            275                 280                 285

Thr Ala Lys Glu Gln Asp Pro Ile Tyr Arg Arg Glu Asn
            290                 295                 300

<210> SEQ ID NO 2
<211> LENGTH: 337
<212> TYPE: PRT
<213> ORGANISM: Bos taurus

<400> SEQUENCE: 2

Met Ala Glu Leu Ala His Gln Gln Ser Lys Arg Lys Arg Glu Leu Asp
1               5                   10                  15

Ala Glu Glu Ala Glu Ala Ser Ser Thr Glu Gly Glu Ala Gly Val
            20                  25                  30

Gly Asn Gly Thr Ser Ala Pro Val Arg Leu Pro Phe Ser Gly Phe Arg
            35                  40                  45

Val Lys Lys Val Leu Arg Glu Ser Ala Arg Asp Lys Ile Ile Phe Leu
    50                  55                  60

His Gly Lys Val Asn Glu Ala Ser Gly Asp Gly Asp Gly Glu Asp Ala
65                  70                  75                  80

Val Val Ile Leu Glu Lys Thr Pro Phe Gln Val Asp Gln Val Ala Gln
                85                  90                  95

Leu Leu Lys Gly Ser Pro Glu Leu Gln Leu Gln Phe Ser Asn Asp Val
            100                 105                 110

Tyr Ser Thr Tyr His Leu Phe Pro Pro Arg Gln Leu Ser Asp Val Lys
            115                 120                 125

Thr Thr Val Val Tyr Pro Ala Thr Glu Lys His Leu Gln Lys Tyr Leu
    130                 135                 140

Arg Gln Asp Leu His Leu Val Arg Glu Thr Gly Ser Asp Tyr Arg Asn
145                 150                 155                 160

Val Thr Leu Pro His Leu Glu Ser Gln Ser Leu Ser Ile Gln Trp Val
            165                 170                 175

Tyr Asn Ile Leu Asp Lys Lys Ala Glu Ala Asp Arg Ile Val Phe Glu
            180                 185                 190

Asn Pro Asp Pro Ser Asp Gly Phe Val Leu Ile Pro Asp Leu Lys Trp
            195                 200                 205

Asn Gln Gln Gln Leu Asp Asp Leu Tyr Leu Ile Ala Ile Cys His Arg
```

```
            210                 215                 220
Arg Gly Ile Lys Ser Leu Arg Asp Leu Thr Ala Glu His Leu Pro Leu
225                 230                 235                 240

Leu Arg Asn Ile Leu Arg Glu Gly Gln Glu Ala Ile Leu Arg Arg Tyr
                245                 250                 255

Gln Val Ala Ala Asp Arg Leu Arg Val Tyr Leu His Tyr Leu Pro Ser
                260                 265                 270

Tyr Tyr His Leu His Val His Phe Thr Ala Leu Gly Phe Glu Ala Pro
            275                 280                 285

Gly Ala Gly Val Glu Arg Ala His Leu Leu Ala Glu Val Ile Asp Asn
                290                 295                 300

Leu Glu Gln Asp Pro Glu His Tyr Gln Arg Arg Thr Leu Thr Phe Ala
305                 310                 315                 320

Leu Arg Ala Asp Asp Pro Leu Leu Ala Leu Leu Gln Glu Ala Gln Arg
                325                 330                 335

Ser

<210> SEQ ID NO 3
<211> LENGTH: 311
<212> TYPE: PRT
<213> ORGANISM: Caenorhabditis elegans

<400> SEQUENCE: 3

Met Lys Arg Ile Ala Asp Glu Glu Leu Val Arg Glu Glu Arg Ala Glu
1               5                   10                  15

Glu Ser Thr Gln Lys Trp Leu Gln Asp Ala Lys Phe Gln Glu Ile Leu
                20                  25                  30

Gly Ala Asp Ser Ser His Lys Ser Leu Phe Val Leu Leu Ser His Pro
            35                  40                  45

Asp Gly Ser Gln Gly Ile Leu Leu Ala Asn Lys Ser Pro Phe Ser Glu
        50                  55                  60

Glu Lys Ser Asp Ile Glu Lys Leu Leu Ala Thr Ala Gln Leu Gln Glu
65                  70                  75                  80

Ile Ser Arg Asn Asp Ile Phe Gly Ser Tyr Asn Ile Glu Ile Asp Pro
                85                  90                  95

Lys Leu Asn Leu Leu Lys Ser Gln Leu Ile Tyr Pro Ile Asn Asp Arg
                100                 105                 110

Leu Ile Ala Lys Tyr Arg Gln Glu Lys Phe Val Ile Arg Glu Thr
            115                 120                 125

Pro Glu Leu Tyr Glu Thr Val Thr Arg Pro Tyr Ile Glu Lys Tyr Gln
            130                 135                 140

Leu Asn Leu Asn Trp Val Tyr Asn Cys Leu Glu Lys Arg Ser Glu Val
145                 150                 155                 160

Asp Lys Ile Val Phe Glu Asp Pro Asn Glu Asn Gly Phe Val Leu
                165                 170                 175

Leu Gln Asp Ile Lys Trp Asp Gly Lys Thr Leu Glu Asn Leu Tyr Val
                180                 185                 190

Leu Ala Ile Cys His Arg His Gly Leu Lys Ser Val Arg Asp Leu Thr
            195                 200                 205

Gly Asp Asp Leu Glu Met Leu Tyr Asn Met Arg Asp Lys Ser Leu Glu
            210                 215                 220

Ala Ile Asn Gln Lys Tyr Gly Leu Lys Thr Asp Gln Ile Lys Cys Tyr
225                 230                 235                 240

Phe His Tyr Gln Pro Ser Phe Tyr His Leu His Val His Phe Ile Asn
```

```
                        245                 250                 255
Leu Lys Tyr Asp Ala Pro Ala Ser Thr Thr Met Ser Ala Ile Leu Leu
            260                 265                 270

Asp Asp Val Ile Asn Asn Leu Glu Leu Asn Pro Glu His Tyr Lys Lys
                275                 280                 285

Ser Thr Leu Thr Phe Thr Arg Lys Asn Gly Asp Lys Leu Met Glu Met
    290                 295                 300

Phe Arg Glu Ala Leu Lys Asn
305                 310

<210> SEQ ID NO 4
<211> LENGTH: 337
<212> TYPE: PRT
<213> ORGANISM: Homo sapiens

<400> SEQUENCE: 4

Met Ala Asp Ala Ala Pro Gln Leu Gly Lys Arg Lys Arg Glu Leu Asp
1               5                   10                  15

Val Glu Glu Ala His Ala Ala Ser Thr Glu Glu Lys Glu Ala Gly Val
                20                  25                  30

Gly Asn Gly Thr Cys Ala Pro Val Arg Leu Pro Phe Ser Gly Phe Arg
            35                  40                  45

Leu Gln Lys Val Leu Arg Glu Ser Ala Arg Asp Lys Ile Ile Phe Leu
    50                  55                  60

His Gly Lys Val Asn Glu Ala Ser Gly Asp Gly Asp Gly Glu Asp Ala
65                  70                  75                  80

Val Val Ile Leu Glu Lys Thr Pro Phe Gln Val Glu Gln Val Ala Gln
                85                  90                  95

Leu Leu Thr Gly Ser Pro Glu Leu Gln Leu Gln Phe Ser Asn Asp Ile
            100                 105                 110

Tyr Ser Thr Tyr His Leu Phe Pro Pro Arg Gln Leu Asn Asp Val Lys
    115                 120                 125

Thr Thr Val Val Tyr Pro Ala Thr Glu Lys His Leu Gln Lys Tyr Leu
130                 135                 140

Arg Gln Asp Leu Arg Leu Ile Arg Glu Thr Gly Asp Asp Tyr Arg Asn
145                 150                 155                 160

Ile Thr Leu Pro His Leu Glu Ser Gln Ser Leu Ser Ile Gln Trp Val
                165                 170                 175

Tyr Asn Ile Leu Asp Lys Lys Ala Glu Ala Asp Arg Ile Val Phe Glu
            180                 185                 190

Asn Pro Asp Pro Ser Asp Gly Phe Val Leu Ile Pro Asp Leu Lys Trp
    195                 200                 205

Asn Gln Gln Gln Leu Asp Asp Leu Tyr Leu Ile Ala Ile Cys His Arg
210                 215                 220

Arg Gly Ile Arg Ser Leu Arg Asp Leu Thr Pro Glu His Leu Pro Leu
225                 230                 235                 240

Leu Arg Asn Ile Leu His Gln Gly Gln Glu Ala Ile Leu Gln Arg Tyr
                245                 250                 255

Arg Met Lys Gly Asp His Leu Arg Val Tyr Leu His Tyr Leu Pro Ser
            260                 265                 270

Tyr Tyr His Leu His Val His Phe Thr Ala Leu Gly Phe Glu Ala Pro
    275                 280                 285

Gly Ser Gly Val Glu Arg Ala His Leu Leu Ala Glu Val Ile Glu Asn
290                 295                 300
```

```
Leu Glu Cys Asp Pro Arg His Tyr Gln Gln Arg Thr Leu Thr Phe Ala
305                 310                 315                 320

Leu Arg Ala Asp Pro Leu Leu Lys Leu Leu Gln Glu Ala Gln Gln
            325                 330                 335

Ser

<210> SEQ ID NO 5
<211> LENGTH: 338
<212> TYPE: PRT
<213> ORGANISM: Mus musculus

<400> SEQUENCE: 5

Met Ala Asp Thr Ala Pro Gln Leu Lys Arg Lys Arg Glu Gln Glu Ala
1               5                   10                  15

Glu Glu Ala Glu Thr Pro Ser Thr Glu Glu Lys Glu Ala Gly Val Gly
            20                  25                  30

Asn Gly Thr Ser Ala Pro Val Arg Leu Pro Phe Ser Gly Phe Arg Val
        35                  40                  45

Gln Lys Val Leu Arg Glu Ser Ala Arg Asp Lys Ile Ile Phe Leu His
    50                  55                  60

Gly Lys Val Asn Glu Asp Ser Gly Asp Thr His Gly Asp Ala Val
65                  70                  75                  80

Val Ile Leu Glu Lys Thr Pro Phe Gln Val Glu His Val Ala Gln Leu
                85                  90                  95

Leu Thr Gly Ser Pro Glu Leu Lys Leu Gln Phe Ser Asn Asp Ile Tyr
            100                 105                 110

Ser Thr Tyr Asn Leu Phe Pro Pro Arg His Leu Ser Asp Ile Lys Thr
        115                 120                 125

Thr Val Val Tyr Pro Ala Thr Glu Lys His Leu Gln Lys Tyr Met Arg
130                 135                 140

Gln Asp Leu Arg Leu Ile Arg Glu Thr Gly Asp Asp Tyr Arg Thr Ile
145                 150                 155                 160

Thr Leu Pro Tyr Leu Glu Ser Gln Ser Leu Ser Ile Gln Trp Val Tyr
                165                 170                 175

Asn Ile Leu Asp Lys Lys Ala Glu Ala Asp Arg Ile Val Phe Glu Asn
            180                 185                 190

Pro Asp Pro Ser Asp Gly Phe Val Leu Ile Pro Asp Leu Lys Trp Asn
        195                 200                 205

Gln Gln Gln Leu Asp Asp Leu Tyr Leu Ile Ala Ile Cys His Arg Arg
    210                 215                 220

Gly Ile Arg Ser Leu Arg Asp Leu Thr Pro Glu His Leu Pro Leu Leu
225                 230                 235                 240

Arg Asn Ile Leu Arg Glu Gly Gln Glu Ala Ile Leu Lys Arg Tyr Gln
                245                 250                 255

Val Thr Gly Asp Arg Leu Arg Val Tyr Leu His Tyr Leu Pro Ser Tyr
            260                 265                 270

Tyr His Leu His Val His Phe Thr Ala Leu Gly Phe Glu Ala Pro Gly
        275                 280                 285

Ser Gly Val Glu Arg Ala His Leu Leu Ala Gln Val Ile Glu Asn Leu
    290                 295                 300

Glu Cys Asp Pro Lys His Tyr Gln Gln Arg Thr Leu Thr Phe Ala Leu
305                 310                 315                 320

Arg Thr Asp Asp Pro Leu Leu Gln Leu Leu Gln Lys Ala Gln Gln Glu
                325                 330                 335
```

Arg Asn

<210> SEQ ID NO 6
<211> LENGTH: 337
<212> TYPE: PRT
<213> ORGANISM: Sus scrofa

<400> SEQUENCE: 6

```
Met Ala Asp Thr Ala Pro Gln Pro Ser Lys Arg Lys Arg Glu Arg Asp
1               5                   10                  15

Pro Glu Glu Ala Glu Ala Pro Ser Thr Glu Glu Lys Glu Ala Arg Val
            20                  25                  30

Gly Asn Gly Thr Ser Ala Pro Val Arg Leu Pro Phe Ser Gly Phe Arg
        35                  40                  45

Val Lys Lys Val Leu Arg Glu Ser Ala Arg Asp Lys Ile Ile Phe Leu
    50                  55                  60

His Gly Lys Val Asn Glu Ala Ser Gly Asp Gly Asp Gly Asp Ala
65                  70                  75                  80

Ile Val Ile Leu Glu Lys Thr Pro Phe Gln Val Asp Gln Val Ala Gln
                85                  90                  95

Leu Leu Met Gly Ser Pro Glu Leu Gln Leu Gln Phe Ser Asn Asp Ile
            100                 105                 110

Tyr Ser Thr Tyr His Leu Phe Pro Pro Arg Gln Leu Ser Asp Val Lys
        115                 120                 125

Thr Thr Val Val Tyr Pro Ala Thr Glu Lys His Leu Gln Lys Tyr Leu
    130                 135                 140

His Gln Asp Leu His Leu Val Arg Glu Thr Gly Gly Asp Tyr Lys Asn
145                 150                 155                 160

Ile Thr Leu Pro His Leu Glu Ser Gln Ser Leu Ser Ile Gln Trp Val
                165                 170                 175

Tyr Asn Ile Leu Asp Lys Lys Ala Glu Ala Asp Arg Ile Val Phe Glu
            180                 185                 190

Asn Pro Asp Pro Ser Asp Gly Phe Val Leu Ile Pro Asp Leu Lys Trp
        195                 200                 205

Asn Gln Lys Gln Leu Asp Asp Leu Tyr Leu Ile Ala Ile Cys His Arg
    210                 215                 220

Arg Gly Ile Lys Ser Leu Arg Asp Leu Thr Pro Glu His Leu Pro Leu
225                 230                 235                 240

Leu Arg Asn Ile Leu Arg Glu Gly Gln Glu Ala Ile Leu Gln Arg Tyr
                245                 250                 255

Gln Val Thr Gly Asp Arg Leu Arg Val Tyr Leu His Tyr Leu Pro Ser
            260                 265                 270

Tyr Tyr His Leu His Val His Phe Thr Ala Leu Gly Phe Glu Ala Pro
        275                 280                 285

Gly Ala Gly Val Glu Arg Ala His Leu Leu Ala Glu Val Ile Glu Asn
    290                 295                 300

Leu Glu Gln Asp Pro Glu His Tyr Gln Arg Arg Thr Leu Thr Phe Ala
305                 310                 315                 320

Leu Arg Ala Asp Asp Pro Leu Leu Thr Leu Gln Glu Ala Gln Arg
                325                 330                 335

Ser
```

<210> SEQ ID NO 7
<211> LENGTH: 336
<212> TYPE: PRT

<213> ORGANISM: Rattus norvegicus

<400> SEQUENCE: 7

Met Ala Asp Thr Ala Pro Gln Leu Lys Arg Lys Arg Glu Gln Glu Ala
1               5                   10                  15

Glu Glu Ala Glu Thr Pro Ser Thr Glu Glu Lys Glu Ala Gly Val Gly
            20                  25                  30

Asn Gly Thr Ser Ala Pro Val Arg Leu Pro Phe Ser Gly Phe Arg Val
        35                  40                  45

Gln Lys Val Leu Arg Glu Ser Ala Arg Asp Lys Ile Ile Phe Leu His
    50                  55                  60

Gly Lys Val Asn Glu Asp Ser Gly Asp Thr His Gly Glu Asp Ala Val
65                  70                  75                  80

Val Ile Leu Glu Lys Thr Pro Phe Gln Val Glu His Val Ala Gln Leu
                85                  90                  95

Leu Thr Gly Asn Pro Glu Leu Lys Leu Gln Phe Ser Asn Asp Ile Tyr
            100                 105                 110

Ser Thr Tyr Asn Leu Phe Pro Pro Arg His Leu Ser Asp Ile Lys Thr
        115                 120                 125

Thr Val Val Tyr Pro Ala Ser Glu Lys His Leu Gln Lys Tyr Met Arg
    130                 135                 140

Gln Asp Leu Arg Leu Ile Arg Glu Thr Gly Asp Asp Tyr Arg Ser Leu
145                 150                 155                 160

Thr Leu Pro Tyr Leu Glu Ser Gln Ser Leu Ser Ile Gln Trp Val Tyr
                165                 170                 175

Asn Ile Leu Asp Lys Lys Ala Glu Ala Asp Arg Ile Val Phe Glu Asn
            180                 185                 190

Pro Asp Pro Ser Asp Gly Phe Val Leu Ile Pro Asp Leu Lys Trp Asn
        195                 200                 205

Gln Gln Gln Leu Asp Asp Leu Tyr Leu Ile Ala Ile Cys His Arg Arg
    210                 215                 220

Gly Ile Arg Ser Leu Arg Asp Leu Thr Pro Glu His Leu Pro Leu Leu
225                 230                 235                 240

Arg Asn Ile Leu Arg Glu Gly Gln Glu Ala Ile Leu Lys Arg Tyr Gln
                245                 250                 255

Val Thr Gly Asp Arg Leu Arg Val Tyr Leu His Tyr Leu Pro Ser Tyr
            260                 265                 270

Tyr His Leu His Val His Phe Thr Ala Leu Gly Phe Glu Ala Pro Gly
        275                 280                 285

Ser Gly Val Glu Arg Ala His Leu Leu Ala Glu Val Ile Glu Asn Leu
    290                 295                 300

Glu Cys Asp Pro Lys His Tyr Gln Arg Arg Thr Leu Thr Phe Ala Leu
305                 310                 315                 320

Arg Thr Asp Asp Pro Leu Leu Gln Leu Leu Lys Ala Gln Gln Pro
                325                 330                 335

<210> SEQ ID NO 8
<211> LENGTH: 304
<212> TYPE: PRT
<213> ORGANISM: Schizosaccharomyces pombe

<400> SEQUENCE: 8

Met Glu Glu Ser Ser Ala Ala Lys Ile Gln Leu Leu Lys Glu Phe Lys
1               5                   10                  15

Phe Glu Lys Ile Leu Lys Asp Asp Thr Lys Ser Lys Ile Ile Thr Leu

```
                     20                  25                  30
Tyr Gly Lys Ile Arg Asn Glu Val Ala Leu Leu Leu Glu Lys Thr
             35                  40                  45

Ala Phe Asp Leu Asn Thr Ile Lys Leu Asp Gln Leu Ala Thr Phe Leu
 50                  55                  60

Gln Asp Thr Lys Leu Val Glu Asn Asn Asp Val Phe His Trp Phe Leu
 65                  70                  75                  80

Ser Thr Asn Phe Gln Asp Cys Ser Thr Leu Pro Ser Val Lys Ser Thr
                 85                  90                  95

Leu Ile Trp Pro Ala Ser Glu Thr His Val Arg Lys Tyr Ser Ser Gln
                100                 105                 110

Lys Lys Arg Met Val Cys Glu Thr Pro Glu Met Tyr Leu Lys Val Thr
                115                 120                 125

Lys Pro Phe Ile Glu Thr Gln Arg Gly Pro Gln Ile Gln Trp Val Glu
                130                 135                 140

Asn Ile Leu Thr His Lys Ala Glu Ala Glu Arg Ile Val Val Glu Asp
145                 150                 155                 160

Pro Asp Pro Leu Asn Gly Phe Ile Val Ile Pro Asp Leu Lys Trp Asp
                165                 170                 175

Arg Gln Thr Met Ser Ala Leu Asn Leu Met Ala Ile Val His Ala Thr
                180                 185                 190

Asp Ile Ala Ser Ile Arg Asp Leu Lys Tyr Lys His Ile Pro Leu Leu
                195                 200                 205

Glu Asn Ile Arg Asn Lys Val Leu Thr Glu Val Pro Lys Gln Phe Ser
                210                 215                 220

Val Asp Lys Asn Gln Leu Lys Met Phe Val His Tyr Leu Pro Ser Tyr
225                 230                 235                 240

Tyr His Leu His Val His Ile Leu His Val Asp His Glu Thr Gly Asp
                245                 250                 255

Gly Ser Ala Val Gly Arg Ala Ile Leu Leu Asp Asp Val Ile Asp Arg
                260                 265                 270

Leu Arg Asn Ser Pro Asp Gly Leu Glu Asn Val Asn Ile Thr Phe Asn
                275                 280                 285

Ile Gly Glu Gln His Phe Leu Phe Gln Pro Leu Thr Asn Met Asn Ala
                290                 295                 300
```

<210> SEQ ID NO 9
<211> LENGTH: 350
<212> TYPE: PRT
<213> ORGANISM: Saccharomyces cerevisiae

<400> SEQUENCE: 9

```
Met Ser Gln Leu Pro Thr Asp Phe Ala Ser Leu Ile Lys Arg Phe Gln
 1               5                  10                  15

Phe Val Ser Val Leu Asp Ser Asn Pro Gln Thr Lys Val Met Ser Leu
                 20                  25                  30

Leu Gly Thr Ile Asp Asn Lys Asp Ala Ile Ile Thr Ala Glu Lys Thr
             35                  40                  45

His Phe Leu Phe Asp Glu Thr Val Arg Arg Pro Ser Gln Asp Gly Arg
 50                  55                  60

Ser Thr Pro Val Leu Tyr Asn Cys Glu Asn Glu Tyr Ser Cys Ile Asn
 65                  70                  75                  80

Gly Ile Gln Glu Leu Lys Glu Ile Thr Ser Asn Asp Ile Tyr Tyr Trp
                 85                  90                  95
```

Gly Leu Ser Val Ile Lys Gln Asp Met Glu Ser Asn Pro Thr Ala Lys
            100                 105                 110

Leu Asn Leu Ile Trp Pro Ala Thr Pro Ile His Ile Lys Lys Tyr Glu
        115                 120                 125

Gln Gln Asn Phe His Leu Val Arg Glu Thr Pro Glu Met Tyr Lys Arg
    130                 135                 140

Ile Val Gln Pro Tyr Ile Glu Glu Met Cys Asn Asn Gly Arg Leu Lys
145                 150                 155                 160

Trp Val Asn Asn Ile Leu Tyr Glu Gly Ala Glu Ser Glu Arg Val Val
                165                 170                 175

Tyr Lys Asp Phe Ser Glu Glu Asn Lys Asp Asp Gly Phe Leu Ile Leu
            180                 185                 190

Pro Asp Met Lys Trp Asp Gly Met Asn Leu Asp Ser Leu Tyr Leu Val
        195                 200                 205

Ala Ile Val Tyr Arg Thr Asp Ile Lys Thr Ile Arg Asp Leu Arg Tyr
    210                 215                 220

Ser Asp Arg Gln Trp Leu Ile Asn Leu Asn Asn Lys Ile Arg Ser Ile
225                 230                 235                 240

Val Pro Gly Cys Tyr Asn Tyr Ala Val His Pro Asp Glu Leu Arg Ile
                245                 250                 255

Leu Val His Tyr Gln Pro Ser Tyr Tyr His Phe His Ile His Ile Val
            260                 265                 270

Asn Ile Lys His Pro Gly Leu Gly Asn Ser Ile Ala Ala Gly Lys Ala
        275                 280                 285

Ile Leu Leu Glu Asp Ile Ile Glu Met Leu Asn Tyr Leu Gly Pro Glu
    290                 295                 300

Gly Tyr Met Asn Lys Thr Ile Thr Tyr Ala Ile Gly Glu Asn His Asp
305                 310                 315                 320

Leu Trp Lys Arg Gly Leu Glu Glu Leu Thr Lys Gln Leu Glu Arg
                325                 330                 335

Asp Gly Ile Pro Lys Ile Pro Lys Ile Val Asn Gly Phe Lys
            340                 345                 350

<210> SEQ ID NO 10
<211> LENGTH: 353
<212> TYPE: PRT
<213> ORGANISM: Saccharomyces cerevisiae

<400> SEQUENCE: 10

Met Gly Ser Gln Asp Leu Ala Ser Leu Ile Gly Arg Phe Lys Tyr Val
1               5                   10                  15

Arg Val Leu Asp Ser Asn Pro His Thr Lys Val Ile Ser Leu Leu Gly
            20                  25                  30

Ser Ile Asp Gly Lys Asp Ala Val Leu Thr Ala Glu Lys Thr His Phe
        35                  40                  45

Ile Phe Asp Glu Thr Val Arg Arg Pro Ser Gln Ser Gly Arg Ser Thr
    50                  55                  60

Pro Ile Phe Phe His Arg Glu Ile Asp Glu Tyr Ser Phe Leu Asn Gly
65                  70                  75                  80

Ile Thr Asp Leu Lys Glu Leu Ser Asn Asp Ile Tyr Tyr Trp Gly
                85                  90                  95

Leu Ser Val Leu Lys Gln His Ile Leu His Asn Pro Thr Ala Lys Val
            100                 105                 110

Asn Leu Ile Trp Pro Ala Ser Gln Phe His Ile Lys Gly Tyr Asp Gln
        115                 120                 125

```
Gln Asp Leu His Val Val Arg Glu Thr Pro Asp Met Tyr Arg Asn Ile
            130                 135                 140

Val Val Pro Phe Ile Gln Glu Met Cys Thr Ser Glu Arg Met Lys Trp
145                 150                 155                 160

Val Asn Asn Ile Leu Tyr Glu Gly Ala Glu Asp Asp Arg Val Val Tyr
                165                 170                 175

Lys Glu Tyr Ser Ser Arg Asn Lys Glu Asp Gly Phe Val Ile Leu Pro
            180                 185                 190

Asp Met Lys Trp Asp Gly Ile Asn Ile Asp Ser Leu Tyr Leu Val Ala
        195                 200                 205

Ile Val Tyr Arg Asp Asp Ile Lys Ser Leu Arg Asp Leu Asn Pro Asn
210                 215                 220

His Arg Asp Trp Leu Ile Arg Leu Asn Lys Lys Ile Lys Thr Ile Ile
225                 230                 235                 240

Pro Gln His Tyr Asp Tyr Asn Val Asn Pro Asp Glu Leu Arg Val Phe
                245                 250                 255

Ile His Tyr Gln Pro Ser Tyr Tyr His Phe His Val His Ile Val Asn
            260                 265                 270

Ile Arg His Pro Gly Val Gly Glu Glu Arg Gly Ser Gly Met Thr Ile
        275                 280                 285

Leu Leu Glu Asp Val Ile Glu Ala Leu Gly Phe Leu Gly Pro Glu Gly
    290                 295                 300

Tyr Met Lys Lys Thr Leu Thr Tyr Val Ile Gly Glu Asn His Asp Leu
305                 310                 315                 320

Trp Lys Lys Gly Phe Lys Glu Val Glu Lys Gln Leu Lys His Asp
                325                 330                 335

Gly Ile Ala Thr Ser Pro Glu Lys Gly Ser Gly Phe Asn Thr Asn Leu
            340                 345                 350

Gly

<210> SEQ ID NO 11
<211> LENGTH: 232
<212> TYPE: PRT
<213> ORGANISM: Schizosaccharomyces pombe

<400> SEQUENCE: 11

Met Ser Val His Lys Thr Asn Asp Ala Phe Lys Val Leu Met Asn Ser
1               5                   10                  15

Ala Lys Glu Pro Ile Val Glu Asp Ile Pro Lys Lys Tyr Arg Lys Gln
            20                  25                  30

Ser Phe Arg Asp Asn Leu Lys Val Tyr Ile Glu Ser Pro Glu Ser Tyr
        35                  40                  45

Lys Asn Val Ile Tyr Tyr Asp Asp Val Val Leu Val Arg Asp Met
50                  55                  60

Phe Pro Lys Ser Lys Met His Leu Leu Met Thr Arg Asp Pro His
65                  70                  75                  80

Leu Thr His Val His Pro Leu Glu Ile Met Met Lys His Arg Ser Leu
                85                  90                  95

Val Glu Lys Leu Val Ser Tyr Val Gln Gly Asp Leu Ser Gly Leu Ile
            100                 105                 110

Phe Asp Glu Ala Arg Asn Cys Leu Ser Gln Gln Leu Thr Asn Glu Ala
        115                 120                 125

Leu Cys Asn Tyr Ile Lys Val Gly Phe His Ala Gly Pro Ser Met Asn
    130                 135                 140
```

```
Asn Leu His Leu His Ile Met Thr Leu Asp His Val Ser Pro Ser Leu
145                 150                 155                 160

Lys Asn Ser Ala His Tyr Ile Ser Phe Thr Ser Pro Phe Phe Val Lys
                165                 170                 175

Ile Asp Thr Pro Thr Ser Asn Leu Pro Thr Arg Gly Thr Leu Thr Ser
            180                 185                 190

Leu Phe Gln Glu Asp Leu Lys Cys Trp Arg Cys Gly Glu Thr Phe Gly
        195                 200                 205

Arg His Phe Thr Lys Leu Lys Ala His Leu Gln Glu Glu Tyr Asp Asp
    210                 215                 220

Trp Leu Asp Lys Ser Val Ser Met
225                 230
```

<210> SEQ ID NO 12
<211> LENGTH: 217
<212> TYPE: PRT
<213> ORGANISM: Saccharomyces cerevisiae

<400> SEQUENCE: 12

```
Met Ser Trp Arg Tyr Ala Leu Lys Asn Tyr Val Thr Ser Pro Glu Thr
1               5                   10                  15

Val Asn Asp Asp Thr Val Thr Tyr Phe Asp Lys Val Ser Ile Ile
            20                  25                  30

Arg Asp Ser Phe Pro Lys Ser Glu Cys His Leu Leu Ile Leu Pro Arg
        35                  40                  45

Thr Met Gln Leu Ser Arg Ser His Pro Thr Lys Val Ile Asp Ala Lys
    50                  55                  60

Phe Lys Asn Glu Phe Glu Ser Tyr Val Asn Ser Ala Ile Asp His Ile
65                  70                  75                  80

Phe Arg His Phe Gln Glu Lys Phe Arg Ile Lys Lys Ser Asp Asp
                85                  90                  95

Lys Asp Pro Cys Trp Asp Asp Ile Leu Lys Asp Lys Asn Lys Phe Val
            100                 105                 110

Arg Asn Phe Val Gln Val Gly Ile His Ser Val Pro Ser Met Ala Asn
        115                 120                 125

Leu His Ile His Val Ile Ser Lys Asp Phe His Ser Val Arg Leu Lys
    130                 135                 140

Asn Lys Lys His Tyr Asn Ser Phe Asn Thr Gly Phe Phe Ile Ser Trp
145                 150                 155                 160

Asp Asp Leu Pro Leu Asn Gly Lys Asn Leu Gly Thr Asp Lys Glu Ile
                165                 170                 175

Glu Thr Thr Tyr Leu Lys Glu His Asp Leu Leu Cys Cys Tyr Cys Gln
            180                 185                 190

Arg Asn Phe Ser Asn Lys Phe Ser Leu Leu Lys His Leu Glu Leu
        195                 200                 205

Glu Phe Asn Ser His Phe Glu Leu Lys
    210                 215
```

<210> SEQ ID NO 13
<211> LENGTH: 380
<212> TYPE: PRT
<213> ORGANISM: Ciona intestinalis

<400> SEQUENCE: 13

```
Met Arg Ile Leu Tyr Arg Leu Leu Lys Met Ala Asp Asp Thr Val Lys
1               5                   10                  15
```

Cys Tyr Leu Glu Cys Cys Lys Ser Ser His Pro Lys Leu Pro Leu Pro
                20                  25                  30

His Asn Val Pro Val Ile Ile Gly Arg Thr Pro Glu Leu Gly Ile Thr
             35                  40                  45

Asp Lys Leu Cys Ser Arg Ser Gln Leu Glu Leu Thr Ser Asn Cys Tyr
 50                  55                  60

Lys Arg Tyr Val Leu Val Lys Arg Leu Gly Ala Asn Thr Ser Gln Ile
 65                  70                  75                  80

Asn Gly Ile Asp Ile Glu Lys Asn Lys Ser Ser Arg Leu Glu Glu Gly
                 85                  90                  95

Gln Asp Leu His Val Val Asn Gly Lys Phe Pro His Arg Val Tyr Phe
                100                 105                 110

Thr Gly Cys Gln Asn Asp Thr Lys Thr Glu Lys Ala Val Val Pro Lys
            115                 120                 125

Leu Pro Thr Lys Ser Thr Asp Leu Thr Lys Ser Asp Leu Ser Ile Lys
130                 135                 140

Gln Pro Glu Arg Lys Lys Leu Lys Val Ser Glu Asn Lys Ser Lys Val
145                 150                 155                 160

Leu Asn Ser Lys Ile Lys Pro Gln Glu Lys Phe Ser Ser Glu Ser Val
                165                 170                 175

Tyr Ala Phe Asp Ser Pro Ser Pro Met Ser Ser Arg Cys Glu Lys Lys
            180                 185                 190

Ala Glu Ser Asn Lys Arg Ala Pro Thr His Lys His Trp Ser Gln Gly
            195                 200                 205

Leu Lys Ala Ser Met Glu Asp Pro Glu Leu Val Val Lys Glu Asp Glu
210                 215                 220

Gln Ile Val Val Ile Lys Asp Lys Tyr Pro Lys Ala Lys Tyr His Trp
225                 230                 235                 240

Leu Ile Leu Pro Lys Asp Ser Ile Ser Ser Thr Lys Asn Leu Ser Thr
                245                 250                 255

Asp Asn Ile Glu Leu Leu Lys His Ile Leu Lys Val Gly Gln Glu Leu
            260                 265                 270

Ala Ala Glu Val Lys Asp Lys Gln Pro Asp Val Glu Phe Arg Phe Gly
            275                 280                 285

Tyr His Ala Val Ala Ser Met Ser Gln Met His Met His Val Ile Ser
290                 295                 300

Gln Asp Phe Gln Ser Ser Ser Phe Lys Thr Lys Lys His Trp Asn Ser
305                 310                 315                 320

Phe Thr Thr Asp Tyr Phe Val Asp Ala Thr Asp Ile Ile Asn Glu Leu
                325                 330                 335

Glu Thr Gly Gly Lys Val Lys Asp Arg Arg Thr Met Thr Ser Leu Leu
            340                 345                 350

Asn Glu Pro Leu Lys Cys His Arg Cys Lys Lys Pro Gln Lys Asn Ile
            355                 360                 365

Pro Thr Leu Lys Lys His Ile Asp Ser Cys Gln Lys
370                 375                 380

<210> SEQ ID NO 14
<211> LENGTH: 324
<212> TYPE: PRT
<213> ORGANISM: Danio rerio

<400> SEQUENCE: 14

Met Pro Val Cys Leu Leu Val Ser Glu Asp Asn Ser His Lys Pro Ile

```
            1               5                  10                 15
        Glu Leu His His Gln Gln Ser Val Thr Leu Gly Arg Gly Pro Asp Thr
                         20                  25                 30

Lys Ile Lys Asp Lys Lys Cys Ser Arg Glu Gln Val Glu Leu Arg Ala
                         35                  40                  45

Asp Cys Asn Arg Gly Phe Val Thr Val Lys Gln Leu Gly Val Asn Pro
                     50                  55                  60

Thr Leu Val Asp Asp Val Val Gly Lys Gly Asn Gln Val Ser Ile
         65                  70                  75                  80

Lys Pro Gly Gln Ser Leu Tyr Met Val Asn Gln Gln Tyr Pro Tyr Ser
                             85                  90                  95

Val Lys Phe Thr Glu Asp Thr Ser Arg Ser Lys Pro Ser Lys Arg Ala
                        100                 105                 110

Gln Gln Ile Gln Ser Pro Thr Lys Thr Thr Ala Asp Val Ser Asp Ser
                        115                 120                 125

Pro Pro Pro Pro Lys Lys Thr Thr Pro Pro Ala Gly Glu Lys Ser Glu
                    130                 135                 140

Ser Ala Gly His Trp Ser Gln Gly Leu Lys Ala Ser Met Gln Asp Pro
        145                 150                 155                 160

Lys Met Gln Val Tyr Lys Asp Asp Ser Val Val Ile Lys Asp Lys
                            165                 170                 175

Tyr Pro Lys Ala Arg Tyr His Trp Leu Val Leu Pro Trp Gln Ser Ile
                        180                 185                 190

Ser Ser Leu Lys Ala Leu Arg Ser Glu His Val Glu Leu Leu Lys His
                    195                 200                 205

Met Gln Arg Val Ala Asp Gln Met Val Glu Gln Cys Pro Asp Ala His
                    210                 215                 220

Lys Leu Ser Phe Arg Leu Gly Tyr His Ala Ile Pro Ser Met Ser His
        225                 230                 235                 240

Val His Leu His Val Ile Ser Gln Asp Phe Asp Ser Pro Cys Leu Lys
                            245                 250                 255

Asn Lys Lys His Trp Asn Ser Phe Thr Thr Asp Tyr Phe Val Glu Ser
                        260                 265                 270

Gln Asp Val Ile Ser Met Leu Glu His Asp Gly Lys Val Gln Val Lys
                    275                 280                 285

Glu Gly Ala Gly Glu Leu Leu Lys Leu Pro Leu Arg Cys His Val Cys
                    290                 295                 300

Gly Lys Glu Gln Thr Thr Ile Pro Lys Leu Lys Asp His Leu Lys Thr
        305                 310                 315                 320

His Leu Pro Ser

<210> SEQ ID NO 15
        <211> LENGTH: 356
        <212> TYPE: PRT
        <213> ORGANISM: Takifugu rubripes

<400> SEQUENCE: 15

Met Pro Leu Cys Trp Leu Ile Ser Val Glu Gly Asn His Lys Pro Ile
        1               5                  10                  15

Leu Leu Pro His Leu Gln Ala Val Val Leu Gly Arg Gly Pro Glu Thr
                            20                  25                  30

Thr Ile Lys Asp Lys Lys Cys Ser Arg Glu Gln Val Glu Leu Gln Ala
                        35                  40                  45

Glu Cys Asn Lys Gly Tyr Val Lys Val Lys Gln Leu Gly Leu Asn Pro
```

Thr Ser Ile Asp Ser Leu Val Gly Lys Gly Ser Val Ser Lys Met
65                  70                  75                  80

Lys Pro Gly Gln Gln Leu Tyr Ile Val Asn Gln Leu Tyr Pro Tyr Thr
                85                  90                  95

Val Gln Phe Lys Glu Asp Leu Ser Gly Ser Thr Lys Arg Ser Arg Glu
            100                 105                 110

Ala Val Ser Glu Thr Arg His Asn Asp Lys Glu Glu Pro Cys Arg Lys
            115                 120                 125

Ser Ser Lys Gln Gly Glu Val Ser Val Ser Val Ser Gln Lys Glu Ala
            130                 135                 140

Pro Lys Met Ser Val Arg Ser Asn Val His Phe Ser Leu Leu Ser Ile
145                 150                 155                 160

Leu Leu Ser Gly Leu Leu Ser Glu Gly Val Gly Lys Met Leu Gln Gly
                165                 170                 175

Ser Val Gly His Trp Asn Leu Gly Leu Lys Ala Ser Met Gln Asp Pro
                180                 185                 190

Glu Met Gln Val Tyr Lys Asp Asp Lys Val Val Ile Lys Asp Lys
            195                 200                 205

Tyr Pro Lys Ala Arg Tyr His Trp Leu Val Leu Pro Trp Gln Ser Ile
210                 215                 220

Ser Ser Leu Lys Ala Leu Arg Lys Glu His Cys Asp Leu Val Lys His
225                 230                 235                 240

Met Gln Gln Val Ala Glu Gln Met Ile Arg Gln Cys Pro Asp Ala Ser
            245                 250                 255

Thr Pro Arg Phe Arg Ser Gly Tyr His Ala Ile Pro Ser Met Ser His
            260                 265                 270

Val His Leu His Val Ile Ser Gln Asp Phe Asp Ser Pro Cys Leu Lys
            275                 280                 285

Asn Lys Lys His Trp Asn Ser Phe Thr Thr Asp Tyr Phe Ile Glu Ser
            290                 295                 300

Gln Ala Val Ile Gln Met Leu Glu Thr Asp Gly Ser Ile Ser Ile Lys
305                 310                 315                 320

Glu Gly Ala Thr Glu Leu Leu Lys Leu Pro Leu Arg Cys His Val Cys
                325                 330                 335

Arg Lys Glu Phe Ser Asn Ile Pro Ala Leu Lys Gln His Leu Asn Ser
            340                 345                 350

His Phe Pro Ser
        355

<210> SEQ ID NO 16
<211> LENGTH: 347
<212> TYPE: PRT
<213> ORGANISM: Xenopus laevis

<400> SEQUENCE: 16

Met Phe Glu Cys Trp Leu Val Ser Lys Asp Gly Lys His Gly Arg Ile
1               5                   10                  15

Arg Leu Pro His Ala Glu Thr Val Val Ile Gly Arg Gly Pro Glu Thr
            20                  25                  30

Gln Ile Thr Asp Lys Lys Cys Ser Arg His Gln Val Gln Leu Met Ala
            35                  40                  45

Asp Cys Asn Lys Gly Tyr Val Leu Val Lys Gln Met Gly Thr Asn Pro
50                  55                  60

Thr Ser Ile Asn Gly Val Asp Ile Gly Asn Glu His Lys Val Glu Leu
 65                  70                  75                  80

Lys Pro Gly His Thr Leu Tyr Ile Val Asn Asn Leu Tyr Pro Tyr Met
                 85                  90                  95

Ile Glu Phe Leu Glu Gly Ser Thr Asn Pro Arg Ala Lys Ile Glu Asn
            100                 105                 110

Glu Asn Arg Ser Ser Ser Lys Arg Thr Pro Glu Asn Ser Leu Asn Val
        115                 120                 125

Asp Thr Glu Thr Pro Arg Lys Leu Val Lys Lys Glu Ser Asn Val Ser
130                 135                 140

Pro Ser Ser Ser Gly Arg Ile Ser Ser Cys Pro Thr Gln Gly Lys
145                 150                 155                 160

Ser Asn Val Gln Glu Val Lys Ser Gln Gly His Trp Ser Gln Asp Leu
                165                 170                 175

Lys Val Ser Met Gln Asp Pro Thr Met Gln Val Phe Lys Asp Asp Lys
            180                 185                 190

Ile Val Val Ile Lys Asp Lys Tyr Pro Lys Ala Arg Tyr His Trp Leu
        195                 200                 205

Val Leu Pro Trp Gln Ser Ile Ala Ser Leu Lys Val Leu Arg Ala Glu
210                 215                 220

His Leu Glu Leu Val Gln His Met Asp Ala Val Gly His Asn Ile Ala
225                 230                 235                 240

Arg Glu His Thr Asn Ser Lys Cys Ala Pro Phe Arg Phe Gly Tyr His
                245                 250                 255

Ala Ile Pro Ser Met Ser His Val His Leu His Val Ile Ser Gln Asp
            260                 265                 270

Phe Asp Ser Pro Cys Leu Lys Asn Lys Lys His Trp Asn Ser Phe Thr
        275                 280                 285

Thr Asp Tyr Phe Leu Glu Ser Gln Ala Val Ile Glu Met Leu Lys Thr
290                 295                 300

His Gly Lys Val Asn Val Lys Glu Arg Ile Ser Asp Val Leu Lys Thr
305                 310                 315                 320

Pro Leu Leu Cys His Met Cys Lys Lys Glu Gln Ala Thr Met Pro Gln
                325                 330                 335

Leu Lys Glu His Leu Lys Lys His Trp Pro Thr
            340                 345

<210> SEQ ID NO 17
<211> LENGTH: 347
<212> TYPE: PRT
<213> ORGANISM: Xenopus tropicalis

<400> SEQUENCE: 17

Met Ile Glu Cys Trp Leu Val Ser Lys Asp Gly Lys His Gly Arg Ile
1               5                   10                  15

Arg Leu Pro His Ala Glu Thr Val Val Ile Gly Arg Gly Pro Glu Thr
            20                  25                  30

Gln Ile Thr Asp Lys Lys Cys Ser Arg His Gln Val Gln Leu Met Ala
        35                  40                  45

Asp Cys Asn Lys Gly Tyr Val Lys Val Lys Gln Leu Gly Thr Asn Pro
    50                  55                  60

Thr Ser Ile Asp Gly Val Asp Ile Gly Lys Glu Gln Lys Val Asp Leu
65                  70                  75                  80

Lys Pro Gly His Thr Leu His Ile Val Asn Asn Leu Tyr Pro Tyr Val
                85                  90                  95

```
Ile Glu Phe Leu Glu Gly Ala Thr Asn Pro His Ala Lys Arg Glu Asn
            100                 105                 110

Glu Asn Arg Ser Ser Lys Arg Thr Gln Glu Asn Ser Leu Asn Glu
        115                 120                 125

Gly Thr Gly Thr Ser Met Lys Leu Met Lys Lys Glu Ser Asn Ile Ser
    130                 135                 140

Pro Ser Ser Ser Gly Lys Asn Ser Cys Ser Thr Glu Glu Lys
145                 150                 155                 160

Tyr Asn Ala Gln Glu Val Lys Ser Gln Gly His Trp Ser Gln Gly Leu
                165                 170                 175

Lys Ala Ser Met Gln Asp Pro Thr Met Gln Val Phe Lys Asp Asp Lys
            180                 185                 190

Val Val Val Ile Lys Asp Lys Tyr Pro Lys Ala Arg Tyr His Trp Leu
        195                 200                 205

Val Leu Pro Trp Gln Ser Ile Ala Asn Leu Lys Val Leu Arg Ala Glu
    210                 215                 220

His Leu Glu Leu Val Gln His Met His Ala Val Gly Gln Lys Ile Ala
225                 230                 235                 240

Lys Glu His Ser Asp Ser Lys Cys Ala Pro Phe Gln Leu Gly Tyr His
                245                 250                 255

Ala Ile Pro Ser Met Ser His Val His Leu His Val Ile Ser Gln Asp
            260                 265                 270

Phe Asp Ser Pro Cys Leu Lys Asn Lys Lys His Trp Asn Ser Phe Thr
        275                 280                 285

Thr Asp Tyr Phe Leu Glu Ser Gln Ala Met Ile Glu Met Ile Lys Thr
    290                 295                 300

His Gly Lys Val Asn Val Lys Asp Gly Val Ser Glu Leu Leu Lys Thr
305                 310                 315                 320

Pro Leu Met Cys His Ile Cys Arg Lys Glu Gln Ala Asn Met Pro Gln
                325                 330                 335

Leu Lys Glu His Leu Lys Lys His Trp Pro Thr
            340                 345

<210> SEQ ID NO 18
<211> LENGTH: 316
<212> TYPE: PRT
<213> ORGANISM: Gallus gallus

<400> SEQUENCE: 18

His Ala Ser Ala Arg Gly Glu Gly Phe Leu Leu Leu Lys Ala Asp Cys
1               5                   10                  15

Asn Lys Gly Tyr Val Thr Val Lys Gln Ile Gly Val Asn Pro Thr Ser
            20                  25                  30

Val Asp Leu Val Asp Val Gly Lys Asp Glu Glu Val Lys Met Arg Pro
        35                  40                  45

Gly Gln Val Leu His Ile Val Asn Lys Leu Tyr Pro Phe Val Val Gln
    50                  55                  60

Phe Gly Glu Glu Ser Glu Glu Ser Val Met Gly Ala Glu Glu Lys Ile
65                  70                  75                  80

Gln Thr Glu Lys Arg Pro Cys Glu Asp Ser Cys Glu Asn Asp Asp Ile
                85                  90                  95

Glu Asn Val Pro Lys Lys Ala Lys Lys Met Glu Val Val Asp Thr Gln
            100                 105                 110

Ser Ser Ser Ala Asp Leu Arg Pro Ser Lys Ser Ser Val Ser Pro His
```

```
            115                 120                 125
Glu Gly Thr Thr Ser Arg Lys Glu His Leu Gly His Trp Ser Gln Gly
    130                 135                 140

Leu Lys Ser Ser Met Gln Asp Pro Lys Val Gln Val Tyr Lys Asp Glu
145                 150                 155                 160

Lys Thr Val Val Ile Lys Asp Lys Tyr Pro Lys Ala Arg Tyr His Trp
                165                 170                 175

Leu Val Leu Pro Trp Asp Ser Ile Ser Ser Leu Lys Ser Val Thr Arg
            180                 185                 190

Glu His Leu Gly Leu Leu Glu His Met His Ala Val Gly Gln Lys Met
        195                 200                 205

Ile Gln Gln Cys Pro Ala Lys Glu Ser Leu Glu Phe Arg Leu Gly Tyr
    210                 215                 220

His Ala Ile Pro Ser Met Ser Gln Leu His Leu His Val Ile Ser Gln
225                 230                 235                 240

Asp Phe Asp Ser Pro Ala Leu Lys Thr Lys His Trp Asn Ser Phe
                245                 250                 255

Thr Thr Glu Tyr Phe Leu Asn Ser Glu Glu Val Ile Glu Met Val Arg
                260                 265                 270

Ser Lys Gly Lys Val Thr Val Asn Asp Gln Ala Ser Glu Leu Leu Lys
                275                 280                 285

Leu Pro Leu Arg Cys His Leu Cys Lys Gln Gln Leu Ser Thr Ile Pro
            290                 295                 300

Gln Leu Lys Glu His Leu Lys Lys His Trp Thr Lys
305                 310                 315

<210> SEQ ID NO 19
<211> LENGTH: 342
<212> TYPE: PRT
<213> ORGANISM: Mus musculus

<400> SEQUENCE: 19

Met Pro Glu Ala Val Ala Lys Met Arg Val Cys Trp Leu Val Arg Gln
1               5                   10                  15

Asp Ser Arg His Gln Arg Ile Lys Leu Pro His Leu Glu Ala Val Val
                20                  25                  30

Ile Gly Arg Ser Pro Glu Thr Lys Ile Thr Asp Lys Lys Cys Ser Arg
            35                  40                  45

Gln Gln Val Gln Leu Lys Ala Glu Cys Asn Lys Gly Tyr Val Lys Val
    50                  55                  60

Gln Gln Met Gly Val Asn Pro Thr Ser Ile Asp Ser Gly Val Ile Gly
65                  70                  75                  80

Lys Asp Gln Glu Lys Lys Leu Leu Pro Gly Gln Val Leu His Met Val
                85                  90                  95

Asn Gly Leu Tyr Pro Tyr Ile Val Glu Phe Glu Glu Val Ala Glu Ser
                100                 105                 110

Pro Asn Leu Thr Gln Arg Lys Arg Lys Arg Ser Asp Cys Asp Ser Glu
            115                 120                 125

Glu Met Glu Ala Glu Ser Gly Thr Gly Leu Ala Pro Gly Ser Ser Pro
    130                 135                 140

Ser Gln Cys Ser Val Ser Pro Lys Lys Asp Lys Asn Gly Ala Thr Lys
145                 150                 155                 160

Lys Glu Ser Leu Gly His Trp Ser Gln Gly Leu Lys Met Ser Met Lys
                165                 170                 175
```

```
Asp Pro Lys Met Gln Val Tyr Lys Asp Asp Gln Val Val Ile Lys
            180                 185                 190

Asp Lys Tyr Pro Lys Ala Arg His His Trp Leu Val Leu Pro Trp Ala
            195                 200                 205

Ser Ile Ser Ser Leu Lys Val Val Thr Ser Glu His Leu Glu Leu Leu
    210                 215                 220

Lys His Met His Ala Val Gly Glu Lys Val Ile Ala Asp Phe Ala Gly
225                 230                 235                 240

Ser Ser Lys Leu Arg Phe Arg Leu Gly Tyr His Ala Ile Pro Ser Met
                245                 250                 255

Ser His Val His Leu His Val Ile Ser Gln Asp Phe Asp Ser Pro Cys
            260                 265                 270

Leu Lys Asn Lys Lys His Trp Asn Ser Phe Asn Thr Glu Tyr Phe Leu
        275                 280                 285

Glu Ser Gln Ala Val Ile Lys Met Val Gln Glu Ala Gly Arg Val Thr
    290                 295                 300

Val Lys Asp Gly Thr Cys Glu Leu Leu Lys Leu Pro Leu Arg Cys His
305                 310                 315                 320

Glu Cys Gln Gln Leu Leu Pro Ser Ile Pro Gln Leu Lys Glu His Leu
                325                 330                 335

Arg Lys His Trp Gly Gly
                340

<210> SEQ ID NO 20
<211> LENGTH: 329
<212> TYPE: PRT
<213> ORGANISM: Rattus norvegicus

<400> SEQUENCE: 20

Met Arg Val Cys Trp Leu Val Arg Gln Asp Cys Trp His Gln Arg Ile
1               5                   10                  15

Lys Leu Pro His Leu Glu Ala Val Val Ile Gly Arg Ser Pro Glu Thr
            20                  25                  30

Lys Ile Thr Asp Lys Lys Cys Ser Arg Gln Gln Val Gln Leu Lys Ala
        35                  40                  45

Glu Cys Asn Lys Arg Tyr Val Asn Val Lys Gln Met Gly Val Asn Pro
    50                  55                  60

Thr Ser Ile Asp Glu Val Val Ile Gly Lys Asp Arg Glu Met Lys Leu
65                  70                  75                  80

Leu Pro Gly Gln Val Leu His Met Val Asn Glu Leu Tyr Pro Tyr Met
                85                  90                  95

Val Glu Phe Glu Glu Val Ala Glu Ser Pro Asn Val Thr Gln Arg Lys
            100                 105                 110

Arg Lys Arg Pro Asp Cys Asp Ser Gln Glu Met Glu Ala Glu Ala Gly
        115                 120                 125

Ala Ser Pro Ser Gln Cys Ser Val Ser Pro Lys Thr Gly Lys His Gly
    130                 135                 140

Ala Ala Lys Glu Glu Ser Leu Gly His Trp Ser Gln Gly Leu Lys Ile
145                 150                 155                 160

Ser Met Lys Asp Pro Lys Met Gln Val Tyr Lys Asp Asp Gln Val Val
                165                 170                 175

Val Ile Lys Asp Lys Tyr Pro Lys Ala Arg His His Trp Leu Val Leu
            180                 185                 190

Pro Trp Ala Ser Ile Ser Ser Leu Lys Val Val Thr Ser Glu His Leu
        195                 200                 205
```

Glu Leu Leu Lys His Met His Ala Val Gly Glu Lys Val Ile Ala Asp
210                 215                 220

Phe Thr Gly Ser Ser Lys Leu Arg Phe Arg Leu Gly Tyr His Ala Ile
225                 230                 235                 240

Pro Ser Met Ser His Val His Leu His Val Ile Ser Gln Asp Phe Asp
                245                 250                 255

Ser Pro Cys Leu Lys Asn Lys Lys His Trp Asn Ser Phe Asn Thr Glu
            260                 265                 270

Tyr Phe Leu Glu Ser Gln Ala Val Ile Lys Met Val Gln Glu Ala Gly
        275                 280                 285

Arg Val Thr Val Lys Asp Gly Thr Cys Glu Leu Leu Lys Leu Pro Leu
    290                 295                 300

Arg Cys His Glu Cys Gln Gln Leu Leu Pro Ser Ile Pro Gln Leu Lys
305                 310                 315                 320

Glu His Leu Arg Lys His Trp Gly Gly
                325

<210> SEQ ID NO 21
<211> LENGTH: 342
<212> TYPE: PRT
<213> ORGANISM: Canis lupus familiaris

<400> SEQUENCE: 21

Met Met Arg Met Cys Trp Leu Val Arg Gln Asp Asn Gln His Gln Arg
1               5                   10                  15

Ile Lys Leu Pro His Leu Glu Ala Val Met Val Gly Arg Gly Pro Glu
            20                  25                  30

Thr Lys Ile Ile Asp Lys Lys Cys Ser Arg Gln Gln Val Gln Leu Lys
        35                  40                  45

Ala Glu Cys Asn Lys Gly Tyr Val Lys Val Lys Gln Val Gly Val Asn
    50                  55                  60

Pro Thr Ser Ile Asp Ser Val Ile Ile Gly Lys Asp Gln Glu Ala Lys
65                  70                  75                  80

Leu Gln Pro Gly Gln Val Leu His Met Val Asn Glu Leu Tyr Pro Tyr
                85                  90                  95

Ile Val Glu Phe Glu Glu Ala Glu Ser Pro Gly Leu Glu Thr His
            100                 105                 110

Arg Lys Arg Lys Arg Ser Gly Asn Ser Asp Ser Ile Glu Arg Asp Ala
        115                 120                 125

Ala Gln Glu Ala Glu Ser Ser Thr Gly Leu Glu Pro Gly Ser Asp Ser
    130                 135                 140

Ser Gln Cys Ser Val Pro Leu Asn Lys Gly Lys Asp Ala Pro Thr Lys
145                 150                 155                 160

Lys Glu Ser Leu Gly His Trp Ser Gln Gly Leu Lys Ile Ser Met Gln
                165                 170                 175

Asp Pro Lys Met Gln Val Tyr Lys Asp Glu Gln Val Val Ile Lys
            180                 185                 190

Asp Lys Tyr Pro Lys Ala Arg Tyr His Trp Leu Val Leu Pro Trp Ala
        195                 200                 205

Ser Val Ser Ser Leu Lys Ala Val Thr Gly Glu His Leu Glu Leu Leu
    210                 215                 220

Lys His Met His Thr Val Gly Glu Lys Met Ile Ala Asp Phe Ala Gly
225                 230                 235                 240

Ser Ser Lys Leu Arg Phe Arg Leu Gly Tyr His Ala Ile Pro Ser Met

-continued

```
               245                 250                 255
Ser His Val His Leu His Val Ile Ser Gln Asp Phe Asp Ser Pro Cys
            260                 265                 270
Leu Lys Asn Lys Lys His Trp Asn Ser Phe Asn Thr Glu Tyr Phe Leu
            275                 280                 285
Glu Ser Gln Ala Val Ile Glu Met Val Gln His Ala Gly Arg Val Ser
            290                 295                 300
Val Arg Asp Gly Met Pro Glu Leu Leu Lys Leu Pro Leu Arg Cys His
305                 310                 315                 320
Glu Cys Gln Gln Leu Leu Pro Ser Ile Pro Gln Leu Lys Glu His Leu
            325                 330                 335
Arg Arg His Trp Pro Lys
            340

<210> SEQ ID NO 22
<211> LENGTH: 356
<212> TYPE: PRT
<213> ORGANISM: Homo sapiens

<400> SEQUENCE: 22

Met Ser Asn Val Asn Leu Ser Val Ser Asp Phe Trp Arg Val Met Met
1               5                  10                  15
Arg Val Cys Trp Leu Val Arg Gln Asp Ser Arg His Gln Arg Ile Arg
                20                  25                  30
Leu Pro His Leu Glu Ala Val Val Ile Gly Arg Gly Pro Glu Thr Lys
            35                  40                  45
Ile Thr Asp Lys Lys Cys Ser Arg Gln Gln Val Gln Leu Lys Ala Glu
        50                  55                  60
Cys Asn Lys Gly Tyr Val Lys Val Lys Gln Val Gly Val Asn Pro Thr
65                  70                  75                  80
Ser Ile Asp Ser Val Val Ile Gly Lys Asp Gln Glu Val Lys Leu Gln
                85                  90                  95
Pro Gly Gln Val Leu His Met Val Asn Glu Leu Tyr Pro Tyr Ile Val
            100                 105                 110
Glu Phe Glu Glu Glu Ala Lys Asn Pro Gly Leu Glu Thr His Arg Lys
        115                 120                 125
Arg Lys Arg Ser Gly Asn Ser Asp Ser Ile Glu Arg Asp Ala Ala Gln
130                 135                 140
Glu Ala Glu Ala Gly Thr Gly Leu Glu Pro Gly Ser Asn Ser Gly Gln
145                 150                 155                 160
Cys Ser Val Pro Leu Lys Lys Gly Lys Asp Ala Pro Ile Lys Lys Glu
                165                 170                 175
Ser Leu Gly His Trp Ser Gln Gly Leu Lys Ile Ser Met Gln Asp Pro
            180                 185                 190
Lys Met Gln Val Tyr Lys Asp Glu Gln Val Val Val Ile Lys Asp Lys
        195                 200                 205
Tyr Pro Lys Ala Arg Tyr His Trp Leu Val Leu Pro Trp Thr Ser Ile
    210                 215                 220
Ser Ser Leu Lys Ala Val Ala Arg Glu His Leu Glu Leu Leu Lys His
225                 230                 235                 240
Met His Thr Val Gly Glu Lys Val Ile Val Asp Phe Ala Gly Ser Ser
                245                 250                 255
Lys Leu Arg Phe Arg Leu Gly Tyr His Ala Ile Pro Ser Met Ser His
            260                 265                 270
```

Val His Leu His Val Ile Ser Gln Asp Phe Asp Ser Pro Cys Leu Lys
            275                 280                 285

Asn Lys Lys His Trp Asn Ser Phe Asn Thr Glu Tyr Phe Leu Glu Ser
290                 295                 300

Gln Ala Val Ile Glu Met Val Gln Glu Ala Gly Arg Val Thr Val Arg
305                 310                 315                 320

Asp Gly Met Pro Glu Leu Leu Lys Leu Pro Leu Arg Cys His Glu Cys
                325                 330                 335

Gln Gln Leu Leu Pro Ser Ile Pro Gln Leu Lys Glu His Leu Arg Lys
            340                 345                 350

His Trp Thr Gln
            355

<210> SEQ ID NO 23
<211> LENGTH: 356
<212> TYPE: PRT
<213> ORGANISM: Macaca fascicularis

<400> SEQUENCE: 23

Met Ser Asn Val Asn Leu Ser Val Ser Asp Val Trp Arg Leu Met Met
1               5                   10                  15

Arg Val Cys Trp Leu Val Arg Gln Asp Ser Arg His Gln Arg Ile Arg
            20                  25                  30

Leu Pro His Leu Glu Ala Val Val Ile Gly Arg Gly Pro Glu Thr Lys
        35                  40                  45

Ile Thr Asp Lys Lys Cys Ser Arg Gln Gln Val Gln Leu Lys Ala Glu
    50                  55                  60

Cys Asn Lys Gly Tyr Val Lys Val Lys Gln Val Gly Val Asn Pro Thr
65                  70                  75                  80

Ser Ile Asp Ser Val Val Ile Gly Lys Asp Gln Glu Val Lys Leu Gln
                85                  90                  95

Pro Gly Gln Val Leu His Met Val Asn Glu Leu Tyr Pro Tyr Ile Val
            100                 105                 110

Glu Phe Glu Glu Glu Ala Lys Asn Pro Gly Leu Glu Thr His Arg Lys
        115                 120                 125

Arg Lys Arg Ser Gly Asp Ser Asp Ser Ile Glu Arg Asp Ala Ala His
    130                 135                 140

Glu Ala Glu Pro Gly Thr Gly Leu Glu Pro Gly Ser Asn His Asn Gln
145                 150                 155                 160

Cys Ser Val Pro Pro Lys Lys Gly Lys Asp Ala Pro Ile Lys Lys Glu
                165                 170                 175

Ser Leu Gly His Trp Ser Gln Gly Leu Lys Ile Ser Met Gln Asp Pro
            180                 185                 190

Lys Met Gln Val Tyr Lys Asp Glu Gln Val Val Ile Lys Asp Lys
        195                 200                 205

Tyr Pro Lys Ala Arg Tyr His Trp Leu Val Leu Pro Trp Thr Ala Ile
    210                 215                 220

Ser Ser Leu Lys Ala Val Thr Arg Glu His Leu Glu Leu Leu Lys His
225                 230                 235                 240

Met His Thr Val Gly Glu Lys Val Ile Val Asp Phe Ala Gly Ser Ser
                245                 250                 255

Lys Leu Arg Phe Arg Leu Gly Tyr His Ala Ile Pro Ser Met Ser His
            260                 265                 270

Val His Leu His Val Ile Ser Gln Asp Phe Asp Ser Pro Cys Leu Lys
        275                 280                 285

```
Asn Lys Lys His Trp Asn Ser Phe Asn Thr Glu Tyr Phe Leu Glu Ser
        290                 295                 300

Gln Ala Val Ile Glu Met Val Gln Glu Ala Gly Arg Val Thr Val Arg
305                 310                 315                 320

Asp Gly Met Pro Glu Leu Leu Lys Leu Pro Leu Arg Cys His Glu Cys
                    325                 330                 335

Gln Gln Leu Leu Pro Ser Ile Pro Gln Leu Lys Glu His Leu Arg Lys
            340                 345                 350

His Trp Thr Gln
        355

<210> SEQ ID NO 24
<211> LENGTH: 356
<212> TYPE: PRT
<213> ORGANISM: Bos taurus

<400> SEQUENCE: 24

Met Ser Asn Val Ser Leu Ser Ala Ser Ala Val Ser Arg Val Met Met
1               5                   10                  15

Arg Val Cys Trp Leu Val Arg Gln Asp Asn Arg His Gln Arg Ile Lys
            20                  25                  30

Leu Pro His Leu Glu Thr Val Met Val Gly Arg Ser Pro Glu Thr Lys
        35                  40                  45

Ile Ala Asp Lys Lys Cys Ser Arg Gln Gln Val Gln Leu Lys Ala Glu
    50                  55                  60

Cys Asn Lys Gly Tyr Val Lys Val Lys Gln Val Gly Val Asn Pro Thr
65                  70                  75                  80

Ser Ile Asp Ser Val Ile Ile Gly Lys Asp Gln Glu Val Lys Leu Gln
                    85                  90                  95

Pro Gly Gln Val Leu Tyr Leu Val Asn Glu Leu Tyr Pro Tyr Ile Ile
            100                 105                 110

Glu Phe Glu Glu Glu Thr Lys Ser Pro Gly Leu Glu Ser His Arg Lys
        115                 120                 125

Arg Lys Arg Ser Gly Ser Ser Asp Pro Thr Glu Arg Gly Ala Asp Pro
    130                 135                 140

Glu Ala Glu Pro Ser Thr Gly Leu Glu Pro Gly Ser Asn Pro His Gln
145                 150                 155                 160

Cys Ser Val Pro Pro Lys Lys Glu Lys Asp Ala Ser Ile Lys Lys Glu
                    165                 170                 175

Ser Leu Gly His Trp Ser Gln Gly Leu Lys Ile Ser Met Glu Asp Pro
            180                 185                 190

Lys Met Gln Val Tyr Lys Asp Glu Gln Val Val Val Ile Lys Asp Lys
        195                 200                 205

Tyr Pro Lys Ala Arg Phe His Trp Leu Val Leu Pro Trp Ala Ser Ile
    210                 215                 220

Ser Ser Leu Lys Ala Val Thr Arg Glu His Leu Glu Leu Leu Arg His
225                 230                 235                 240

Met His Ala Val Gly Glu Lys Val Ile Ala Asp Phe Ala Gly Ser Ser
                    245                 250                 255

Lys Phe Arg Phe Arg Leu Gly Tyr His Ala Ile Pro Ser Met Ser His
            260                 265                 270

Val His Leu His Val Ile Ser Gln Asp Phe Asp Ser Pro Cys Leu Lys
        275                 280                 285

Asn Lys Lys His Trp Asn Ser Phe Asn Thr Glu Tyr Phe Leu Glu Ser
```

```
            290                 295                 300
Gln Ala Val Ile Glu Met Val Gln Glu Ala Gly Arg Val Thr Val Arg
305                 310                 315                 320

Asp Gly Met Pro Glu Leu Leu Lys Leu Pro Leu Arg Cys His Glu Cys
                325                 330                 335

Gln Gln Leu Leu Pro Ser Ile Pro Gln Leu Lys Glu His Leu Arg Lys
            340                 345                 350

His Trp Ser Lys
        355

<210> SEQ ID NO 25
<211> LENGTH: 356
<212> TYPE: PRT
<213> ORGANISM: Sus scrofa

<400> SEQUENCE: 25

Met Ser Asn Val Ser Leu Ser Pro Ser Ala Val Ser Arg Ile Met Thr
1               5                   10                  15

Arg Val Cys Trp Leu Val Arg Gln Asp Ser Arg His Gln Arg Ile Lys
            20                  25                  30

Leu Pro His Leu Glu Ala Val Ile Val Gly Arg Gly Pro Glu Thr Lys
        35                  40                  45

Ile Thr Asp Lys Lys Cys Ser Arg Gln Gln Val Gln Leu Lys Ala Glu
    50                  55                  60

Cys Asn Lys Gly Tyr Val Lys Val Lys Gln Val Gly Val Asn Pro Thr
65                  70                  75                  80

Ser Ile Asp Ser Val Ile Ile Gly Lys Asp Gln Glu Met Lys Leu Gln
                85                  90                  95

Pro Gly Gln Val Leu His Met Val Asn Glu Leu Tyr Pro Tyr Val Ile
            100                 105                 110

Glu Phe Glu Glu Glu Ala Lys Ser Pro Gly Leu Lys Thr His Arg Lys
        115                 120                 125

Arg Lys Arg Ser Gly Asn Ser Asp Ser Val Glu Arg Asp Ala Ser Gln
    130                 135                 140

Glu Ala Lys Pro Ser Thr Gly Ala Glu Pro Gly Ser Asn Pro Ser Gln
145                 150                 155                 160

Cys Ser Val Pro Pro Lys Lys Glu Lys Asp Ala Ala Thr Lys Lys Glu
                165                 170                 175

Ser Leu Ser His Trp Ser Gln Gly Leu Lys Ile Ser Met Glu Asp Pro
            180                 185                 190

Lys Met Gln Val Tyr Lys Asp Asp Gln Val Val Ile Lys Asp Lys
        195                 200                 205

Tyr Pro Lys Ala Arg Tyr His Trp Leu Val Leu Pro Trp Ala Ser Ile
    210                 215                 220

Ser Ser Leu Lys Ala Val Thr Arg Glu His Leu Glu Leu Leu Arg His
225                 230                 235                 240

Met His Thr Val Gly Glu Lys Val Ile Ala Asp Phe Ala Gly Ser Ser
                245                 250                 255

Lys Leu Arg Phe Arg Leu Gly Tyr His Ala Ile Pro Ser Met Ser His
            260                 265                 270

Val His Leu His Val Ile Ser Gln Asp Phe Asp Ser Pro Cys Leu Lys
        275                 280                 285

Asn Lys Lys His Trp Asn Ser Phe Asn Thr Glu Tyr Phe Leu Glu Ser
    290                 295                 300
```

Gln Ala Val Ile Glu Met Val Gln Glu Ala Gly Arg Val Thr Val Arg
305                 310                 315                 320

Asp Gly Met Pro Glu Leu Leu Lys Leu Pro Leu Arg Cys His Glu Cys
            325                 330                 335

Gln Gln Leu Leu Pro Ser Ile Pro Gln Leu Lys Glu His Leu Arg Lys
            340                 345                 350

His Trp Pro Lys
        355

<210> SEQ ID NO 26
<211> LENGTH: 64
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (35)..(40)
<223> OTHER INFORMATION: n is a, c, g, t or u
<220> FEATURE:
<221> NAME/KEY: misc_feature
<222> LOCATION: (64)..(64)
<223> OTHER INFORMATION: n is a, c, g, t or u

<400> SEQUENCE: 26
gtgactggag ttcagacgtg tgctcttccg atctnnnnnn gcgcttttt tttttttttt    60 ttvn                                                                64

<210> SEQ ID NO 27
<211> LENGTH: 34
<212> TYPE: DNA
<213> ORGANISM: Artificial Sequence
<220> FEATURE:
<223> OTHER INFORMATION: Synthetic construct

<400> SEQUENCE: 27
gtgactggag ttcagacgtg tgctcttccg atct                               34

<210> SEQ ID NO 28
<211> LENGTH: 52
<212> TYPE: DNA
<213> ORGANISM: Artificial Sequence
<220> FEATURE:
<223> OTHER INFORMATION: Synthetic construct

<400> SEQUENCE: 28
acactctgtc gctacgtaga tagcgttgag tgcccccccc cccccccccc cc           52

<210> SEQ ID NO 29
<211> LENGTH: 32
<212> TYPE: DNA
<213> ORGANISM: Artificial Sequence
<220> FEATURE:
<223> OTHER INFORMATION: Synthetic construct

<400> SEQUENCE: 29
acactctgtc gctacgtaga tagcgttgag tg                                 32

<210> SEQ ID NO 30
<211> LENGTH: 34
<212> TYPE: DNA
<213> ORGANISM: Artificial Sequence
<220> FEATURE:
<223> OTHER INFORMATION: Syntheitc construct

<400> SEQUENCE: 30

```
gtgactggag ttcagacgtg tgctcttccg atct                              34

<210> SEQ ID NO 31
<211> LENGTH: 48
<212> TYPE: DNA
<213> ORGANISM: Artificial Sequence
<220> FEATURE:
<223> OTHER INFORMATION: Synthetic construct

<400> SEQUENCE: 31
atctctctct tttcctcctc ctccgttgtt gttgttgaga gagattgt               48

<210> SEQ ID NO 32
<211> LENGTH: 25
<212> TYPE: RNA
<213> ORGANISM: Artificial Sequence
<220> FEATURE:
<223> OTHER INFORMATION: Synthetic construct

<400> SEQUENCE: 32
ggagucuucg ucgaguacgc ucaac                                        25
```

ENRICHMENT AND SEQUENCING OF RNA SPECIES

CROSS-REFERENCING

This application claims the benefit of U.S. provisional application Ser. No. 62/409,151, filed on Oct. 17, 2016 and is a continuation-in-part of U.S. application Ser. No. 15/137,394 filed Apr. 25, 2016. U.S. application Ser. No. 15/137,394 claims the benefit of U.S. provisional application Ser. No. 62/166,190, filed on May 26, 2015; and is a continuation-in-part of PCT/US2014/068737, filed on Dec. 5, 2014, which application claims the benefit of U.S. provisional application Ser. No. 61/912,367, filed on Dec. 5, 2013; 61/920,380, filed on Dec. 23, 2013; 62/002,564 filed on May 23, 2014; and 62/011,918 filed on Jun. 13, 2014, all of which applications are incorporated by reference herein in their entireties for all purposes.

SEQUENCE LISTING

This application contains a Sequence Listing which has been filed electronically in ASCII text format and is incorporated herein by reference in its entirety. The ASCII text file, created on Oct. 17, 2017, is named NEB-374-381-CIP-2-US_ST25.txt and is 74,303 bytes in size.

BACKGROUND cDNA libraries are often made and sequenced in order to analyze gene expression, examine alternative splicing, identify transcription start sites and to identify operons.

In many cases, however, the RNA sample used to make a cDNA library may be partially degraded. cDNA libraries made from partially degraded samples have cDNAs that are neither long nor full length, which can lead to problems with data analysis. Some of these problems may be addressed computationally. However, it would be much more desirable to have experimental methods so that the problems can be avoided, particularly for high throughput analysis. Bias may also be a problem where certain RNAs are favored in making a cDNA library and others are omitted or under represented in a library. Enrichment of targeted RNAs for assessing their representation in a population is desirable to determine transcriptional patterns and their biological meaning.

SUMMARY

In general, an improved method for making cDNA from isolated RNA species including long or full length prokaryotic RNA or eukaryotic RNA is provided. The method is believed to introduce less bias than other methods.

In one aspect, a method is provided for making a cDNA library, comprising adding an affinity tag-labeled guanosine monophosphate (GMP) to the 5' end of RNA molecules in a sample by incubating the sample with an affinity tag-labeled GTP and a capping enzyme, enriching for RNA comprising the affinity tag-labeled GMP using an affinity matrix that binds to the affinity tag, reverse transcribing the enriched RNA to produce a population of cDNAs and adding a tail to the 3' end of the population of cDNAs using a terminal transferase (TdT), to produce an cDNA library.

An embodiment of the method relies on adding a tail to the 3' end of the population of cDNAs using a TdT. This tail (e.g., a polyC or a polyG tail) can be conveniently used as a site for priming second strand cDNA synthesis by a complementary primer (e.g., an oligo(dG) or oligo(dC) primer, depending on the tail). As will be demonstrated below, it is believed some other methods, particularly methods that use template switching (see, e.g., Matz, et al., Nucl. Acids Res. 1999 27: 1558-1560 and Wu, et al., Nat Methods. 2014 11: 41-6), may be biased in the sense that such protocols have a bias for certain sequences. For example, as shown in FIG. 4C, template switching appears to be more efficient when the first nucleotide of the RNA template (which corresponds to the transcriptional start site (TSS)) is a G. As such, a cDNA library made from template switching methods may have an over-representation of cDNAs transcribed from RNAs that have a 5' G. The reason for this inefficient template switch is unclear. However, use of the present method, which relies on a TdT to add a tail onto the 3' end of the cDNA, appears to substantially reduce or largely eliminate this bias (see, e.g., FIG. 4B).

Template switching is a standard technique for adding an adaptor sequence at the 3' end of the cDNA. For reasons that are unclear, template switching introduces significant amount of bias in favor of specific nucleotides at the 5' end of the mRNA. Specifically it was found that the template switching method has a preference for certain transcripts when there is cap structure, e.g., a 7-methylguanylate cap ($m^7G$). For RNA with other 5' end structures (such as a 5' triphosphate, 5' monophosphate, 5' hydroxyl, or desthiobiotinylated cap in the RNA etc.), template switching method is less efficient. Therefore, this bias in template switching for desthiobiotinylated capped RNA template may lead to an underestimate or depletion of RNA transcripts starting with A, C or U in the sequencing library.

This problem was solved by using a TdT to add a polyG linker to the 3' end of the cDNA and hybridizing to this a poly C primer sequence as shown in FIG. 1A-FIG. 1C that was used for a few rounds of DNA amplification. A second primer sequence that overlapped with the polyC primer (nested primer) was subsequently used in a second amplification reaction that resulted in amplified DNA suitable for sequencing. Although requiring more reaction steps than template switching, this approach was uniquely suited for efficient creation of cDNA libraries.

TdT is a template independent polymerase that catalyzes the addition of deoxynucleotides to the 3' hydroxyl terminus of DNA molecules. In the presence of only one type of deoxynucleotides such as dGTP, it adds a polyG linker that contains ~10 to 15 Gs to the 3' end of cDNA. This polyG linker could be used for second strand synthesis with a primer that contains the complementary polyC sequence. An important benefit of the TdT based method described herein is the avoidance of bias related to the nature of the 5'end nucleotide of the RNA.

In eukaryotes, the 5' cap found on the 5' end of an mRNA molecule consists of a guanine nucleotide connected to mRNA via an unusual 5' to 5' triphosphate linkage. This is frequently guanosine that is methylated on the 7 position ($m^7G$) directly after capping in vivo by a methyltransferase. While eukaryotic mRNA frequently has a cap, not all eukaryotic mRNA have caps (e.g. histone mRNA). Moreover, 5'caps may be found on RNAs that are not mRNA. Decapping and recapping described below is applicable to any capped RNA species.

In order to prepare desthiobiotin (DTB) labeled eukaryotic mRNA from capped mRNA, the mRNA must be decapped and then can be recapped (see for example, WO 2015/085142). We have identified 2 classes of enzymes that can decap eukaryotic mRNA to leave a 5' diphosphate. One enzyme class belongs to the histidine triad (HIT) superfamily of pyrophosphatases, the scavenger decapping enzymes (DcpS). Two examples of such are the *Saccharomyces cerevisiae* DcpS and the *Schizosaccharomyces pombe* DcpS (nhm1). These two enzymes demonstrate only 36% amino acid identity with each other. The other class of enzyme also belong to the HIT superfamily of nucleotidyltransferases and are referred to as aprataxin (APTX) (RNA), also known as 5'deadenylase and Hnt3p. Two examples of such are the *Saccharomyces cerevisiae* APTX and the *Schizosaccharomyces pombe* APTX. These two enzymes demonstrate only 33% amino acid identity with each other. We have shown here that all four of these enzymes can be used to remove the cap from eukaryotic mRNA with a degree of specificity for specific caps (see FIG. 5A-5B). Different decapping enzymes can be used to identify different 5' caps on long RNAs (including full length RNAs) owing to their various specificities. An example is shown in FIG. 9 There are other examples of decapping enzymes leaving 5' diphosphate such as Nudt12 and Nudt15 (Grudzien-Nogalska, et al., Wiley Interdisciplinary Reviews: RNA. 2017; 8:E1379). After decapping, eukaryotic 5' diphosphate terminated mRNA can be subjected to the same enrichment as that of 5' triphosphate terminated prokaryotic mRNA. Intact, eukaryotic mRNA generally contains a poly(A) tail at the 3' end. Labeled capped or recapped mRNA may be enriched by affinity binding of the capped RNA and further enriched by affinity binding of the poly (A) tail. The poly A tail also provides a convenient target for a polyd(T) primer to initiate reverse transcription.

Analysis of full length mRNA molecules, in one embodiment, requires one or more steps selected from the following: (1). Enriching for mRNA from a cellular environment in which non-mRNA molecules predominate in significant excess; (2). Reverse transcribing the RNA to form a cDNA and adding a DNA sequence at the 3' end of the cDNA suitable for associating a primer for second strand synthesis and for DNA amplification; and then sequencing the amplified DNA.

DESCRIPTION OF FIGURES

The patent or application file contains at least one figure executed in color. Copies of this patent or application publication with color figures will be provided by the Office upon request and payment of necessary fee.

The skilled artisan will understand that the drawings, described below, are for illustration purposes only. The drawings are not intended to limit the scope of the present teachings in any way.

(1) Bacterial mRNA has a 5'ppp nucleotide that reacts with a capping enzyme such as vaccinia resulting in attachment of an affinity label such as biotin or DTB (DTB is shown here). Processed RNA (rRNA, tRNA) or degraded RNA having a single 5'p nucleotide or 5'OH does not react with the capping enzyme and cannot be capped with an affinity label. Eukaryotic mRNA, which generally has a 5'cap, can be treated with a decapping enzyme to produce 5'pp nucleotide, which can be capped in the same way as for bacterial mRNA described here (also see WO 2015/085142).

(2) Optionally, a polyA polymerase is provided to add a polyA tail to the 3' end of RNA (e.g. bacterial RNA) if reverse transcription is desirable. Eukaryotic mRNA generally includes a polyA tail. The polyA tail provides a target for an oligo dT primer which enable initiation of the reverse transcriptase reaction.

(3) The labeled RNAs binds with high affinity to a matrix (for example, streptavidin beads) in a high salt buffer (for example, NaCl concentration above 250 mM). The uncapped and therefore unbound RNAs are washed away using the high salt buffer.

(4) The affinity bound RNAs can then be eluted from the matrix in a suitable elution buffer to provide an enriched preparation of non-degraded primary transcripts.

Figure 1A:
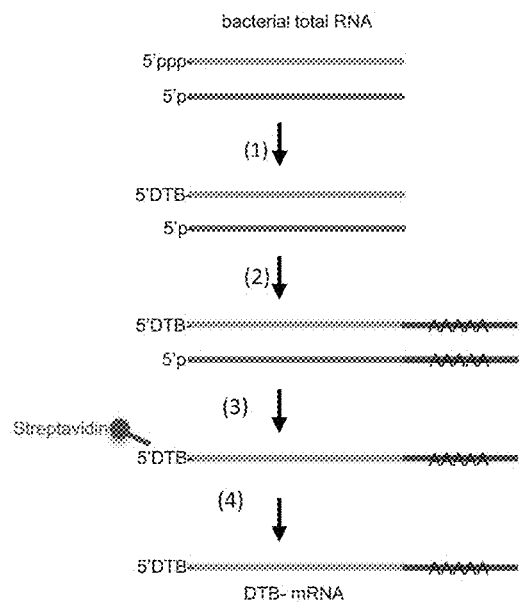
FIG. 1A-FIG. 1C schematically illustrates a workflow for enrichment and sequencing of bacterial primary transcripts FIG. 1A schematically illustrates enrichment of long or full length primary transcripts from bacterial total RNA.
Figure 1B:
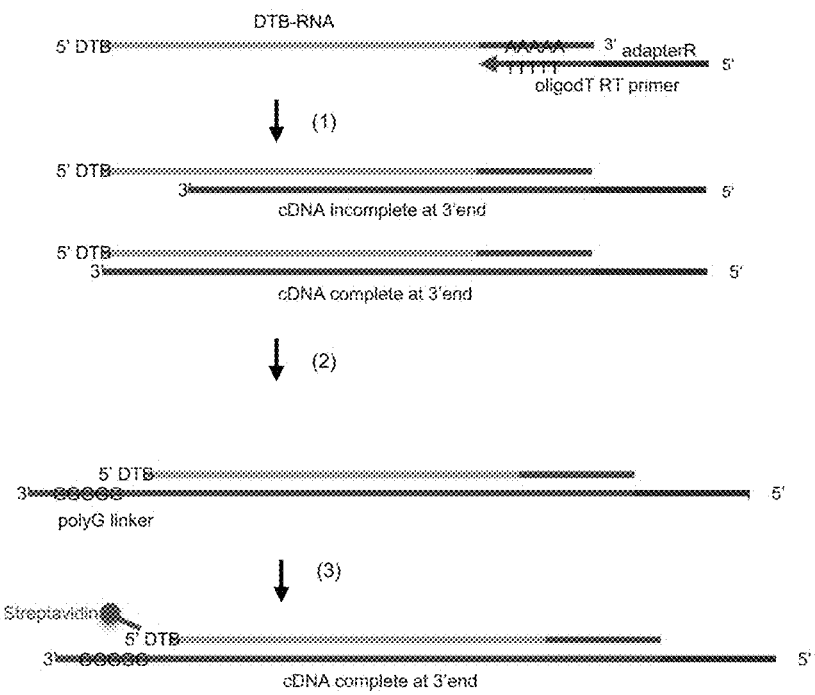

FIG. 1B schematically illustrates a method of first strand cDNA synthesis for 5' labeled RNA molecules and addition of a polyG linker by TdT.

(1) An oligodT primer that is optionally anchored and may include a 5' adapter sequence (adapaterR), anneals to the start of the polyA tail and enables a reverse transcriptase to initiate synthesis of the cDNA in a 3' direction. Alternatively, an adapter sequence can be ligated to the 3' end that can serve as a priming sequence for a primer for reverse transcriptase. In either case, the adapter sequence at the 5' end of cDNA is used for subsequent PCR amplification. In embodiments, a unique identifier sequence (UID) may be included in the adapter where the UID is designed to identify and remove PCR duplicates. The reverse transcriptase generates incomplete as well as complete cDNAs. The RNA template of these partial cDNAs may be removed by RNAse digestion, e.g., by a single stranded RNAs such as RNase $I_f$ as desired.

(2) TdT adds a polyG linker to the 3' end of cDNA in a template-independent manner. The length of polyG linker is preferably in the range of about 7-50 nucleotides or 10-20 nucleotides in the presence of 1 mM dGTP. The polyG linker is used for the subsequent synthesis of the second strand DNA.

(3) Affinity beads capture the RNA/cDNA hybrid. If the sample has been treated with an RNase, the cDNA that has not reached the 5' cap-site is removed through washing steps since it is no longer attached to the affinity tag. The cDNA on the beads is enriched and clean and ready for second strand synthesis.

Figure 1C:
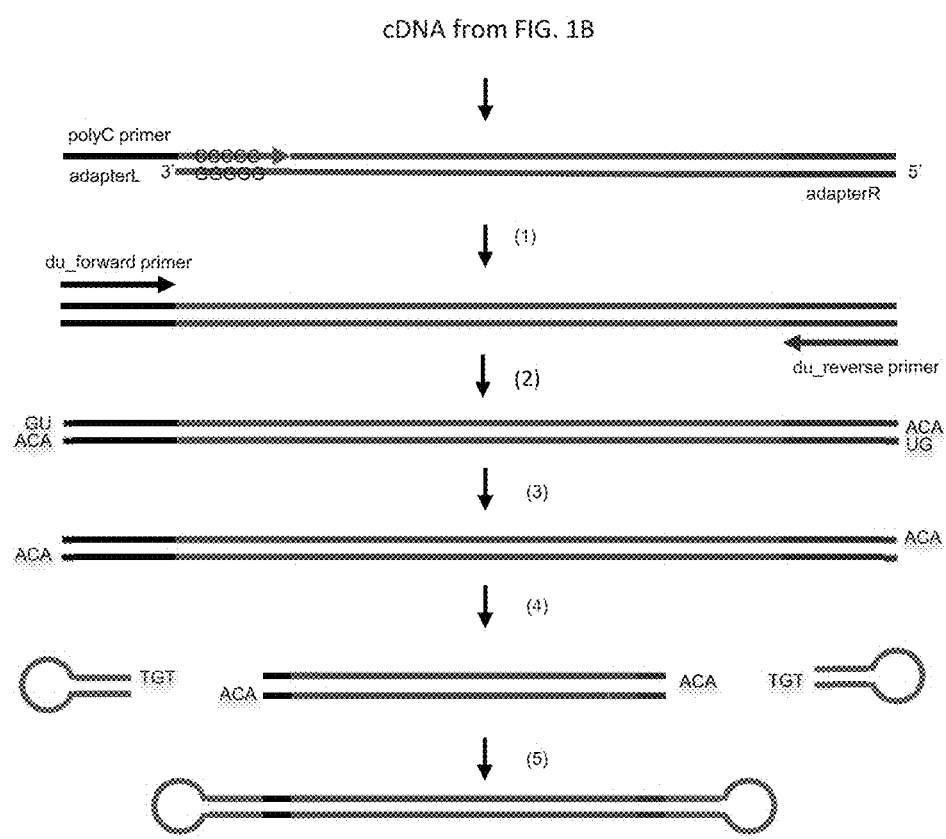

FIG. 1C schematically illustrates second strand synthesis and library preparation for a large molecule sequencer.

(1) The second strand DNA is synthesized from the cDNA using a polymerase (e.g. Q5® (New England Biolabs, Ipswich, Mass.)) from a polyC primer. The polyC primer contains a polyC sequence that binds to the polyG linker at the 3' end of cDNA. It also contains an adapter sequence (adapterL) for later large scale PCR amplification. The double strand DNA undergoes amplification (using for example, 5 PCR cycles) with the polyC primer and the reverse primer that contains the adapterR sequence that binds to the 5' end of cDNA.

(2) Optionally, the product from previous PCR undergoes a second round amplification with a second set of primers (du_forward and du_reverse primer) to provide sufficient DNA for size selection for large molecule sequencing. The second set of primers contains adapterL and adapterR binding sites, respectively. In addition, the primers may contain deoxyuridine (dU) near the 5'end. In one example, LongAmp® polymerase (New England Biolabs, Ipswich, Mass.) is used to read through dU and amplify large fragments. This polymerase adds a non-templated adenosine to the 3' ends of the PCR product.

(3) The dU base can be removed by USER® (Uracil-Specific Excision Reagent) (New England Biolabs, Ipswich, Mass.), which includes uracil-N-deglycosylase (UNG) or uracil DNA glycosylase (UDG), to provide a 3'-N base extension (cohesive end) for ligation to any loop adapter that has a complementary 3'-N' base extension associated with a suitable adaptor for, for example, long DNA sequencing. Here N is shown in FIG. 1C to be 3 bases (ACA).

(4) DNA with a cohesive-end is ligated to a suitable adapter (for example a PACBIO loop adapter (Pacific Biosciences, Menlo Park, Calif.)) using a DNA ligase (e.g. T4 ligase). The cohesive-ends increase ligation efficiency shortening the ligation time and preventing self-ligation, chimera and adapter dimer formation.

(5) Exonucleases such as Exonuclease III and VII remove the remaining unligated PCR products as well as the extra adapters after ligation.

Figure 2:
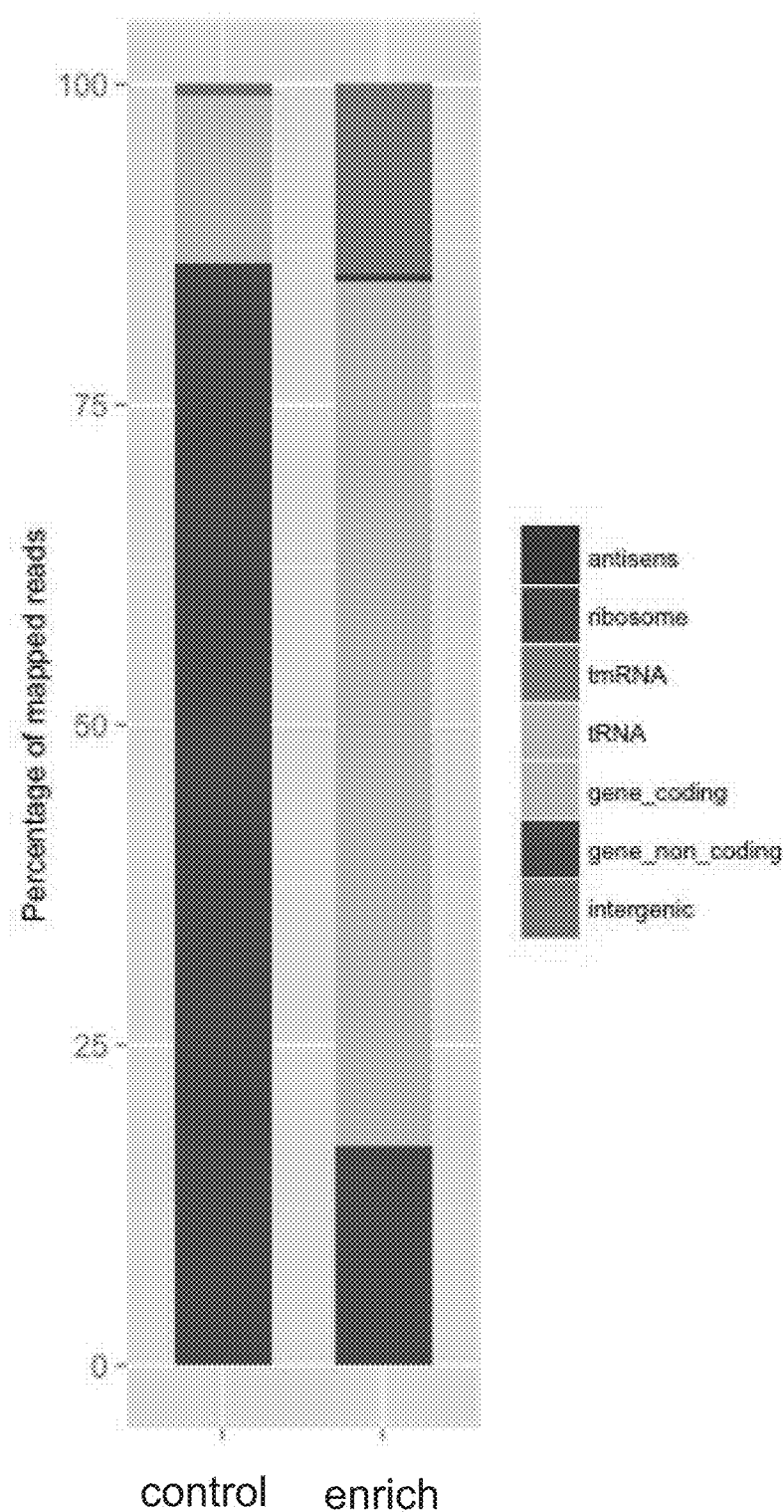

FIG. 2 shows enrichment of primary transcripts over processed transcripts using the method in FIG. 1A-FIG. 1C. The results show the substantial enrichment of the primary transcripts compared with control. Both control and enriched sample include the addition of an affinity labeled cap to the 5' end of an RNA having a triphosphorylated nucleotide. The enriched sample differs from the control by an enrichment step that involves binding of the capped RNA to an affinity matrix in a buffer. The data shows significant improvement in the efficiency of the enrichment process in which all processed and degraded RNA is removed allowing for greater transcriptome coverage while minimizing non-target reads.

The histogram shows PACBIO sequencing reads that are mapped to the *E. coli* genome. In the control group, up to 85% of the reads are mapped to genes that encode processed rRNAs. In contrast, with Cappable-seq™ (New England Biolabs, Ipswich, Mass.), 85% of the reads are mapped to the primary transcripts from protein coding genes, while the processed RNA only accounts for 5% of the total reads. (Cappable-seq is referred to here as a method for enriching and sequencing primary transcripts. This is achieved by enzymatically modifying the 5' triphosphorylated (or the 5' diphosphorylated) end of RNA with a selectable tag such as biotin or a biotin derivative, transcripts. Affinity labeled molecules can be isolated from the in-vivo processed RNA).

Figure 3A:
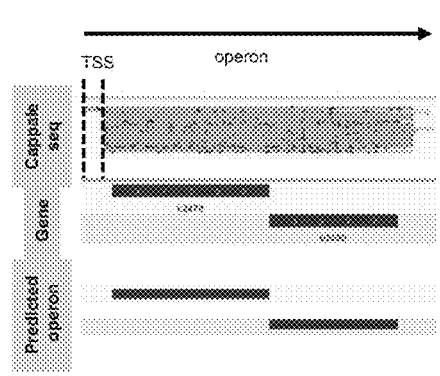
Figure 3B:
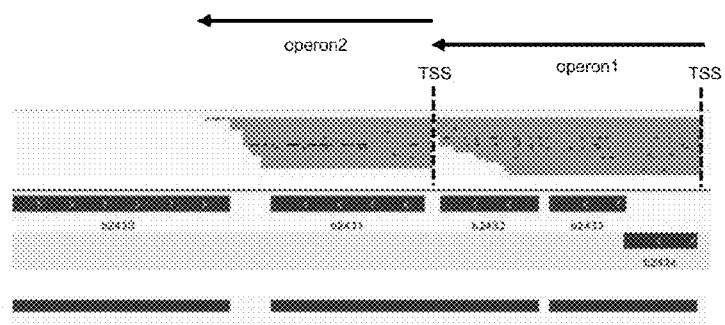

FIG. 3A-FIG. 3B shows the use of the method in FIG. 1A-FIG. 1C (referred to here as Cappable-seq) to identify new bacterial operons.

The top row is labeled Cappable-seq and shows the PACBIO sequencing reads generated from the library of cDNA molecules which in turn were generated from enriched mRNA. The 5' end of the operon was accurately defined (labeled with dash line). For the transcripts sharing the same TSS, the 3' end of the longest transcript is predicted to be the 3' end of the operon.

Two examples of the newly identified operons are shown here for *E. coli*.

FIG. 3A. Gene b2479 and b2480, which are previously annotated in regulon DB were found to be synthesized from two separate operons, were instead found to be synthesized from the same operon by Cappable-seq.

FIG. 3B. Gene b2434, b2433 and bc2432 were shown to be expressed from the same operon (operon 1) while bc2431 is defined in another operon (operon 2) using the present methods. These results differ from the previous computational predictions based on start and stop codons.

Figure 4A:
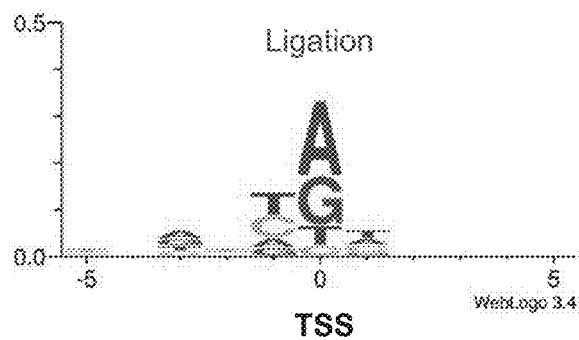
Figure 4A:
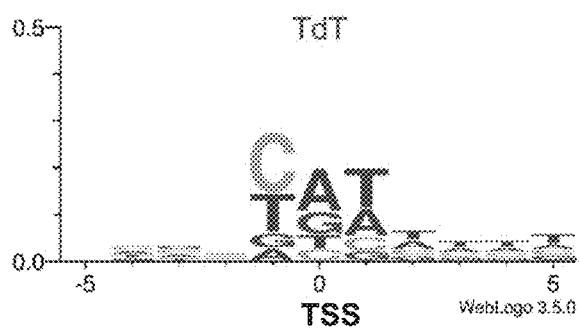
Figure 4A:
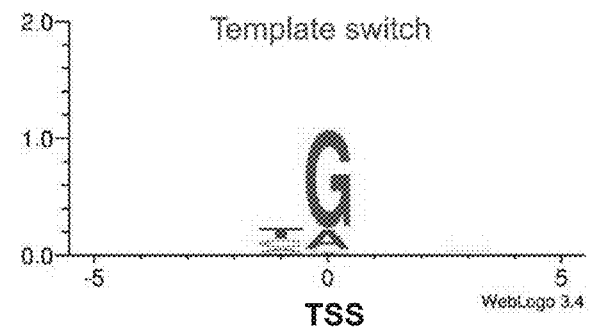

FIG. 4A-FIG. 4C show that compared with the TSS identified by a standard ligation based method (also see U.S. application Ser. No. 15/137,394), there is a nucleotide preference at TSS using a template switching method; and this bias is significantly reduced using a TdT method instead.

FIG. 4A shows that the nucleotides at the TSS of *E. coli*, which are identified using standard ligation methods.

FIG. 4B shows the substantial elimination of bias at the TSS using a TdT based method for desthiobiotinylated *E. coli* RNA.

FIG. 4C shows that there is significant nucleotide bias at the TSS using template switching for desthiobiotinylated *E. coli* RNA.

Figure 5A:
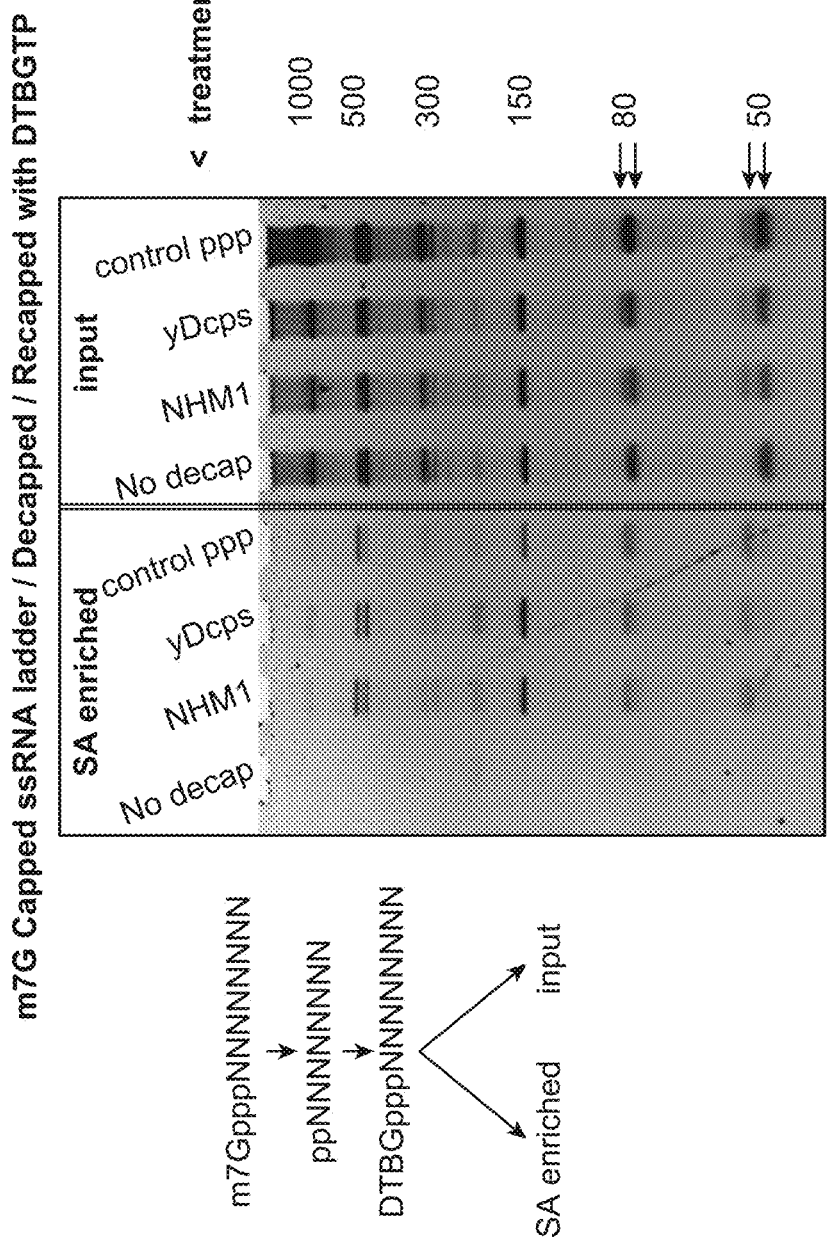
Figure 5B:
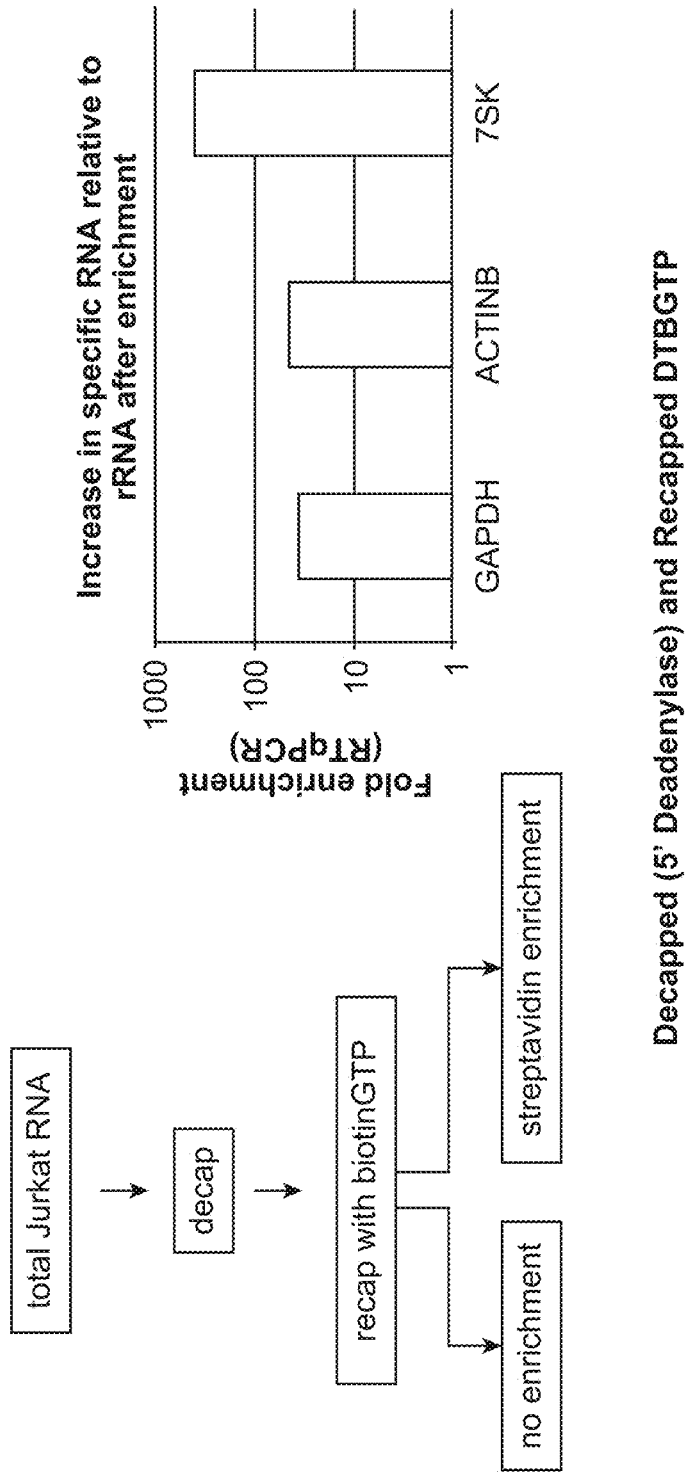

FIG. 5A-FIG. 5B show the results of experiments in which in vitro synthesized RNA or eukaryotic RNA were decapped and recapped with desthiobiotin guanosine triphosphate (DTB-GTP) (New England Biolabs, Ipswich, Mass.) and enriched by streptavidin.

FIG. 5A is a UREA polyacrylamide gel of $m^7G$ capped synthetic RNA ranging in size from 50 nucleotides to 1000 nucleotides which has been decapped with the DcpS enzymes of *Schizosaccharomyces pombe* and *Saccharomyces cerevisiae* and recapped with DTB-GTP and indicate that the decapping/recapping/enrichment is independent of the size of the RNA.

FIG. 5B is a graph which indicates the fold enrichment after streptavidin treatment of specific RNA genes which have been decapped with *Saccharomyces cerevisiae* HNT3 (5' deadenylase) and recapped with DTB-GTP.

Figure 6:
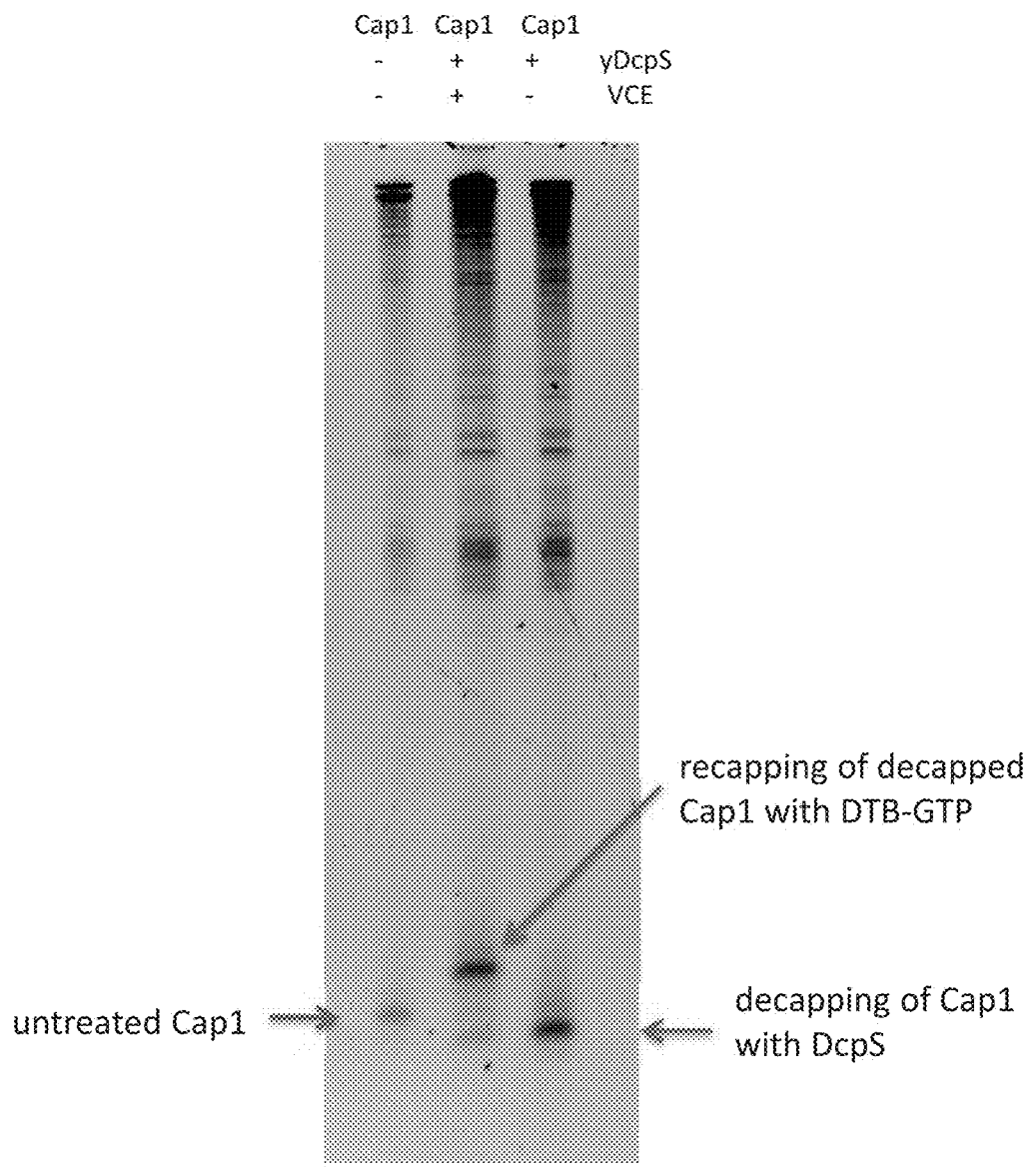

FIG. 6 is a gel showing that a synthetic 25mer RNA that has a $m^7Gppp$ cap and a 2' methylated first nucleotide can be successfully decapped using yeast DcpS and recapped with DTB-GTP using Vaccinia capping enzyme (VCE) (New England Biolabs, Ipswich, Mass.). In the first lane, the Cap received no treatment. In the second lane, the Cap was decapped and recapped. In the third lane, the results of decapping are shown.

Figure 7:
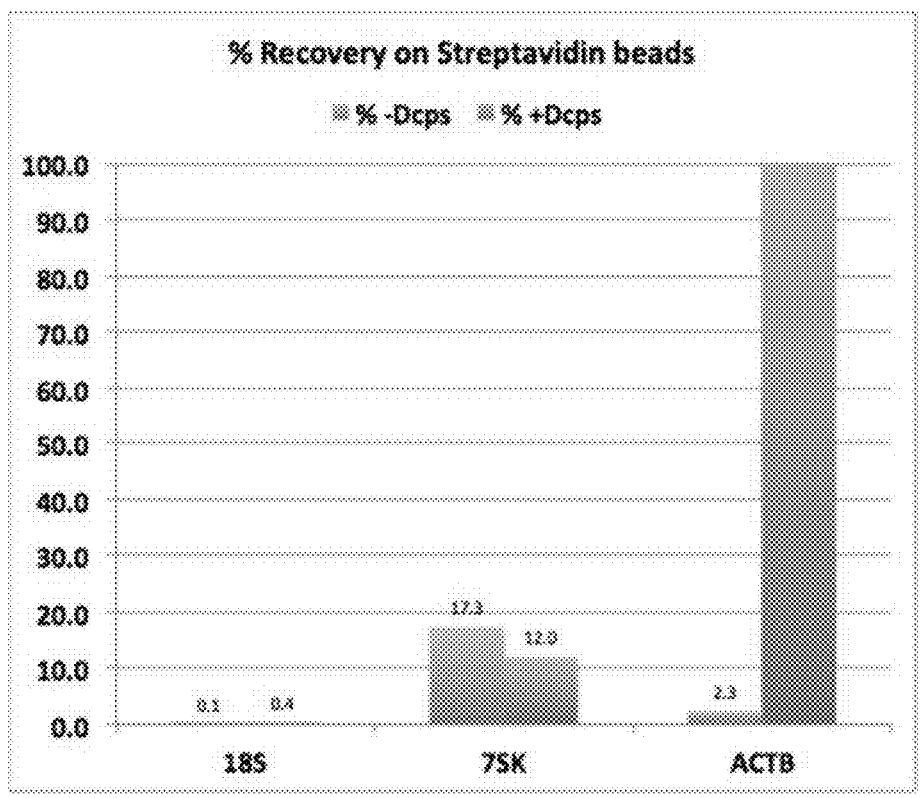

FIG. 7 is a graph showing the results of quantitative RT-PCR analysis of transcripts that have been decapped by yeast DcpS, capped by DTB using VCE, and captured on streptavidin beads. Three transcripts were analyzed: 18S, 7SK and actin beta (ActB). The results show that the 18S RNA was not enriched, the tri-phosphorylated 7SK RNA was enriched (relative to ribosomal RNA) regardless of DcpS treatment since it is readily capped and requires no prior decapping, and the ActB RNA was enriched only with the DcpS pre-treatment.

Figure 8:
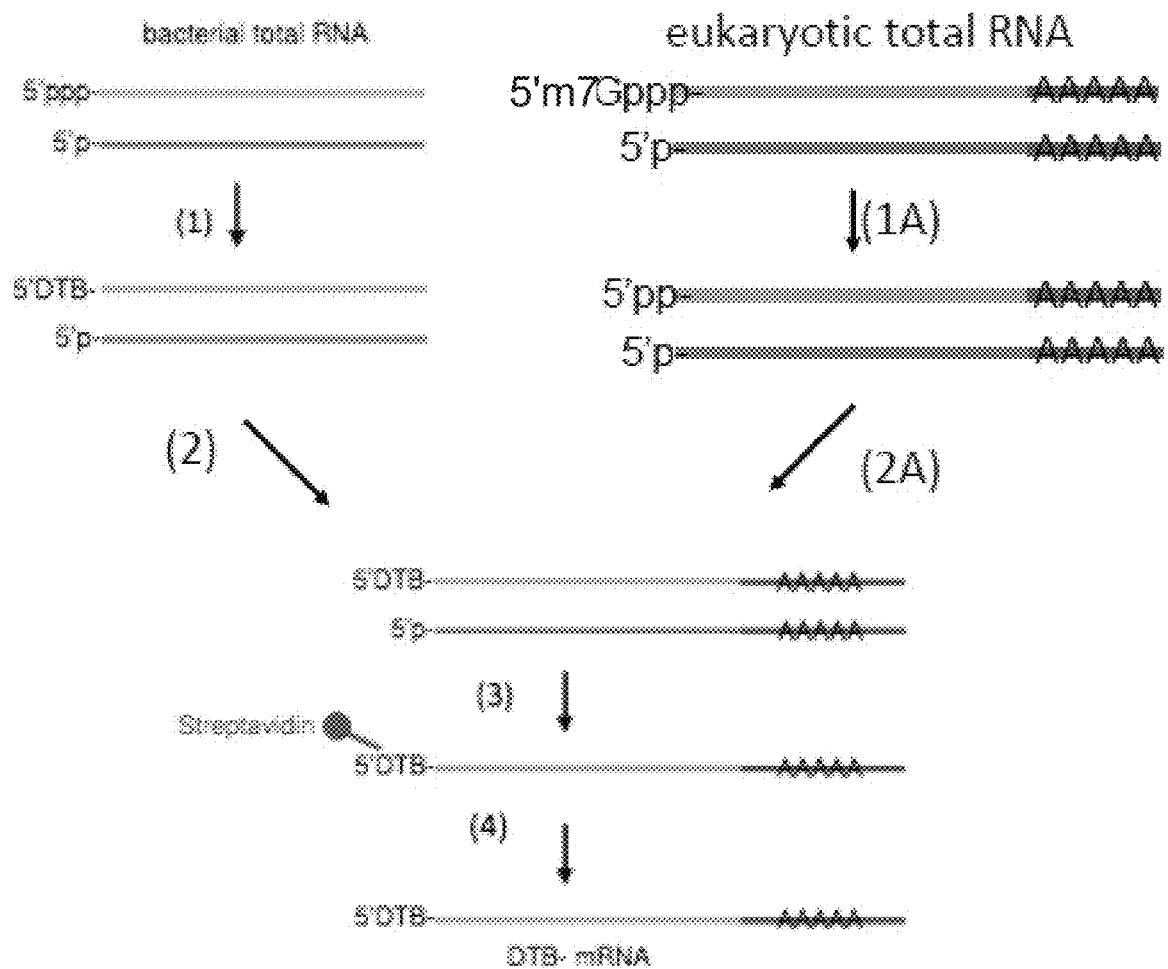

FIG. 8 schematically illustrates a potential workflow for enriching and sequencing bacterial or eukaryotic primary transcripts. (1) Capping RNA with DTB at the 5'ppp end of RNA (for example prokaryotic mRNA) from a preparation of total RNA. (2) Adding poly A tail at the 3' end; (1A) Decapping a eukaryotic RNA with poly A tail to remove 5'$m^7$Gp; (2A) recapping with 5'DTB-GTP; (3) enriching for 5'DTB labeled RNA by binding to streptavidin matrix; (4) obtaining 5'DTB-mRNA.

Figure 9:
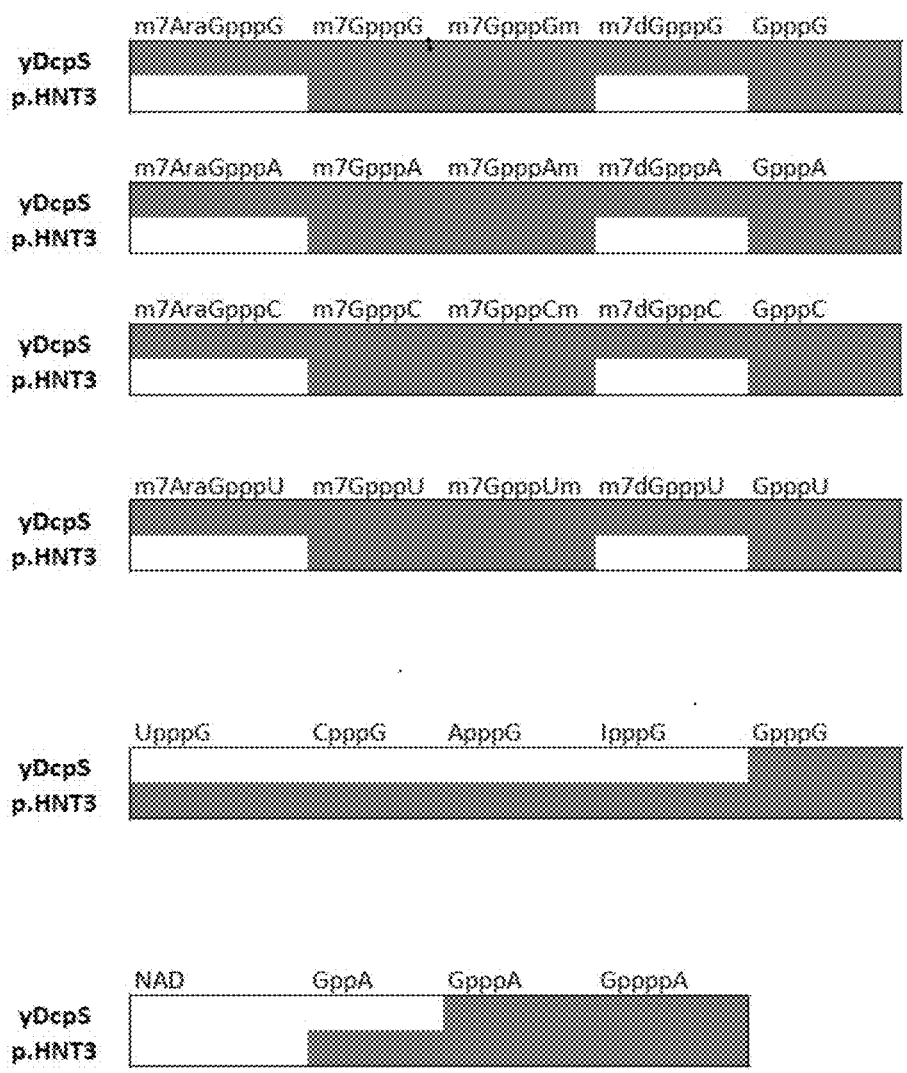

FIG. 9 shows the decapping specificity of decapping enzymes from *Saccharomyces cerevisiae* DcpS (yDcpS) and *Schizosaccharomyces pombe* HNT3 (Hnt3p). This data show that the different decapping enzymes have different substrate specificities. The structure of the cap at the 5' end of the RNA transcripts for a particular gene in a sample can therefore be deduced by independently treating different aliquots of a sample using different decapping enzymes. Subsequent steps of analysis might include capping the products with an affinity tag-labeled GMP using a capping enzyme or chemically, enriching for RNA comprising the affinity tag-labeled GMP, analyzing the enriched RNA (e.g., by sequencing), and comparing the results obtained for one decapping enzyme to another.

Figure 10:
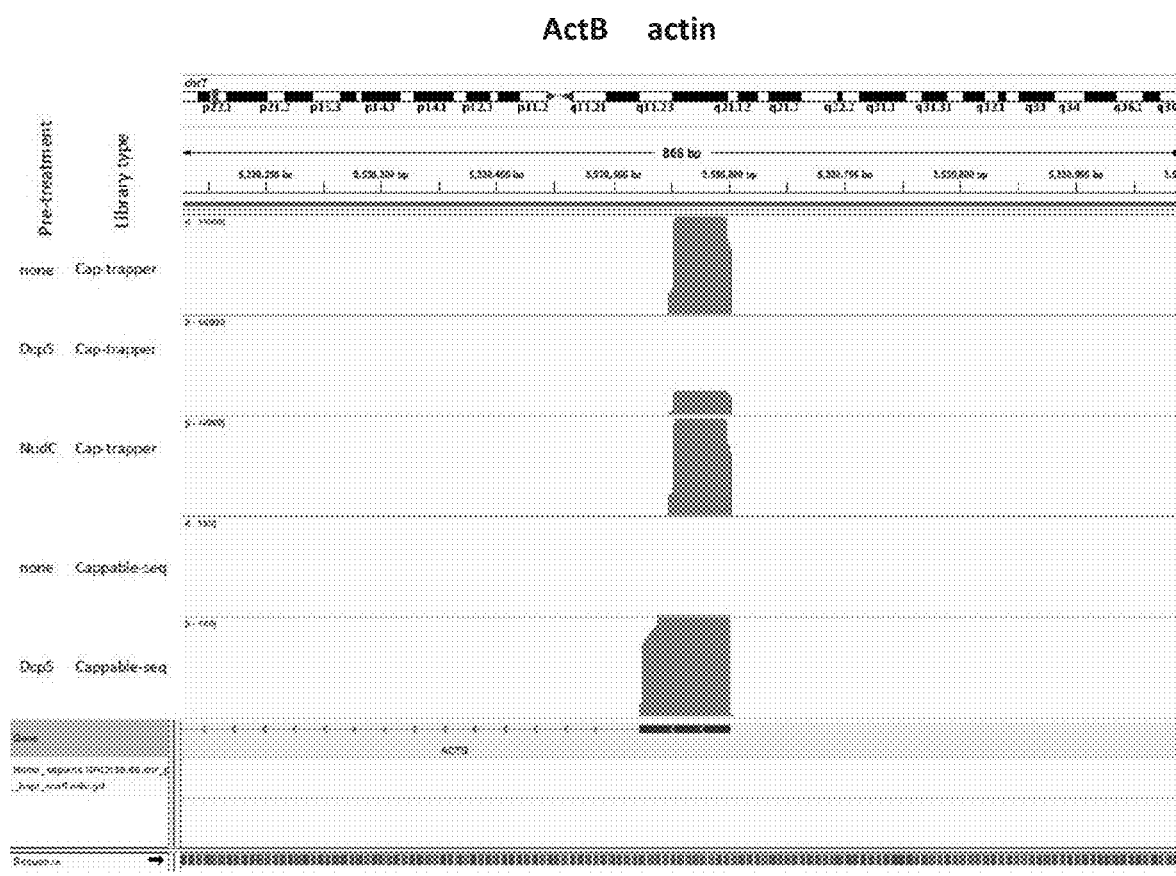

FIG. 10 is a display of the number of reads for ActB using the "Cappable-seq" method (i.e., by incubating the sample with VCE and DTB-GTP and then enriching for the biotinylated RNAs using streptavidin, as described in Example 5 and U.S. application Ser. No. 15/137,394) and compared to sequencing reads obtained using the "Cap-trapper" method (which adds a biotin to the RNAs via a chemical reaction, as described in Carninci, et al., Genomics. 1996 37: 327-36) from RNA samples that have been treated or not pre-treated with DcpS or NudC (which are both decapping enzymes). In the Cappable-seq method, only transcripts that have an intact 5' triphosphorylated (or 5' diphosphate) end are biotinylated, captured and sequenced. In the Cap-trapper method, only transcripts that have caps that are hydrazide-reactive are (e.g., transcripts that have a 5' $m^7$Gppp cap) are biotinylated, captured and sequenced. The Cap-trapper data was obtained from DNAFORM (Yokahama, JP) using their Custom CAGE™ (Cap Analysis of Gene Expression) Library Preparation & Analysis service. In the experiments shown in FIG. 10, the number of sequence reads obtained by the Cap-trapper method was reduced by pre-treatment with DcpS, indicating that the ActB transcripts have a hydrazide-reactive cap (most likely a 5' $m^7$Gppp cap). Similar results were obtained for other genes, including lactate dehydrogenase (LDHA) and thymosin (TMSB10) (not shown).

Figure 11:
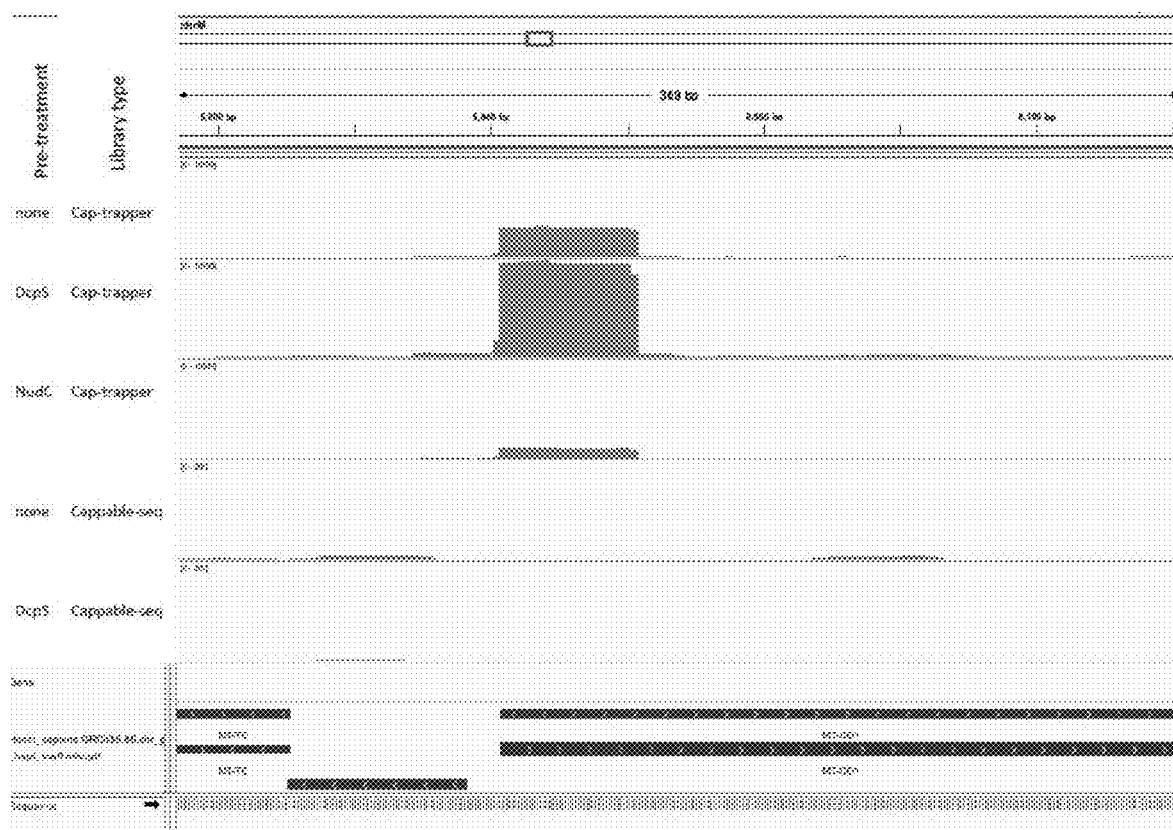

FIG. 11 is a display of the number of reads for mitochondrial cytochrome C oxidase using the Cappable-seq method compared to sequencing reads obtained using the Cap-trapper method, from RNA samples that have been treated or not treated with the DcpS or NudC decapping enzymes.

Figure 12:
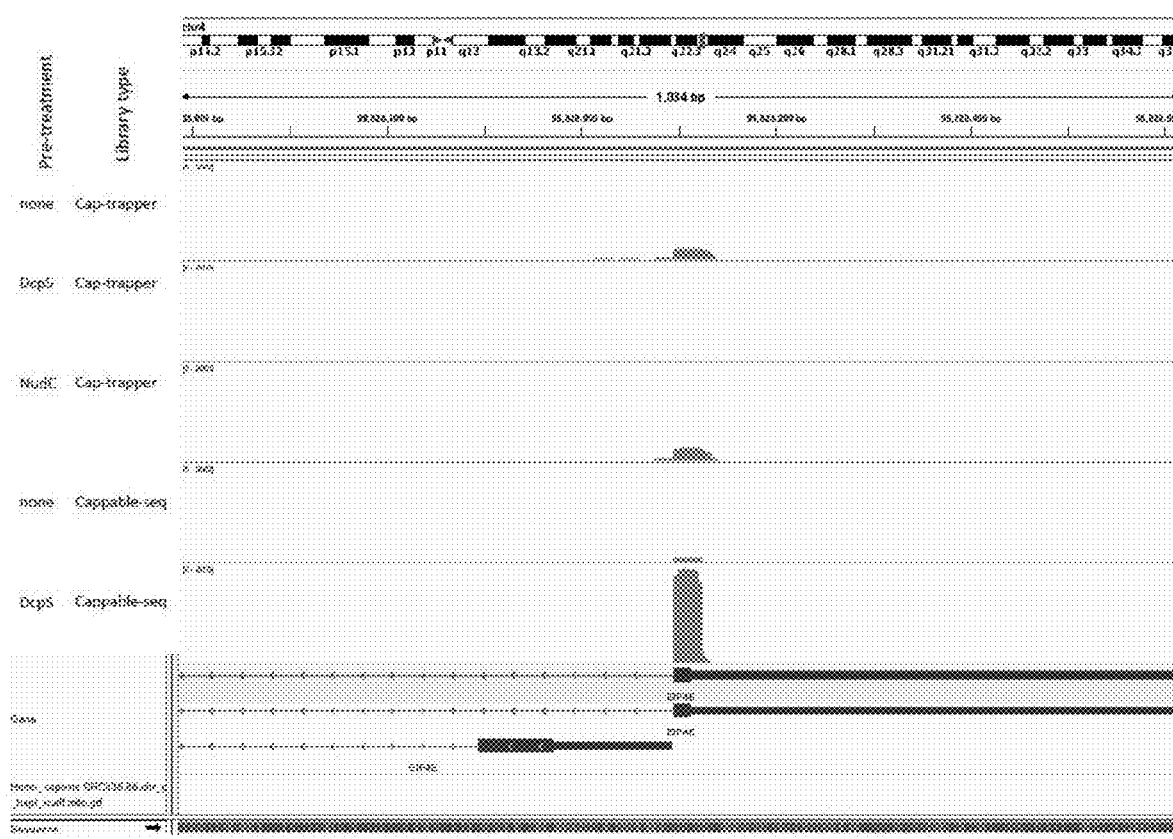

FIG. 12 is a display of the number of reads from sequencing results for EIF4E using the Cappable-seq method compared to sequencing reads obtained using the Cap-trapper method from RNA samples that have been treated or not treated with DcpS or NudC decapping enzymes.

Figure 13:
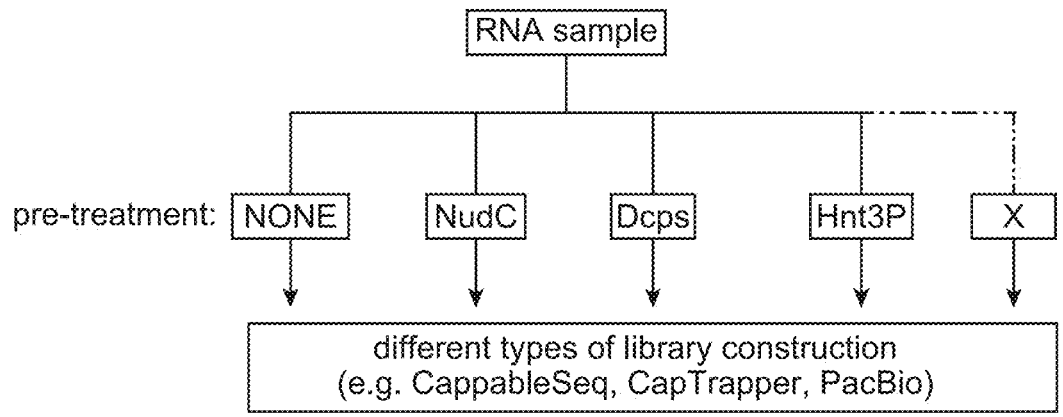
Figure 13:
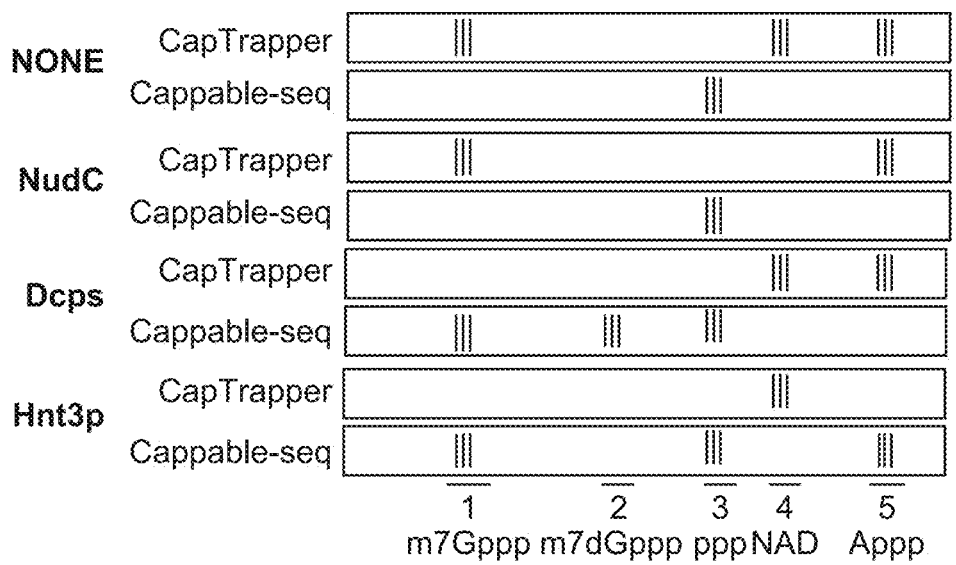

FIG. 13 shows (A) an exemplary workflow scheme for determining cap structures on the 5' end of different transcripts, and (B) a schematic for sequencing data display and interpretation.

FIG. 14 shows a sequence alignment of APTX from different organisms (from top to bottom, SEQ ID NO:11-25).

FIG. 15 shows a sequence alignment of DcpS proteins from different organisms (from top to bottom, SEQ ID NO:1-10).

DETAILED DESCRIPTION

Unless defined otherwise, all technical and scientific terms used herein have the same meaning as commonly understood by one of ordinary skill in the pertinent art. Embodiments described herein may include one or more ranges of values (e.g., size, concentration, time, temperature). A range of values will be understood to include all values within the range, including subset(s) of values in the recited range, to a tenth of the unit of the lower limit unless the context clearly dictates otherwise.

As used herein, the articles "a", "an", and "the" relate equivalently to a meaning as singular or plural unless the context dictates otherwise.

The term "cDNA library" includes a sequencing library produced from the cDNA.

The term "non-naturally occurring" refers to a composition that does not exist in nature.

Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an immunologically tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

Numeric ranges are inclusive of the numbers defining the range. Unless otherwise indicated, nucleic acids are written left to right in 5' to 3' orientation; amino acid sequences are written left to right in amino to carboxy orientation, respectively.

The practice of the disclosed methods, compositions, and kits may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, A., Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Provided herein, among other things, is a method for making a cDNA library, comprising: adding an affinity tag-labeled GMP to the 5' end of full length RNA molecules in a sample by incubating the sample with an affinity tag-labeled GTP (e.g., DTB or biotin GTP) and a capping enzyme, enriching for RNA comprising the affinity tag-labeled GMP using an affinity matrix that binds to the affinity tag, reverse transcribing the enriched RNA to produce a population of cDNAs and adding a tail to the 3' end of the population of cDNAs using a TdT. This method is believed to produce an unbiased cDNA library, where the term "unbiased" is intended to mean that the library has significantly reduced bias in the terminal nucleotide relative to methods that rely on template switching (see generally FIG. 4A-FIG. 4C). For example, use of the present method to make cDNA from a population of full length RNA molecules that has equal amounts of RNA molecules having 5' terminal Gs, As, Us, and Cs should result in a population of full length cDNA molecules that also has approximately equal amounts of molecules having 3' terminal Gs, As, Ts, and Cs (e.g., each in the range of 20% to 80% of the population), rather than a bias towards only one nucleotide. Embodiments of the method results in a sequencing library containing an equimolar representation of each original RNA molecule.

Embodiments of the method can be used to obtain a relatively unbiased cDNA population from full length eukaryotic mRNAs (which have a 5' m$^7$Gppp cap that can be enzymatically removed) and also have a polyA tail, or prokaryotic RNAs (which have a triphosphate cap), from a sample that comprises eukaryotic RNA, prokaryotic RNA or a mixture of both eukaryotic and prokaryotic RNA. For example, in some cases, the sample may comprise RNA from a eukaryote and the method comprises, prior to capping with the affinity tag-labeled GMP, enzymatically decapping the 5'-m$^7$Gppp capped mRNA in the sample using a 5'deadenylase (see for example, U.S. Pat. No. 8,486,666 or deadenylase having at least 90% identity to *Schizosaccharomyces pombe* HNT3 or DcpS having at least 90% identity to *Schizosaccharomyces pombe* NHM1 or DcpS having at least 90% identity to *Saccharomyces cerevisiae* YLR270W) and then capping the decapped molecules with a capping enzyme (e.g., VCE) using as a substrate, an affinity tag-labeled GMP. In other embodiments, an unbiased library can be made from prokaryotic RNA by (a) adding an affinity tag-labeled GMP to the 5' end of 5'-triphosphorylated RNA molecules in a sample by incubating the sample with an affinity tag-labeled GTP and a capping enzyme; (b) enriching for RNA comprising the affinity tag-labeled GMP using an affinity matrix that binds to the affinity tag, and then performing the remainder of the steps of the method as discussed above and below. In some embodiments, the enriching may selectively bind the RNA to streptavidin beads in a buffer containing 1 M-3 M salt, e.g., NaCl.

A method for making a full length eukaryotic cDNA library is provided. In these embodiments, the 5' end of the full length mRNA is captured by enzymatically decapping the RNA to remove the 5'-m$^7$Gppp cap (which leaves a 5' diphosphate end), enzymatically recapping the mRNA with an affinity tag, and enriching for RNAs that contain the affinity tag. The 3' end of the enriched mRNA molecules have a polyA tail and, as such, full length cDNA can be made by reverse transcribing the enriched RNA sing using oligo-dT primer. In some embodiments, this method may comprise treating a sample comprising full length, capped, eukaryotic RNA molecules with a decapping enzyme to produce decapped eukaryotic mRNA; adding an affinity tag-labeled GMP to the 5' end of the decapped eukaryotic mRNA molecules by incubating the decapped eukaryotic mRNA with an affinity tag-labeled GTP, e.g., DTB-GTP and a capping enzyme (e.g., VCE). In the next step, the method may comprise enriching for RNA comprising the affinity tag-labeled GMP using an affinity matrix that binds to the affinity tag and reverse transcribing the enriched RNA using oligo-dT primer to produce a full length eukaryotic cDNA library. The RNA comprising the affinity tag-labeled GMP may be eluted from the affinity matrix prior to reverse transcription, or it may be reverse transcribed on the column.

In order to perform several embodiments of the present method on eukaryotic mRNA the natural m$^7$G cap should first be removed to leave a 5' diphosphate. Two classes of enzymes which can achieve this goal are exemplified herein. The first class is the histidine triad (HIT) superfamily of pyrophosphatases that include APTX for example, *Saccharomyces cerevisiae* Hnt3p and *Schizosaccharomyces pompe* Hnt3p and DcpS. The APTX are also known as DNA 5' deadenylases were not known to decap mRNAs. Examples of DcpS enzymes, include *Saccharomyces cerevisiae* DcpS and *Schizosaccharomyces pombe* Nhm1p. It has been shown that Dcps enzymes remove the G cap and leave 5' diphosphate RNA on full length RNA, although the DcpS enzymes were previously considered to be inactive on RNA longer than 15 nucleotides (Liu, et al., EMBO J. 2002 21: 4699-708). The 5' diphosphate RNA can be capped using DTB-GTP and VCE in the same way as the 5' triphosphate capped RNAs of prokaryotic origin.

The amino acid sequences of four exemplary decapping enzymes are shown below:

*S. cerevisiae* Hnt3p (SEQ ID NO: 12)
MSWRYALKNYVTSPETVNDDTVTYFDDKVSIIRDSFPKSECHLLILPRTM

QLSRSHPTKVIDAKFKNEFESYVNSAIDHIFRHFQEKFRIKKSDDDKDPC

-continued
```
WDDILKDKNKFVRNFVQVGIHSVPSMANLHIHVISKDFHSVRLKNKKHYN

SFNTGFFISWDDLPLNGKNLGTDKEIETTYLKEHDLLCCYCQRNFSNKFS

LLKKHLELEFNSHFELK
```

S. pombe Hnt3p
(SEQ ID NO: 11)
```
MSVHKTNDAFKVLMNSAKEPIVEDIPKKYRKQSFRDNLKVYIESPESYKN

VIYYDDDVVLVRDMFPKSKMHLLLMTRDPHLTHVHPLEIMMKHRSLVEKL

VSYVQGDLSGLIFDEARNCLSQQLTNEALCNYIKVGFHAGPSMNNLHLHI

MTLDHVSPSLKNSAHYISFTSPFFVKIDTPTSNLPTRGTLTSLFQEDLKC

WRCGETFGRHFTKLKAHLQEEYDDWLDKSVSM
```

S. cerevisiae DcpS
(SEQ ID NO: 9)
```
MSQLPTDFASLIKRFQFVSVLDSNPQTKVMSLLGTIDNKDAIITAEKTHF

LFDETVRRPSQDGRSIPVLYNCENEYSCINGIQELKEITSNDIYYWGLSV

IKQDMESNPTAKLNLIWPATPIHIKKYEQQNFHLVRETPEMYKRIVQPYI

EEMCNNGRLKWVNNILYEGAESERVVYKDFSEENKDDGFLILPDMKWDGM

NLDSLYLVAIVYRTDIKTIRDLRYSDRQWLINLNNKIRSIVPGCYNYAVH

PDELRILVHYQPSYYHFHIHIVNIKHPGLGNSIAAGKAILLEDIIEMLNY

LGPEGYMNKTITYAIGENHDLWKRGLEEELTKQLERDGIPKIPKIVNGFK
```

S. pombe Nhm1p
(SEQ ID NO: 8)
```
MEESSAAKIQLLKEFKFEKILKDDTKSKIITLYGKIRNEVALLLLEKTAF

DLNTIKLDQLATFLQDTKLVENNDVFHWFLSTNFQDCSTLPSVKSTLIWP

ASETHVRKYSSQKKRMVCETPEMYLKVTKPFIETQRGPQIQWVENILTHK

AEAERIVVEDPDPLNGFIVIPDLKWDRQTMSALNLMAIVHATDIASIRDL

KYKHIPLLENIRNKVLTEVPKQFSVDKNQLKMFVHYLPSYYHLHVHILHV

DHETGDGSAVGRAILLDDVIDRLRNSPDGLENVNITFNIGEQHFLFQPLT

NMNA
```

Many DcpS and APTX enzymes are easily identifiable by sequence homology. Several examples of capping enzymes are shown in the sequence alignments of FIG. 14 and FIG. 15. The substrate specificity, of any of the enzymes in these families can be tested using the method described below and many, if not all, of these enzymes can be used in the present method.

After the population of RNA molecules has been enriched, the RNAs may be converted to cDNA, amplified, and sequenced by a variety of methods, as described below. For example, in some embodiments, cDNA synthesis may be primed by an oligod(T) primer. If the target population of RNA does not already have a polyA tail, then in some embodiments, a "synthetic" polyA tail may be added to the RNA, e.g., using a polyA polymerase or by ligating an oligonucleotide onto those molecules. Alternatively, an adaptor can be ligated onto the 3' end of the enriched RNAs, and cDNA synthesis may be primed by a primer that hybridizes to the added adaptor.

In some embodiments, the method may comprise enzymatically removing the affinity tag-labeled GMP (for examples using RNA 5' pyrophosphohydrolase (RppH) (New England Biolabs, Ipswich, Mass.), or tobacco acid pyrophosphatase (TAP) (Epicentre, Madison, Wis.) and, as described, then adding a tail (e.g., a single tract of As, Cs, Gs or Ts) onto the 3' ends of the cDNA molecules using a TdT, i.e., a template-independent polymerase. In these embodiments, the TdT may add a tail comprising a plurality of (e.g., 7-50 or 10-20 nucleotides) the same nucleotide (e.g., Gs or Cs) to the 3' end of the cDNA.

In some embodiments, the sample comprises bacterial RNA species and, as such, targeted RNA species should comprise a 5'-ppp nucleotide or 5'-pp nucleotide (which are substrates for the capping enzyme). In some embodiments, the affinity tag-labeled GMP may be DTB-GTP or variants thereof. DTB has high affinity for streptavidin and it can be eluted from streptavidin using biotin. As such, DTB-GTP can be used if the enriched RNA is going to be eluted from the affinity matrix. In some embodiments, the RNA that is bound to the affinity matrix may be in a buffer containing a reduced concentration of salt, e.g., a concentration of salt (e.g., NaCl) that is in the range of 150 mM-350 mM.

As would be apparent, reverse transcription can be done using an oligo-dT for hybridizing to the polyA tail at the 3' end of the RNA, and priming the reverse transcriptase. In some embodiments, the RNA may already have a polyA tail. In some embodiments, the polyA tail may be added after the RNA is isolated, using a polyA polymerase. Reverse transcription can also be done using a gene-specific primer (or mixture or the same) or a random primer.

In some embodiments, the method comprises, after reverse transcription but before tailing, treating the population of cDNAs with a single stranded RNAse, e.g., RNase If, which does not degrade DNA and has a preference for single-stranded RNA. This step, in theory, should cleave the single stranded region of any RNA molecules that are not part of a full duplex, thereby allowing fully duplexed RNA molecules (one strand of which should be full length cDNA) to be isolated.

As noted above, the tail added by the terminal transcriptase can be used to prime second strand cDNA synthesis. As such, in some embodiments, the method may comprise making second strand cDNA using a primer that hybridizes to the added tail. For example, if the tail added by the TdT is a polyG tail, then the primer that primes second strand cDNA synthesis should be an oligo-(dC) primer. After second strand cDNA has been made, the cDNA may be amplified, e.g., by PCR. In some embodiments, the primers used for first and second strand cDNA synthesis may themselves have primer sites at their 5' ends (which do not hybridize to the cDNA), thereby allowing the cDNA to be amplified by PCR. In some cases, these primers may contain a deoxyuracil (dU) at a specific position, e.g., near the 5' end of the primers such as within 1, 2, 3, 4 or more nucleotides from the 5' end of the primer. In these embodiments, the method may comprise cleaving the amplification products USER enzyme mix to produce overhangs at the ends of the amplification products. This enzyme mix generates a single nucleotide gap at the location of a uracil. USER enzyme is a mixture of UDG and the DNA glycosylase-lyase Endonuclease VIII. UDG catalyses the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released. As shown in FIG. 1C, the amplification products may be cleaved to produce 2, 3, or 4 or more base overhangs which can be ligated to adaptors, e.g., Y adaptors, bubble adaptors or loop adaptors and then sequenced.

Sequencing may be done in a variety of different ways, e.g., using Illumina's reversible terminator method, Roche's pyrosequencing method (454), Life Technologies' sequencing by ligation (the SOLiD™ platform), Life Technologies'

Ion Torrent platform, Pacific Biosciences' fluorescent base-cleavage method. In some embodiments, however, the products may be sequenced using a long read sequencing approach such as Nanopore sequencing (e.g. as described in Soni, et al., Clin Chem 53: 1996-2001 2007, and developed by Oxford Nanopore Technologies) or Pacific Biosciences' fluorescent base-cleavage method (which currently have an average read length of over 10 kb, with some reads over 60 kb). Alternatively, the products may be sequenced using, the methods of Moleculo (Illumina, San Diego, Calif.), 10× Genomics (Pleasanton, Calif.), or NanoString Technologies (Seattle, Wash.).

In some embodiments, the method may comprise ligating a loop adapter to one or both ends of the cDNA, thereby producing a "dumbbell" structure that can be sequenced using Pacific Biosciences' fluorescent base-cleavage method (which currently have an average read length of over 10 kb, with some reads over 60 kb). The Pacific Biosciences' sequencing system has certain advantages in that the same, circular, molecule can be sequenced several times.

A population of full length cDNAs produced by this method should contain all possible splice variants, and should allow one to perform an unbiased analysis of transcriptional starts. Examination of the sequence of the enriched molecules can provide insight into RNA splicing, TSS and operon analysis.

The compositions and methods provided herein provide a means to efficiently obtain and sequence long transcripts which have been capped with DTB or biotin. The bacterial genome generates mRNA transcripts having a 5'ppp Nucleotide. In contrast, eukaryotic mRNA is m$^7$Gppp capped.

The amplified cDNA was sequenced using a long read sequencing machine such as Pacific Biosciences, Oxford Nanopore or any suitable system.

In one embodiment, SMRT® sequencing (Pacific Biosciences, Menlo Park, Calif.) was used to sequence single cDNA molecules. Current SMRT sequencing uses either blunt end or T/A ligation for adding its loop adapter to both ends of the amplified DNA. However, the blunt end or T/A ligation is not very efficient and therefore requires a large amount of DNA for ligation. Second, blunt end ligation generates DNA chimera from self-ligation and adapter dimer, which affects the downstream sequencing. To improve the ligation efficiency and quality, an improved ligation method was developed. A pair of primers containing dU was used near the 5'end for DNA amplification. The dU base was removed by USER enzyme, thus creating cohesive-ends (5'recessed ends) of the amplified DNA, which match the 3' overhang of the adapter (loop adapter for Pac Bio) The cohesive-ends ligation increased the ligation efficiency, shortened the ligation time, and greatly reduced self-ligation, chimera and adapter dimer formation.

In some embodiments, the use of a biotin or preferably a DTB cap for enriching for mRNA combined with a relatively unbiased method of adding primer sequences to the 3' end of the cDNA followed by efficient adapter ligation prior to sequencing revealed the sequence of single original RNA molecule. In this way, prokaryotic operon structure and/or the eukaryotic transcriptome were analyzed to reveal new insights in gene expression.

In embodiments of the method, a DTB cap was added specifically to the 5"end of triphosphate RNAs. Processed RNA e.g. rRNA and tRNA as well as degraded RNA with either mono or hydroxyl end were not capped. In one embodiment, a polyA tail was added to the 3' end of the RNAs, which facilitated the following reverse transcription reaction using an oligodT primer. In some cases, the reverse transcriptase does not fully copy the entire mRNA hence there may be a single stranded RNA at the 5' end. In one embodiment, an RNase such as RNase I$_f$ (New England Biolabs, Ipswich, Mass.) was added for cleaving single-stranded RNA and not cDNA/RNA hybrid. The oligodT RT primer may include a UID and/or adapter sequence (adpaterR) for primer binding. The adapter sequence added at the 5'end of synthesized cDNA was used for PCR amplification (FIG. 1C). The UID may be used to determine and remove the PCR duplicates. The main purpose of removing duplicates was to mitigate the effects of PCR amplification bias introduced during library construction.

The adapter sequence added to the 3' end of cDNA enabled subsequent synthesis of the second strand from the first strand cDNA where TdT was used to attach a polyG linker to the 3' end of single-stranded cDNA for second-strand synthesis (FIG. 1B).

In one embodiment, a second enrichment step was used to further separate the intact cDNA generated from desthiobiotinylated mRNA, from the incomplete cDNA that has not reached the 5' cap site, prior to a first PCR amplification. The product from the first PCR amplification then underwent a second amplification step with the second set of primers. The second set of primers contained adapterL and adapterR binding sites. In addition, they contained dU near the 5' end of the amplified DNA. LongAmp polymerase was used in the examples to read through dU and amplify large fragments. The polymerase added a non-templated adenosine to the 3' end of the PCR product. The dU base was later removed by USER enzyme mix, which included UNG or UDG, to create a cohesive-end (3 bp) for ligation to a sequencing adapter (see for example FIG. 1C). An advantage of the step that utilized USER was that cohesive-end ligation increased the ligation efficiency and shortened the ligation time. Importantly, it substantially prevented self-ligation, chimera and adapter dimer formation.

As shown in FIG. 2, up to 85% of the reads in the control were mapped to the processed RNA while in the sample enriched for mRNA, 85% of the reads were mapped to mRNA, while the processed RNA accounted for 15% of the total reads.

Embodiments of the method substantially enriched for full length mRNA transcripts and efficiently removed the processed RNAs, allowing for improved transcriptome coverage.

Based on the data described below, different decapping enzymes may have different specificities and, as such, can be used to classify the cap structures at the 5' ends of RNA molecules in a sample. One embodiment of the method is shown in the work flow in FIG. 13. In these embodiments, different portions (a plurality of portions) of a sample may be decapped using different enzymes, or no enzyme.

The different portions containing decapped products can then be individually capped, e.g., chemically or enzymatically, and then enriched, and sequenced. The sequences can then be analyzed to identify a difference in the cap structure of, for example, transcripts for a particular gene at a single nucleotide resolution. The analysis may reveal what the cap structure is not (e.g. the cap structure may not be m$^7$Gppp etc. See for example, FIG. 9). Examples of analysis of cap structures is shown in FIGS. 10-12.

In some embodiments decapping enzymes are utilized that leave a 5' diphosphate, e.g., by a member of the HIT superfamily of pyrophosphatases e.g., DcpS, or APTX; or NUDIX family such as NUDT12 or NUDT15 or any of the enzymes listed in FIG. 14 and FIG. 15.

In some embodiments, the affinity tag-labeled GMP is added to the 5' ends of the RNA molecules in the first and second decapped RNA samples using a capping enzyme. The RNA comprising the affinity tag-labeled GMP may be enriched using an affinity matrix that binds to the affinity tag to produce a first and second enriched samples. The first and second samples may be reverse transcribed to produce first and second cDNA libraries. The cDNA libraries may be sequenced and any differences in the caps may be identified by analyzing the sequences obtained by sequencing the first cDNA library relative to the sequences obtained by sequencing the second cDNA library.

These methods are relevant because the canonical Cap found in eukaryotes is an m$^7$G linked to the 5' terminal nucleotide of the RNA via a 5'-5' triphosphate linkage. There have been other caps identified on eukaryotic RNA's such as methyl-pppNNNNNNNN found on 7SK, U6 RNAs (Xue, et al, Nucleic Acids Research. 2010 38: 360-9) and 2,2, m$^7$GpppNNNNNNNN, found on U1, U2 U3 RNA and NMNppANNNNNNN, found on mRNA, and snoRNA (Jiao, et al., Cell. 2017; 168:1015-1027.e10; Walters, et al., Proc. of the Natl. Acad. of Sci. 2017 114: 48075., Chen, et al., Nature Chemical Biology. 2009; 5:879-81). Furthermore Abdelhamid, et al., PLoS ONE. 2014; 9:e102895, has described a plethora of different caps on human RNA.

In some embodiments the affinity tag-labeled GMP is added to the 5' ends of the RNA molecules in the first and second decapped RNA samples chemically. If a decapping enzyme cleaves between the alpha and beta phosphodiester bond of a capped RNA, the resulting monophosphate RNA cannot be recapped using capping enzymes such as VCE. In this case, the monophosphate RNA can only be recapped chemically. Chemical capping works for all 5' tri-, di and monophosphate RNA species. Chemical capping may be used as a way to "protect" tri-, di and monophosphate RNAs from unwanted capping with affinity tag-labeled GMP, for example, by adding a chemical moiety (including but not necessarily having a cap-like structure) before the decapping/recapping described herein. Currently, avoidance of unwanted capping is achieved by dephosphorylation. However, chemical addition of a cap structure that is only cleaved by certain decapping enzymes, would enable the "protected" RNA species to be later recapped and enriched as needed (including dephosphorylated RNA).

Kits

Also provided by this disclosure are kits for practicing the subject method, as described above. In certain embodiments, the kit may comprise DTB-GTP, TdT and a reverse transcriptase. In some embodiments, the kit may additionally contain any one or more of the components listed above. For example, a kit may also comprise one or more primers, e.g., a primer for making first strand cDNA, an oligo-dC/dG primer or PCR primers, and one or more adaptors, e.g., one or more adaptors that that comprise dU. In other embodiments, the kit may comprise a de-capping enzyme (e.g., several capping enzymes that have different specificities), a capping enzyme, a reverse transcriptase, DTB-GTP, and an oligo-dT primer, and may optionally contain an affinity matrix, etc. The various components of the kit may be present in separate containers or certain compatible components may be precombined into a single container, as desired. In addition to the probe, the kit may contain any of the additional components used in the method described above, e.g., a buffer, etc.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

All publications, patents, and patent applications mentioned in this specification are herein incorporated by reference to the same extent as if each individual publication, patent, or patent application was specifically and individually indicated to be incorporated by reference. This includes U.S. provisional application Ser. No. 62/409,151, filed on Oct. 17, 2016; U.S. application Ser. No. 15/137,394 filed Apr. 25, 2016; U.S. provisional application Ser. No. 62/166, 190, filed on May 26, 2015; PCT/US2014/068737, filed on Dec. 5, 2014; U.S. provisional application Ser. No. 61/912, 367, filed on Dec. 5, 2013; U.S. provisional application Ser. No. 61/920,380, filed on Dec. 23, 2013; U.S. provisional application Ser. No. 62/002,564 filed on May 23, 2014; and U.S. provisional application Ser. No. 62/011,918 filed on Jun. 13, 2014, all of which applications are incorporated by reference herein in their entireties for all purposes.

EMBODIMENTS

Embodiment 1. A method for making a cDNA library with significantly reduced bias, comprising:
(a) adding an affinity tag-labeled GMP to the 5' end of targeted RNA species in a sample by incubating the sample with an affinity tag-labeled GTP and a capping enzyme;
(b) enriching for RNA comprising the affinity tag-labeled GMP using an affinity matrix that binds to the affinity tag;
(c) reverse transcribing the enriched RNA to produce a population of cDNAs; and
(d) adding a tail to the 3' end of the population of cDNAs using a TdT, to produce an unbiased cDNA library.

Embodiment 2. The method of embodiment 1, wherein sample comprises bacterial RNA and the targeted RNA species comprise a 5'-ppp nucleotide.

Embodiment 3. The method according to any prior embodiment, wherein the affinity tag-labeled GTP is DTB-GTP.

Embodiment 4. The method according to any prior embodiment, wherein, the TdT adds a tail comprising a plurality of Gs at the 3' end of the cDNA.

Embodiment 5. The method according to embodiment 4, wherein the plurality of Gs is in the range of 10 to 20 nucleotides.

Embodiment 6. The method according to any prior embodiment, wherein the enriching comprises selectively binding the RNA to streptavidin beads in a buffer containing 1 M-3 M salt.

Embodiment 7. The method according to any prior embodiment, further comprising eluting the RNA that is bound to the affinity matrix in a buffer containing a reduced concentration of salt.

Embodiment 8. The method according to embodiment 7, wherein the reduced concentration of salt is in the range of 150 mM-350 mM.

Embodiment 9. The method according to embodiment 7 or 8, wherein the salt is NaCl.

Embodiment 10. The method according to any prior embodiment, wherein the reverse transcribing is done using oligo-dT primer.

Embodiment 11. The method according to any prior embodiment, wherein the method comprises, after step (c) but before step (d), treating the population of cDNAs with a single stranded RNAse.

Embodiment 12. The method according to any prior embodiment, further comprising making second strand cDNA using a primer that hybridizes to the tail added in step (d).

Embodiment 13. The method according to any prior embodiment, further comprising amplifying the unbiased cDNA library.

Embodiment 14. The method according to any prior embodiment, further comprising amplifying the unbiased cDNA library using primers that comprise dU.

Embodiment 15. The method according to embodiment 14, further comprising cleaving the product of amplification using USER mix to produce overhangs at the ends of the amplification products.

Embodiment 16. The method according to embodiment 16, further comprising ligating a loop adapter to one or both ends of the cDNA.

Embodiment 17. A method determining the transcriptional start and/or termination site, comprising:
 (a) performing the method of embodiment 1;
 (b) sequencing the unbiased cDNA to produce a plurality of sequence reads; and
 (c) determining a transcription start site and/or a transcription termination site by mapping the sequence reads onto a genomic sequence.

Embodiment 18. A kit comprising: DTB-GTP, TdT and a reverse transcriptase.

Embodiment 19. The kit of embodiment 18, further comprising one or more primers.

Embodiment 20. The kit of any prior kit embodiment, further comprising one or more adaptors that comprise dU.

Embodiment 21. The method or kit described above further comprising adding a poly A tail to the 3' end of the RNA.

Embodiment 22. The method of 21, wherein a poly dT primer for hybridizing to the poly dA tail initiates reverse transcription of the RNA.

Embodiment 23. A method for making a eukaryotic cDNA library, comprising:
 (a) treating a sample comprising capped, eukaryotic RNA species with a decapping enzyme to produce decapped eukaryotic RNA;
 (b) adding an affinity tag-labeled GMP to the 5' end of the decapped eukaryotic RNA molecules by incubating the decapped eukaryotic RNA with an affinity tag-labeled GTP and a capping enzyme;
 (c) enriching for RNA comprising the affinity tag-labeled GMP using an affinity matrix that binds to the affinity tag; and
 (d) reverse transcribing the enriched RNA to produce a full length eukaryotic cDNA library.

Embodiment 24. The method of embodiment 23, wherein the decapping enzyme of step (a) is a member of the HIT superfamily of pyrophosphatases.

Embodiment 25. The method of embodiment 23, wherein the decapping enzyme of DcpS or APTX.

Embodiment 26. The method of embodiment 25, wherein the decapping enzyme is *Saccharomyces cerevisiae* APTX or *Schizosaccharomyces pombe* APTX.

Embodiment 27. The method of embodiment 23, wherein the decapping enzyme of step (a) is a member of the NUDIX family of enzymes for example, NUDT12 or NUDT15.

Embodiment 28. The method of any of embodiments 23-27, wherein the long or full length, capped, eukaryotic RNA molecules of step (a) are isolated from a mammal.

Embodiment 29. The method of any of embodiments 23-28, further comprising eluting the RNA that remains bound to the affinity matrix after step (c) but prior to step (d).

Embodiment 30. The method of embodiment 29, wherein the eluting is done using a buffer containing a reduced concentration of salt.

Embodiment 31. The method according to embodiment 1, wherein (a) further comprises classifying the 5' cap structure of the sample of capped eukaryotic RNA species.

Embodiment 32. The method according to embodiment 31, wherein the step of classifying the 5'cap structure comprising steps selected from steps i-iv; steps i-v; and steps i-vi,
 (i) treating each of one or more portions of the capped eukaryotic RNA species with a different decapping enzyme and optionally treating one portion with no decapping enzyme;
 (ii) adding an affinity tag to the 5' end of the RNA species in each portion using a capping enzyme and/or a chemical method;
 (iii) enriching for affinity tagged RNA species in each portion using an affinity matrix that binds to the affinity tag;
 (iv) separately reverse transcribing enriched RNA to produce corresponding cDNA libraries;
 (v) sequencing the cDNA libraries; and
 (vi) comparing the sequences obtained from the cDNA libraries.

Embodiment 33. The method of embodiment 23 or 32, wherein the decapping enzyme leaves a 5' diphosphate.

Embodiment 34. The method of embodiment 33, wherein the decapping enzyme is a member of the HIT superfamily of pyrophosphatases or an APTX.

Embodiment 35. The method of embodiment 34, wherein the decapping enzyme is DcpS, or APTX Embodiment 35. The method of embodiment 23 or 32, wherein the decapping enzyme is a NUDIX family of hydrolytic enzymes, for example, NUDT12 or NUDT15.

Embodiment 36. The method of any of embodiments 23-35, wherein the affinity tag-labeled GMP is added to the 5' ends of the RNA molecules in the first and second decapped RNA samples chemically.

Embodiment 37. The method of any of embodiments 23-35, wherein the affinity tag-labeled GMP is added to the 5' ends of the RNA molecules in the first and second decapped RNA samples using a capping enzyme.

Embodiment 38. The method of any of the above embodiments 21-37, wherein an oligod(T) primer is hybridized to the 3'poly (A) tail on the RNA to facilitate primer dependent amplification and cloning.

EXAMPLES

Examples are provided herein for purposes of illustration and are not intended to be comprehensive nor should they limit the scope of the embodiments described herein.

Example 1: Preparation of a Library Containing cDNA of Enriched Full Length mRNA The experimental design for cDNA synthesis and library preparation is explained in FIG. 1A-FIG. 1C. The preparation of the library does not require each step described below. However at least 2 or more steps are use in the preparation of samples for single molecule sequencing.

A. A Desthiobiotin Cap was Added to the 5' End of Primary Transcripts from *E. coli* as Follows:

| | |
|---|---|
| *E. coli* total RNA | 10 μg |
| Vaccina Capping enzyme (M0280) | 20 μl |
| 10X Vaccina Capping buffer | 20 μl |
| 5 mM DTB-GTP | 20 μl |
| Yeast Pyrophosphatase (M2403) | 5 μl |
| Total | 200 μl |

The reaction mixture was incubated at 37° C. for 1 hour followed by a purification step using AM PURE® beads (Beckman Coulter, Brea, Calif.) for binding nucleic acids. These were subsequently eluted in Tris-EDTA buffer. Only bacterial mRNA was capped.

B. A polyA Tail was Added to the 3'End of Nucleic Acids to Facilitate the Subsequent Reverse Transcription Reaction Involving an oligodT Primer. Addition of the polyA Tail was Performed as Follows:

| | |
|---|---|
| Capped AMPure bead bound *E. coli* RNA | 72 μl |
| *E. coli* polyA polymerase (M0276) | 8 μl |
| 10X polyA polymerase buffer | 10 μl |
| 10 mM ATP | 10 μl |
| Total | 100 μl |

The reaction was incubated at 37° C. for 15 minutes.

A first portion of the desthiobiotinylated RNA was used for enrichment, and a second portion of the desthiobiotinylated RNA was identified as Control RNA.

C. Desthiobiotinylated RNAs was Enriched as Follows:

The first portion of desthiobiotinylated RNA was enriched for non-degraded primary RNA transcripts using the following protocol: Equal volumes of streptavidin beads and the first portion were combined and incubated at room temperature for 30 minutes in the presence of 1 M NaCl, and sequentially washed in the buffers containing 2 M NaCl and 250 mM NaCl. The beads were then incubated with a buffer containing 1 mM biotin and the flow-through containing the enriched eluted non-degraded primary RNA transcripts saved for subsequent steps.

Reverse transcription, first strand cDNA synthesis:

The enriched desthiobiotinylated RNA was reverse transcribed as follows:

| | |
|---|---|
| 10 mM dNTP | 8 μl |
| 10 uM oligodT RT primer | 4 μl |
| RNA template | 20 μl (Control) or 40 μl (Enrich) |
| Add H2O to total | 51 μl |
| 5X ProtoScript ® II buffer | 16 μl |
| ProtoScript II (M0368) | 4 μl |
| Murine RNase Inhibitor (M0314) | 1 μl |

Incubate at 42° C. for 1 hour.

For enriched samples, RNase $I_f$ was added, and the RNA purified using AMPURE beads and eluted in Tris EDTA buffer.

For the control group, the sample was purified using AMPURE beads and then eluted in Tris EDTA buffer.

D. Addition of a polyG Linker to the 3' End of Synthesized cDNA:

| | |
|---|---|
| cDNA | 39 μl |
| TdT (M0315) | 1 μl |
| 10X TdT buffer | 5 μl |
| 100 mM dGTP | 1 μl |

Incubate at 37° C. for 0.5 hours.

A second enrichment step: Enrichment of cDNA generated from mRNA with intact 5'end.

The reacted cDNA from the enriched RNA was added to streptavidin beads in the presence of 1M NaCl. The control group TdT reaction was purified using AMPURE beads.

E. Second Strand DNA Synthesis of the cDNA was Performed as Follows:

| | |
|---|---|
| Q5 2X mix (M0541) | 25 μl |
| cDNA (with beads for enriched sample) | 5 μl |
| 10 uM PacBio_oligodC forward primer | 2.5 μl |
| 10 uM PacBio reverse primer | 2.5 μl |
| H$_2$O | 14 μl |
| Total | 50 μl |

98° C. for 1 minute; [98° C. for 10 seconds, 65° C. for 30 seconds; 72° C. for 4 minutes] X9 cycles; 72° C. for 5 minutes.

The product of the PCR reaction was purified using AMPURE beads.

F. Large Scale PCR for Size Selection:

| | |
|---|---|
| 1$^{st}$ round PCR product | 0.5 μl |
| 10 uM PacBio_for_dU primer | 2 μl |
| 10 uM PacBio_rev_dU primer | 2 μl |
| H2O | 20.5 μl |
| Total | 50 μl |

94° C. for 1 minute; [94° C. for 30 seconds, 65° C. for 6 minutes] Xn cycles; 65° C. for 10 minutes.

The second PCR product was purified on AMPURE beads.

G. SMRTbell™ Template Preparation (Advanced Analytical Inc., IA) and size selection for sequencing using PACBIO sequencer (Pacific Biosystems, CA).

| | |
|---|---|
| 2nd round PCR product or size selected 2nd round PCR product (0.2-1 μg) | 26 μl |
| USER (M5505) | 4 μl |
| Total | 30 μl |

Incubate at 37° C. for 0.5 hour
Add:

| | |
|---|---|
| 10X T4 ligation buffer | 10 μl |
| 2000 U/μl T4 ligase | 5 μl |
| 20 μM annealed PacBio TGT adapter | 15 μl |
| H$_2$O | 40 μl |
| Total | 100 μl |

Incubate at 25° C. for 0.5 hour; then inactivate T4 ligase at 65° C. for 10 minutes.

ExoIII and ExoVII were added to remove failed ligation products. The reaction was incubated at 37° C. for 1 hour and the product purified using AMPURE beads.

Qualitative and quantitative analysis was performed using a Bioanalyzer instrument (Agilent, Santa Clara, Calif.). Size selection was achieved using Bluepippin (Sage Science, Beverly, Mass.) and the DNA was sequenced.

Primers Used:

```
RT_dTVN_UID:
                                            (SEQ ID NO: 26)
5'-GTGACTGGAGTTCAGACGTGTGCTCTTCCGATCTNNNNNNNGCGCttt tttttttttttttttttVN PacBio reverse:
                                            (SEQ ID NO: 27)
5'/5Phos/GTGACTGGAGTTCAGACGTGTGCTCTTCCGATCT PacBio_oligodC20 forward:
                                            (SEQ ID NO: 28)
ACACTCTGTCGCTACGTAGATAGCGTTGAGTGCCCCCCCCCCCCCCCCCC

CC

Pac_for_dU:
                                            (SEQ ID NO: 29)
5'-G/ideoxyU/ACACTCTGTCGCTACGTAGATAGCGTTGAGTG Pac_rev_dU:
                                            (SEQ ID NO: 30)
5'G/ideoxyU/GTGACTGGAGTTCAGACGTGTGCTCTTCCGATCT Pac_adapter_TGT:
                                            (SEQ ID NO: 31)
/5Phos/ATCTCTCTCTTTTCCTCCTCCTCCGTTGTTGTTGTTGAGAGAG ATtgt
```

Example 2: Full Length Cappable-Seq Using *E. coli* Total RNA

Two PACBIO sequencing libraries were generated using either (B) TdT or (C) Template switch. The nucleotide preference from −5 to +5 position of TSS was analyzed for each method.

Previously the TSS of *E. coli* was identified by the Cappable-seq method for fragmented RNA, based on 5' ligation at the position defined by DTB capping followed by Illumina sequencing.

In the library generated with a standard ligation based method, 32%, 50%, 12% and 6% of the captured TSS start with G, A, T and C, respectively (A).

The cDNA library generated using template switching resulted in 72% of the captured TSS that started with G, while only 20%, 5%, and 3% of captured TSS started with A, T and C, respectively. See for example FIG. 4C. Template switching was found to introduce significant bias towards G at the TSS. This correlated with an inefficient template switch for desthiobiotinylated RNA template that started with A, C or T. The template switch of desthiobiotinylated RNA starting with G was found to be at least 4 times more efficient than desthiobiotinylated RNA starting with an A. The use of TdT in place of template switching removed the observed bias (see FIG. 4B).

Example 3: Decapping m$^7$G Capped RNA with DcpS

A collection of RNA transcripts of 50, 80, 150, 300 500 and 1000 nucleotides was capped with m$^7$G and the resulting capped transcripts were decapped with either DcpS from *Schizosaccharomyces pombe* (NHM1) or *Saccharomyces cerevisiae* (yDcpS) and then incubated with VCE and 3' DTBGTP. The resulting RNA was either directly run on a PAGE UREA gel or enriched on streptavidin magnetic beads (see FIG. 5A). The results, as shown by the recovery of RNA from the streptavidin beads, demonstrated that both DcpS removed the m$^7$GMP and enabled the recapping with DTB-GTP.

Example 4: Decapping m$^7$G Capped RNA with APTX

Human Jurkat total RNA was decapped by treatment with *Saccharomyces cerevisiae* 5' deadenylase (APTX) and then subjected to recapping with 3'DTB-GTP and enrichment on streptavidin beads. The amount of: (a) two RNA polymerase II-transcribed mRNAs (encoding ActB and GAPDH); (b) 7SK— a structural non-capped RNA with a 5' triphosphate; and (c) 18S rRNA which terminates in a 5' monophosphate were determined by RTqPCR. The results (FIG. 56) show that the two mRNA and 5' triphosphate RNA were significantly enriched relative to ribosomal RNA.

Example 5: Decapping Recapping of a 25mer Cap1 RNA

A 100 ul reaction mix containing 1 ug of Cap1 25mer RNA (having a m$^7$Gppp cap) and 4.5 ug of total *E. coli* RNA was incubated with 5 ug of *Saccharomyces cerevisiae* DcpS (yDcpS) for 2 hours at 37° C. and then treated with proteinase K. The RNA was purified and was incubated at 37° C. for 30 minutes in a reaction mix with DTB-GTP with or without VCE. The RNA was analyzed on a 15% TBE UREA PAGE gel. These results, which are shown in FIG. 6, show the Cap1 oligonucleotide can be successfully decapped using DcpS and then recapped by DTB-GTP using VCE.

Example 6: Enrichment for the 5' Ends of m$^7$G Capped RNA

A 5 ug total RNA sample prepared from cultured mammalian cells, containing capped and non-capped RNA molecules, was treated with purified DcpS (or not treated with DcpS for the negative control), in 10 mM Bis Tris buffer for 1 hour at 37° C., then incubated with VCE in the recommended buffer but using DTB-GTP in the place of GTP. After the capping reaction, the RNA was fragmented by incubation at 94° C. following the guidelines for size fragmentation in the NEBNext® Ultra™ RNA Library Kit for Illumina (New England Biolabs, Ipswich, Mass.) to obtain sizes of around 200 nt. Afterwards the reaction was incubated with 1 µL T4 polynucleotide kinase for 30 minutes at 37° C. in the recommended buffer in the absence of ATP and purified with AM PURE magnetic beads, according to the manufacturer's protocol. The purified RNA sample was enriched and eluted from hydrophilic Streptavidin (SA) coated magnetic beads (New England Biolabs, Ipswich, Mass.), as described in Example 1. The eluted material was purified with AMPURE magnetic beads. 10% was used for cDNA synthesis followed by qPCR using primers for ActB, or 18S rRNA, or 7SK non-coding RNA (discussed below).

The remaining material (both from DcpS treated and untreated RNA) was used for making sequencing libraries. The RNA was treated with RppH for 1 hour at 37° C. and then purified with AM PURE magnetic beads as above. The purified material was used for Illumina sequencing library construction using the NEBNext Small RNA Library Prep Set for Illumina (New England Biolabs, Ipswich, Mass.). The sequencing reads were mapped against human genome sequences (Hg38). The results show that pre-treatment of total RNA sample with DcpS prior to library construction by Cappable-seq effectively enriches for the 5' ends of capped RNA.

Example 7: Evaluation of the Enrichment of Capped RNA

Total RNA samples were either not treated with Dcps or treated with Dcps prior to being capped with DTB-GTP using VCE and then captured on streptavidin beads using the method described in Example 6. The material eluted from the streptavidin beads were used in first strand cDNA synthesis and qPCR with primers corresponding to 18S ribosomal RNA, 7SK RNA and ActB RNA. The difference in obtained Ct values from the input samples to those eluted from streptavidin was used to calculate percent recovery from streptavidin elution.

The RT qPCR results (FIG. 7) show that non-capped RNA was successfully depleted since only 0.1 and 0.4% of ribosomal RNA was recovered after streptavidin binding, whereas over 90% capped mRNA (ActB) was quantitatively recovered only from the DcpS treated sample that allowed recapping with DTB. The tri-phosphorylated 7SK RNA was enriched (relative to ribosomal RNA) regardless of DcpS treatment since it is readily capped and requires no prior decapping.

Example 8: Analysis of Bacterial Total RNA and Eukaryotic Total RNA

FIG. 8 schematically illustrates a workflow for enrichment and sequencing of bacterial or eukaryotic primary transcripts. In this workflow, full length bacterial mRNA has a 5'ppp nucleotide that reacts with a capping enzyme such as vaccinia resulting in attachment of an affinity label such as biotin or DTB. DTB is shown here. Processed RNA (rRNA, tRNA) or degraded RNA having a single 5'p nucleotide or 5'OH does not react with the capping enzyme and cannot be capped with an affinity label. (1A): Full length eukaryotic RNA containing capped primary transcripts is treated with a decapping enzyme to produce 5'pp nucleotide, which can be capped in the same way as triphosphorylated RNA. (2): Optionally, a polyA polymerase is provided to add a polyA tail to the 3'end of RNA if reverse transcription is desirable. The polyA tail provides a target for an oligo dT primer which enable initiation of the reverse transcriptase reaction. (2A): The decapped primary transcripts react with a capping enzyme such as vaccinia resulting in attachment of an affinity label such as biotin or DTB (DTB is shown here) (also see WO 2015/085142). Processed RNA (rRNA, tRNA) or degraded RNA having a single 5'p nucleotide or 5'OH does not react with the capping enzyme and cannot be capped with an affinity label. (3): The labeled RNAs binds with high affinity to a matrix (for example, streptavidin beads) in a high salt buffer (for example, NaCl concentration above 250 mM). The uncapped and therefore unbound RNAs are washed away using the high salt buffer. (4): The affinity bound RNAs can then be eluted from the matrix in a suitable elution buffer to provide an enriched preparation of non-degraded primary transcripts.

Example 9: Synthesis of Oligonucleotides Having Different Caps

Enzymatic Capping (Generation of $m^7$GpppN-25mer, GpppN-25mer, $^{DTB}$GpppN-25mer, $^{m7\text{-}Propargyl}$GpppN-25mer, dGpppN-25mer, araGpppN-25mer, 2'-F-dGpppN-25mer). The capping of 5'-triphosphate RNA (5 nmol) was performed at a 500 µL reaction volume using the Vaccinia Capping System (New England Biolabs, Ipswich, Mass.): 100 µM 5'-triphosphate RNA (50 µL, final concentration 10 µM), water (100 µL), 10× Capping Buffer (50 µL; 50 mM Tris-HCl, 5 mM KCl, 1 mM $MgCl_2$, 1 mM DTT, pH 8 at 25° C.), 300 µM GTP (100 µL, final concentration 30 µM), 1 mM SAM (100 µL, final concentration 200 µM), Pyrophosphatase (50 µL; NEB M24035, 0.1 unit/µL), and VCE (50 µL; 1 unit/µL). For GTP analogs, a 1 mM stock solution was used to provide a final concentration of 100 µM. The RNA and water were first combined, and the solution was heated to 65° C. for 5 minutes and placed on ice for an additional 5 minutes. The remaining reaction components were added, and the reaction was allowed to proceed at 37° C. overnight. The enzyme and small molecules were removed from the reaction using phenol/chloroform extraction with Phase Lock Gel tubes (5Prime, 2302810). Briefly, the reaction was vortexed with an equivalent amount (500 µL) of phenol:chloroform, 5:1, pH 4.7 (Ambion, 9720). Up to 500 µL of this mixture was added to a Phase Lock Gel tube and centrifuged for 5 minutes at 13,000 rpm. To ensure the separation of the phases, 250 µL of chloroform (99%, Sigma-Aldrich, 372978) was added, and the tube was centrifuged for 5 minutes at 13,000 rpm. The aqueous phase containing the capped oligonucleotides was then transferred to a fresh tube and concentrated on a Savant™ SpeedVac™ (ThermoFisher Scientific, Waltham, Mass.).

This crude material was then purified using polyacrylamide gel electrophoresis. The National Diagnostics SequaGel™, UreaGel System kit (National Diagnostics, Atlanta, Ga.) was used to make a 20% acrylamide gel: for 50 mL of acrylamide gel, a solution of UreaGel Concentrate (40 mL), UreaGel Diluent (5 mL) and UreaGel Buffer (5 mL) were mixed followed by APS 10% (400 µL) and tetramethylethylene diamine (20 µL, TEM ED, National Diagnostics, Atlanta, Ga.). The mixture was immediately poured into a gel cassette (height: 28 cm, width: 16.5 cm, thickness: 1.5 mm) with the appropriate comb and allowed to polymerize at room temperature. TBE 1× Buffer was prepared from a 5× stock (AccuGENE™ 5×TBE Buffer, Lonza, Switzerland). The gel was equilibrated overnight at 600 V (constant voltage). The gel was then warmed prior to sample addition by increasing the maximum voltage to 800 V. The dried samples were resuspended in 50 µL of 7 M urea (prepared from powder: Qiagen, Valencia, Calif.) and heat-denatured at 70° C. for 5 minutes. The gel was run at 800 V (constant voltage) for up to 6 hours.

The capped oligonucleotides were revealed by UV shadowing on a white background. The band of interest were cut out and crushed in 2 mL Eppendorf tubes with disposable plastic pestles and resuspended and vortexed in 500 mM Tris pH 7.5 (500 µL). The gel particles were heated at 60° C. for 15 minutes, immediately frozen at −80° C. for 30 minutes, and then left overnight at room temperature. The gel solution was centrifuged at 15,000 rpm for 30 minutes, and the supernatant was removed and filtered with Ultrafree®-MC 0.45 µm tubes (Millipore, Burlington, Mass.). An additional 500 µL of 500 mM Tris pH 7.5 was added to the particles, vortexed, and centrifuged again. The recovered supernatant fractions were pooled and precipitated with ethanol (100 µL of 3 M sodium acetate (ThermoFisher Scientific, Waltham, Mass.) and 2 mL of 100% absolute ethanol). The mixture was vortexed and frozen for at least 30 minutes at −80° C. The tube was centrifuged for 30 minutes at 15,000 rpm, and the solution was discarded. The pellet was washed with 500 µL of 70% ethanol and centrifuged again. The sample was vacuum-dried using a SpeedVac Concentrator. The pellet of purified oligonucleotide was resuspended in 50 µL of water, and the final oligonucleotide concentration was estimated with a spectrophotometer (NanoDrop™, ND-1000, ThermoFisher Scientific, Waltham, Mass.).

Chemical Capping (Generation of NppN-25mer). Chemical capping of 5'-monophosphate RNA (5 nmol) was performed at a 250 µL reaction scale. On ice, 5'-monophosphate RNA (100 µM, 50 µL) was combined with Bis-Tris buffer (1 M, pH 6.0; 50 µL), $MnCl_2$ (1 M, 5 µL), and DMF (50 µL). To this solution was added imidazolide-NMP (100 mM, 95 µL), and the reaction was incubated at 50° C. for 5 hours. After this time, the unreacted imidazolide was removed from the reaction along with salts and organic solvent using Sep-Pak® C18 Cartridges (Waters, Milford, Mass.). Briefly, the capping reaction was diluted to 5 mL in 0.1 M triethylammonium bicarbonate (TEAB). This diluted reaction was then pushed through the Sep-Pak column and washed with an additional 15 mL of 0.1 M TEAB. The capped oligonucleotide was eluted from the column using 1:1 TEAB: Acetonitrile (2 mL). Presence of the oligonucleotide was confirmed on the NanoDrop. This crude material was concentrated on the SpeedVac and purified by polyacrylamide gel electrophoresis as before.

Chemical Capping (Generation of NpppN-25mer). Chemical capping of 5'-monophosphate RNA (5 nmol) was performed at a 250 µL reaction scale. On ice, 5'-monophosphate RNA (100 µM, 50 µL) was combined with Bis-Tris buffer (1 M, pH 6.0; 50 µL), $MnCl_2$ (1 M, 5 µL), and DMF (50 µL). To this solution was added imidazolide-NDP (100 mM, 95 µL), and the reaction was incubated at 37° C. for 5 hours. After this time, the unreacted imidazolide was removed from the reaction along with salts and organic solvent using Sep-Pak C18 Cartridges as described above. This crude material was concentrated on the SpeedVac and purified by polyacrylamide gel electrophoresis as before.

Chemical Capping (Generation of NppppN-25mer). Chemical capping of 5'-monophosphate RNA (5 nmol) was performed at a 250 µL reaction scale. On ice, 5'-monophosphate RNA (100 µM, 50 µL) was combined with Bis-Tris buffer (1 M, pH 6.0; 50 µL), $MnCl_2$ (1 M, 5 µL), and DMF (50 µL). To this solution was added imidazolide-NTP (100 mM, 95 µL), and the reaction was incubated at room temperature for 4 hours. After this time, the unreacted imidazolide was removed from the reaction along with salts and organic solvent using Sep-Pak C18 Cartridges as described above. This crude material was concentrated on the SpeedVac and purified by polyacrylamide gel electrophoresis as before.

Example 10: Different Decapping Enzymes have Different Substrate Specificities

In this example, twenty nine different 25mer synthetic RNA's with various caps (as listed in FIG. 9) were subjected to either decapping with yDcpS or *Schizosaccharomyces pombe* HNT3 enzymes and analyzed using the method described in Example 5. The sequence of the RNA is (A or C or U or G) GGAGUCUUCGUCGAGUACGCUCAAC (SEQ ID NO:32) and the caps and modifications are as indicated. The decapping reactions were in a 10 mM Bis-Tris pH6.5, 1 mM EDTA buffer. The RNA was at 100 nM and the decapping enzyme was in about 30 fold molar excess for 60 minutes at 30° C. for p.HNT3 and 37° C. for yDcpS. A black box indicate that the cap was removed. The grey box indicates the cap was not removed. The data shown demonstrates that different decapping enzymes have different substrate specificities. This observation enables one to classify the different chemical structures on the 5' end of an RNA.

Example 11: Analysis of a Eukaryotic RNA Sample Using Different Decapping Enzymes In this example, by comparing results obtained from pre-treating the samples with different decapping enzymes (e.g., DcpS or NudC) one can deduce a number of differently capped RNA at single base resolution.

Total RNA samples were either not decapped or pre-treated with the DcpS or NudC (both of which are decapping enzymes) and then analyzed by Cappable-seq (i.e., by incubating the sample with VCE and DTB-GTP and then enriching for the biotinylated RNAs using streptavidin, as described in Example 5 and U.S. application Ser. No. 15/137,394 or Cap-trapper (which adds a biotin to the RNAs via a chemical reaction, as described in Carninci, et al (Genomics. 1996 37: 327-36)). The sequencing reads were mapped against human genome sequences.

FIG. 10 shows data for the 5' end for ActB transcripts and displays the number of sequence reads from total RNA that has (i) not been pretreated with a decapping enzyme and captured using the Cap-trapper method, (ii) been pretreated with DcpS and then analyzed by the Cap-trapper method, (iii) been pretreated with NudC and then analyzed by the Cap-trapper method, (iv) not been pretreated with a decapping enzyme and then analyzed by Cappable-seq and (v) been pretreated with a DcpS and then analyzed by Cappable-seq As can be seen from the data shown in FIG. 10, DcpS (i) removes the caps from the ActB gene and prevents those transcripts from being enriched in the Cap-trapper method and (ii) enables the enrichment of the ActB transcripts using the Cappable-seq method. Comparison of the number of reads between the different treatments can give insight in the existence or not of 2' 3' cis diol structure at the 5' end since this is the structure captured by cap trapper. Conversely, loss of signal by a particular decapping enzyme denotes a cap structure that corresponds to the specificity of the particular decapping enzyme. The sequencing reads from the DcpS treated RNA library accumulate at the 5' end of the annotated mRNA for ActB and are coinciding with the positions where the CAGE reads map as well, denoting the position of the capped 5' end of each gene transcript and identifies their respective TSS. Pre-treatment with DcpS significantly depletes the reads obtained by the Cap-trapper method demonstrating the decapping activity of this enzyme against 5' caps of eukaryotic RNA. Conversely the Cappable-seq reads (i.e., with no prior decapping) are depleted since no recapping with DTB is possible in this case. Similar data were obtained for transcripts of the LDHA and TMSB10 genes.

FIG. 11 show data for the 5' ends of the mitochondrial cytochrome C oxidase transcripts. The results from Cap-trapper panels indicate that DcpS does not decrease the read number for mitochondrial cytochrome C oxidase or mitochondrial ATP synthase, whereas NudC does, suggesting a nicotinamide mononucleotide cap structure. It is known that *E. coli* NudC decaps 5' NAD capped RNA (Höfer et al. Nature Chemical Biology. 2016; 12:730-4.). In addition the absence of a Cappable-seq reads is consistent with NAD cap as DcpS does not remove NAD caps. Cap-trapper does enrich for NAD caps since they contain a ribose sugar with 2'-3' cis diol. Similar results were obtained for mitochondrial ATP synthase (not shown).

FIG. 12 show data for data for the 5' ends of EIF4E transcripts. As shown, the Cappable-seq with DcpS panel shows a high number of reads for the EIF4E gene where those obtained using the Cap-trapper method are very low. This pattern of response to Cap-trapper and Cappable-seq indicate that this is not a canonical G cap. This cap must be a cap lacking a 2'-3' cis diol and must be substrate for DcpS which after decapping leaves a 5' diphosphate end on the RNA. For example the cap could be a deoxy-guanosine or arabinose guanosine as could be predicted from FIG. 9.

Example 12: Workflow and Exemplary Analysis of a Eukaryotic RNA Sample Using Different Decapping Enzymes As shown in FIG. 13, an RNA sample can be untreated or treated, in parallel, with different decapping enzymes such as Dcps, NudC, Hnt3 or others. Subsequently different types of sequencing libraries are constructed, for example using Cap-trapper enrichment or by DTB-GTP capping (Cappable-seq). The sequencing reads are mapped on the genomic sequences and plotted using a genome browser and the number of reads for each transcribed gene obtained from the different datasets are compared. For simplicity only presence or absence of reads are indicated, aligned with five different examples of transcripts (horizontal lines) that have either $m^7$Gppp (1), m7deoxyGppp (2), triphosphate (3), NAD (4) or Appp (5) cap structures respectively.

Example 13: Enrichment of Full Length Mammalian mRNAs Using DcpS Followed by Cappable-Seq A 5 ug total RNA sample prepared from cultured mammalian cells, containing capped and non-capped RNA molecules, is optionally treated with calf intestinal phosphatase (CIP) in an appropriate phosphatase buffer and treated with purified DcpS, in 10 mM Bis Tris buffer for 1 hour at 37° C. The RNA is purified with AMPURE magnetic beads, according to the manufacturer's protocol. The RNA is treated as in Example 1A. Step 1B is not needed as the eukaryotic mRNA is naturally polyadenylated. The remaining steps 1C thru 1G are performed. Sequence analysis of the long RNAs reveals the presence and sequences of different splice isoforms of the mRNAs.

What is claimed is:

1. A method for making a eukaryotic cDNA library, comprising:
   (a) treating a sample comprising capped, eukaryotic RNA species with a decapping enzyme to produce a decapped eukaryotic RNA species;
   (b) adding an affinity tag-labeled guanosine monophosphate (GMP) to the 5' end of the decapped eukaryotic RNA species by incubating the decapped eukaryotic RNA species with an affinity tag-labeled guanosine triphosphate (GTP) and a capping enzyme;
   (c) enriching for RNA comprising the affinity tag-labeled GMP using an affinity matrix that binds to the affinity tag;
   (d) optionally adding a poly(A) tail in (a), (b), or (c);
   (e) eluting the RNA that remains bound to the affinity matrix after (c) but prior to (f), wherein the eluting comprises eluting the affinity matrix with a buffer comprising a concentration of salt in the range of 150 mM-350 mM; and
   (f) reverse transcribing the eluted RNA to produce a eukaryotic cDNA library.

2. The method of claim 1, wherein the decapping enzyme of step (a) is a member of the histidine triad (HIT) superfamily of pyrophosphatases.

3. The method of claim 2, wherein the decapping enzyme is scavenger decapping enzyme (DcpS), or an aprataxin (APTX).

4. The method of claim 3, wherein the APTX decapping enzyme is *Saccharomyces cerevisiae* APTX or *Schizosaccharomyces pombe* APTX.

5. The method of claim 1, wherein the decapping enzyme of step (a) is a member of the NUDIX family of hydrolytic enzymes.

6. The method of claim 5, wherein the NUDIX decapping enzyme is NUDT12 or NUDT15.

7. The method according to claim 1, wherein (c) further comprises selectively binding the RNA to streptavidin beads in a buffer containing 1 M-3 M salt.

8. The method according to claim 7, wherein the salt in (c) is NaCl.

9. The method according to claim 1, wherein the salt in (e) is NaCl.

10. The method according to claim 1, wherein the method comprises, after (f) treating the produced eukaryotic cDNA library with a single strand specific RNAse.

11. The method of claim 1, wherein (f) further comprises: adding a tail to the 3' end of the produced eukaryotic cDNAs using a terminal transferase.

12. The method according to claim 11, wherein the terminal transferase adds a tail comprising a plurality of Gs at the 3' end of the cDNA.

13. The method according to claim 12, wherein the plurality of Gs is in the range of 10 to 20 nucleotides.

14. The method according to claim 11, wherein step (f) further comprises using a primer that hybridizes to the 3' tails of the produced eukaryotic cDNAs to form a second strand cDNA library.

15. The method according to claim 1, wherein step (f) further comprises using an oligo-dT primer.

16. The method according to claim 1, wherein step (f) further comprises amplifying the produced cDNA library.

17. The method according to claim 16, further comprising amplifying the cDNA library using primers that comprise deoxyuridine.

18. The method according to claim 17, further comprising cleaving the product of amplification using a mix comprising uracil-N-deglycosylase (UNG) or uracil DNA glycosylase (UDG) to produce overhangs at the ends of the amplification products.

19. The method according to claim 16, further comprising ligating a loop adapter to one or both ends of the cDNA.

20. A method of classifying the 5' cap structure of a sample of capped eukaryotic RNA species, comprising:
   (a) treating separate portions of the sample with different decapping enzymes and optionally treating one portion with no decapping enzyme;
   (b) adding an affinity tag-labeled guanosine monophosphate to the 5' end of the treated RNA species by incubating each portion with the affinity tag-labeled guanosine triphosphate (GTP) and a capping enzyme or a chemical capping agent;

(c) enriching for affinity tagged RNA species in each portion using an affinity matrix that binds to the affinity tag;
(d) separately reverse transcribing enriched RNA to produce corresponding cDNA libraries;
(e) sequencing the cDNA libraries; and
(f) comparing the sequences obtained from the cDNA libraries.

* * * * *